United States Patent
Pinkerton et al.

(10) Patent No.: US 11,707,462 B2
(45) Date of Patent: Jul. 25, 2023

(54) CHECKPOINT KINASE 1 (CHK1) INHIBITORS AND USES THEREOF

(71) Applicant: Boundless Bio, Inc., San Diego, CA (US)

(72) Inventors: Anthony B. Pinkerton, Rancho Santa Fe, CA (US); Stephen Todd Meyer, San Diego, CA (US); Jacques Mauger, San Diego, CA (US); Yen Pham Hong Truong, San Diego, CA (US); Rachelle Janette Elsdon, San Diego, CA (US)

(73) Assignee: BOUNDLESS BIO, INC., San Diego, CA (US)

( * ) Notice: Subject to any disclaimer, the term of this patent is extended or adjusted under 35 U.S.C. 154(b) by 0 days.

(21) Appl. No.: 17/897,667

(22) Filed: Aug. 29, 2022

(65) Prior Publication Data
US 2023/0026313 A1    Jan. 26, 2023

Related U.S. Application Data

(63) Continuation of application No. PCT/US2022/031141, filed on May 26, 2022.

(60) Provisional application No. 63/193,990, filed on May 27, 2021.

(51) Int. Cl.
   C07D 401/14    (2006.01)
   C07D 403/12    (2006.01)
   A61K 31/497    (2006.01)
   C07D 401/12    (2006.01)

(52) U.S. Cl.
   CPC .......... A61K 31/497 (2013.01); C07D 401/12 (2013.01); C07D 401/14 (2013.01); C07D 403/12 (2013.01)

(58) Field of Classification Search
   CPC .......................... C07D 401/14; C07D 403/12
   See application file for complete search history.

(56) References Cited

U.S. PATENT DOCUMENTS

| | | |
|---|---|---|
| 11,547,711 B2 | 1/2023 | Hassig et al. |
| 2005/0209297 A1 | 9/2005 | Sanner et al. |
| 2022/0273649 A1 | 9/2022 | Kamioka et al. |

FOREIGN PATENT DOCUMENTS

| | | |
|---|---|---|
| CN | 111253370 A | 6/2020 |
| WO | WO-0179198 A1 | 10/2001 |
| WO | WO-2010077758 A1 | 7/2010 |
| WO | WO-2015120390 A1 | 8/2015 |
| WO | WO-2017132928 A1 | 8/2017 |
| WO | WO-2021019514 A1 | 2/2021 |
| WO | WO-2021043208 A1 | 3/2021 |
| WO | WO-2021253095 A1 | 12/2021 |
| WO | WO-2022114189 A1 | 6/2022 |
| WO | WO-2022251502 A1 | 12/2022 |

OTHER PUBLICATIONS

PCT/US2022/031141 International Search Report and Written Opinion dated Aug. 19, 2022.

*Primary Examiner* — Brian E McDowell
(74) *Attorney, Agent, or Firm* — Wilson Sonsini Goodrich & Rosati

(57) ABSTRACT

Provided herein are compounds and methods for the treatment of cancer. The methods include administering to a subject in need a therapeutically effective amount of a Chk1 inhibitor disclosed herein.

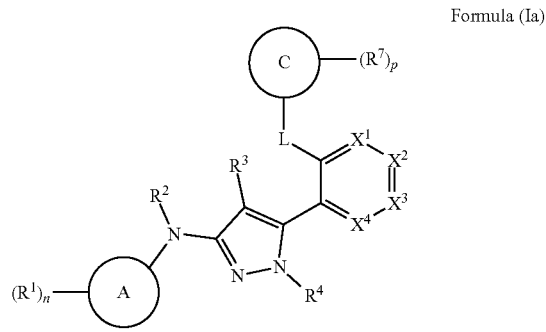

Formula (Ia)

19 Claims, No Drawings

CHECKPOINT KINASE 1 (CHK1) INHIBITORS AND USES THEREOF

CROSS-REFERENCE

This application is a continuation of International Application No. PCT/US2022/031141, filed May 26, 2022, which claims the benefit of U.S. Provisional Application Ser. No. 63/193,990, filed May 27, 2021, which are hereby incorporated by reference in their entirety.

FIELD OF THE INVENTION

Described herein are compounds, methods of making such compounds, pharmaceutical compositions, and medicaments comprising such compounds, and methods of using such compounds for inhibiting checkpoint kinase 1 (Chk1).

BACKGROUND OF THE INVENTION

Checkpoint kinases (Chks) are protein kinases that are involved in cell cycle control. Two checkpoint kinase subtypes have been identified, Chk1 and Chk2. Chk1 is a central component of genome surveillance pathways and is a key regulator of the cell cycle and cell survival. Chk1 is required for the initiation of DNA damage checkpoints and has recently been shown to play a role in the normal (unperturbed) cell cycle. Chk1 impacts various stages of the cell cycle including the S phase, G2/M transition, and M phase. In addition to mediating cell cycle checkpoints, Chk1 also contributes to DNA repair processes, gene transcription, embryo development, cellular responses to HIV infection and somatic cell viability.

Chk1 is essential for the maintenance of genomic integrity. Chk1 monitors DNA replication in unperturbed cell cycles and responds to genotoxic stress if present. Chk1 recognizes DNA strand instability during replication and can stall DNA replication to allow time for DNA repair mechanisms to restore the genome. Recently, Chk1 has been shown to mediate DNA repair mechanisms and does so by activating various repair factors. Furthermore, Chk1 has been associated with three particular aspects of the S-phase, which includes the regulation of late origin firing, controlling the elongation process and maintenance of DNA replication fork stability.

In response to DNA damage, Chk1 is an important signal transducer for G2/M checkpoint activation. Activation of Chk1 holds the cell in the G2 phase until ready to enter the mitotic phase. This delay allows time for DNA to repair or for cell death to occur if DNA damage is irreversible. Chk1 must inactivate for the cell to transition from the G2 phase into mitosis, Chk1 expression levels are mediated by regulatory proteins.

Chk1 has a regulatory role in the spindle checkpoint; however, the relationship is less clear as compared to checkpoints in other cell cycle stages. During this phase, the Chk1 activating element of single strand DNA (ssDNA) cannot be generated suggesting an alternate form of activation. Studies on Chk1 deficient chicken lymphoma cells have shown increased levels of genomic instability and failure to arrest during the spindle checkpoint phase in mitosis. Furthermore, haploinsufficient mammary epithelial cells illustrated misaligned chromosomes and abnormal segregation. These studies suggest Chk1 depletion can lead to defects in the spindle checkpoint resulting in mitotic abnormalities.

DNA damage induces the activation of Chk1, which facilitates the initiation of the DNA damage response (DDR) and cell cycle checkpoints. The DNA damage response is a network of signaling pathways that leads to activation of checkpoints, DNA repair and apoptosis to inhibit damaged cells from progressing through the cell cycle.

Chk1 is regulated by ATR through phosphorylation, forming the ATR-Chk1 pathway. This pathway recognizes ssDNA, which can be a result of UV-induced damage, replication stress and inter-strand cross linking. Often ssDNA can be a result of abnormal replication during S phase through the uncoupling of replication enzymes helicase and DNA polymerase. These ssDNA structures attract ATR and eventually activate the checkpoint pathway.

However, activation of Chk1 is not solely dependent on ATR; intermediate proteins involved in DNA replication are often necessary. Regulatory proteins such as replication protein A, Claspin, Tim/Tipin, Rad 17, TopBP1 may be involved to facilitate Chk1 activation. Additional protein interactions are involved to induce maximal phosphorylation of Chk1. Chk1 activation can also be ATR-independent through interactions with other protein kinases such as PKB/AKT, MAPKAPK and p90/RSK.

Chk1 interacts with many downstream effectors to induce cell cycle arrest. In response to DNA damage, Chk1 primarily phosphorylates Cdc25 which results in its proteasomal degradation. The degradation has an inhibitory effect on the formation of cyclin-dependent kinase complexes, which are key drivers of the cell cycle. Through targeting Cdc25, cell cycle arrest can occur at multiple time points including the G1/S transition, S phase and G2/M transition. Furthermore, Chk1 can target Cdc25 indirectly through phosphorylating Nek11.

Chk1 has shown to mediate DNA repair mechanisms and does so by activating repair factors such as proliferating cell nuclear antigen (PCNA), FANCE, Rad51 and TLK. Chk1 facilitates replication fork stabilization during DNA replication and repair however more research is necessary to define the underlying interactions.

There is a need for Chk1 inhibitors that are potent inhibitors of the cell cycle checkpoints that can act effectively as potentiators of DNA damaging agents to address the need for safe and effective treatments of cancer.

BRIEF SUMMARY OF THE INVENTION

Described herein are Chk1 inhibitors that are useful in treating cancer.

Disclosed herein is a compound of Formula (I), or a pharmaceutically acceptable salt, solvate, tautomer, or stereoisomer thereof:

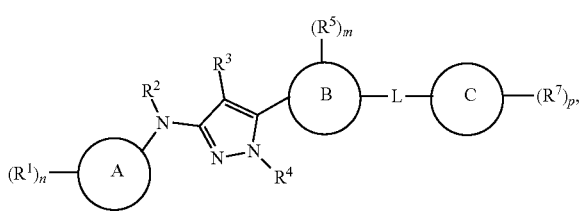

Formula (I)

wherein:

Ring A is cycloalkyl, heterocycloalkyl, aryl, or heteroaryl;

each $R^1$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NHS(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two $R^1$ on the same atom are taken together to form an oxo;

n is 0-4;

$R^2$ is hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;

$R^3$ is hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;

$R^4$ is hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;

Ring B is cycloalkyl, heterocycloalkyl, aryl, or heteroaryl;

each $R^5$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^a$, —NHS(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two $R^5$ on the same atom are taken together to form an oxo;

m is 0-4;

L is —O— or —NR$^6$—;

$R^6$ is hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;

Ring C is cycloalkyl;

each $R^7$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NHS(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two $R^7$ on the same atom are taken together to form an oxo;

p is 0-8;

each $R^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, or C$_1$-C$_6$aminoalkyl;

each $R^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, or C$_1$-C$_6$aminoalkyl; and each $R^c$ and $R^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, or C$_1$-C$_6$aminoalkyl;

or $R^c$ and $R^d$ are taken together with the atom to which they are attached to form a heterocycloalkyl optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, or C$_1$-C$_6$aminoalkyl.

Also disclosed herein in a compound of Formula (Ia), or a pharmaceutically acceptable salt, solvate, tautomer, or stereoisomer thereof:

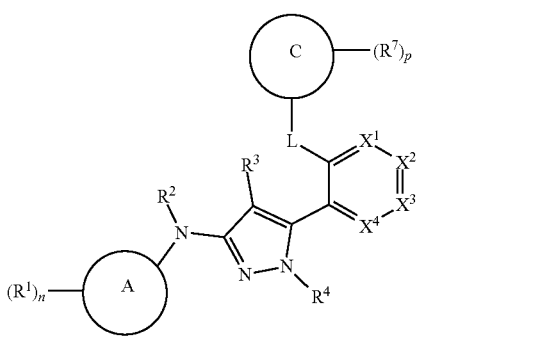

Formula (Ia)

wherein:
X$^1$ is N or CR$^{5a}$;
X$^2$ is N or CR$^{5b}$;
X$^3$ is N or CR$^{5c}$;
X$^4$ is N or CR$^{5d}$;
R$^{5a}$, R$^{5b}$, R$^{5c}$ and R$^{5d}$ are independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NHS(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl.

Also disclosed herein is a pharmaceutical composition comprising a compound disclosed herein, or a pharmaceutically acceptable salt, solvate, tautomer, or stereoisomer thereof, and a pharmaceutically acceptable excipient.

Also disclosed herein is a method of treating cancer in a subject, comprising administering to the subject a compound disclosed herein, or a pharmaceutically acceptable salt, solvate, tautomer, or stereoisomer thereof, or a pharmaceutical composition disclosed herein.

Also disclosed herein is a method of inhibiting CHK1 in a subject, comprising administering to the subject a compound disclosed herein, or a pharmaceutically acceptable salt, solvate, tautomer, or stereoisomer thereof, or a pharmaceutical composition disclosed herein.

INCORPORATION BY REFERENCE

All publications, patents, and patent applications mentioned in this specification are herein incorporated by reference for the specific purposes identified herein.

DETAILED DESCRIPTION OF THE INVENTION

Definitions

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Oxo" refers to =O.

"Alkyl" refers to an optionally substituted straight-chain, or optionally substituted branched-chain saturated hydrocarbon monoradical having from one to about ten carbon atoms, or from one to six carbon atoms. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "C$_1$-C$_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a C$_1$-C$_{10}$ alkyl, a C$_1$-C$_9$ alkyl, a C$_1$-C$_8$ alkyl, a C$_1$-C$_7$ alkyl, a C$_1$-C$_6$, alkyl, a C$_1$-C$_8$ alkyl, a C$_1$-C$_4$ alkyl, a C$_1$-C$_3$ alkyl, a C$_1$-C$_2$ alkyl, or a C$_1$ alkyl. Unless stated otherwise specifically in the specification, an alkyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —CF$_3$, —OH, —OMe, —NH$_2$, or —NO$_2$. In some embodiments, the alkyl is optionally substituted with oxo, halogen, —CN, —CF$_3$, —OH, or —OMe. In some embodiments, the alkyl is optionally substituted with halogen. In some embodiments, the alkyl is optionally substituted with —COOH, —COOMe, —CONH$_2$, —CONHMe, or —CONMe$_2$.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s) and should be understood to include both isomers. Examples include, but are not limited to, ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "C$_2$-C$_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_8$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —$CF_3$, —OH, —OMe, —$NH_2$, or —$NO_2$. In some embodiments, an alkenyl is optionally substituted with oxo, halogen, —CN, —$CF_3$, —OH, or —OMe. In some embodiments, the alkenyl is optionally substituted with halogen. In some embodiments, the alkenyl is optionally substituted with —COOH, —COOMe, —$CONH_2$, —CONHMe, or —$CONMe_2$.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to, ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —$CF_3$, —OH, —OMe, —$NH_2$, or —$NO_2$. In some embodiments, an alkynyl is optionally substituted with oxo, halogen, —CN, —$CF_3$, —OH, or —OMe. In some embodiments, the alkynyl is optionally substituted with halogen. In some embodiments, the alkynyl is optionally substituted with —COOH, —COOMe, —$CONH_2$, —CONHMe, or —$CONMe_2$.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —$CF_3$, —OH, —OMe, —$NH_2$, or —$NO_2$. In some embodiments, an alkylene is optionally substituted with oxo, halogen, —CN, —$CF_3$, —OH, or —OMe. In some embodiments, the alkylene is optionally substituted with halogen. In some embodiments, the alkylene is optionally substituted with —COOH, —COOMe, —$CONH_2$, —CONHMe, or —$CONMe_2$.

"Alkoxy" refers to a radical of the formula —Oalkyl where alkyl is as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —$CF_3$, —OH, —OMe, —$NH_2$, or —$NO_2$. In some embodiments, an alkoxy is optionally substituted with oxo, halogen, —CN, —$CF_3$, —OH, or —OMe. In some embodiments, the alkoxy is optionally substituted with halogen. In some embodiments, the alkoxy is optionally substituted with —COOH, —COOMe, —$CONH_2$, —CONHMe, or —$CONMe_2$.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Aryl" refers to a radical derived from a hydrocarbon ring system comprising hydrogen, 6 to 30 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6 to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —$CF_3$, —OH, —OMe, —$NH_2$, or —$NO_2$. In some embodiments, an aryl is optionally substituted with halogen, methyl, ethyl, —CN, —$CF_3$, —OH, or —OMe. In some embodiments, the aryl is optionally substituted with halogen. In some embodiments, the aryl is optionally substituted with —COOH, —COOMe, —$CONH_2$, —CONHMe, or —$CONMe_2$.

"Cycloalkyl" refers to a partially or fully saturated, monocyclic, or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_8$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. In some embodiments, the cycloalkyl is a 3- to 10-membered monocyclic or bicyclic cycloalkyl. In some embodiments, the cycloalkyl is a 3- to 8-membered monocyclic or bicyclic cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen. In some embodiments, the cycloalkyl is optionally substituted with —COOH, —COOMe, —CONH$_2$, —CONHMe, or —CONMe$_2$.

"Deuteroalkyl" refers to an alkyl radical, as defined above, that is substituted by one or more deuterium atoms. In some embodiments, the alkyl is substituted with one deuterium atom. In some embodiments, the alkyl is substituted with one, two, or three deuterium atoms. In some embodiments, the alkyl is substituted with one, two, three, four, five, or six deuterium atoms. Deuteroalkyl includes, for example, CD$_3$, CH$_2$D, CHD$_2$, CH$_2$CD$_3$, CD$_2$CD$_3$, CHDCD$_3$, CH$_2$CH$_2$D, or CH$_2$CHD$_2$. In some embodiments, the deuteroalkyl is CD$_3$.

"Haloalkyl" refers to an alkyl radical, as defined above, that is substituted by one or more halogen atoms. In some embodiments, the alkyl is substituted with one, two, or three halogen atoms. In some embodiments, the alkyl is substituted with one, two, three, four, five, or six halogen halogens. Haloalkyl includes, for example, trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. In some embodiments, the haloalkyl is trifluoromethyl.

"Halo" or "halogen" refers to bromo, chloro, fluoro or iodo. In some embodiments, halogen is fluoro or chloro. In some embodiments, halogen is fluoro. In some embodiments, halogen is chloro. In some embodiments, halogen is bromo. In some embodiments, halogen is iodo.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In some embodiments, a heteroalkyl is a C$_1$-C$_6$ heteroalkyl comprising one to four heteroatoms selected from the group consisting of oxygen, nitrogen, and sulfur wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, or —CH(CH$_3$)OCH$_3$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen. In some embodiments, the heteroalkyl is optionally substituted with —COOH, —COOMe, —CONH$_2$, —CONHMe, or —CONMe$_2$.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Heterocycloalkyl" refers to a 3- to 24-membered partially or fully saturated, not fully aromatic ring radical comprising 2 to 23 carbon atoms and from one to 8 heteroatoms selected from the group consisting of nitrogen, oxygen, phosphorous, and sulfur. In some embodiments, the heterocycloalkyl comprises 1 to 3 heteroatoms selected from the group consisting of nitrogen, oxygen, and sulfur. In some embodiments, the heterocycloalkyl comprises 1 or 2 heteroatoms selected from the group consisting of nitrogen and oxygen. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms (C$_2$-C$_{15}$ heterocycloalkyl), from two to ten carbon atoms (C$_2$-C$_{10}$ heterocycloalkyl), from two to eight carbon atoms (C$_2$-C$_8$ heterocycloalkyl), from two to six carbon atoms (C$_2$-C$_6$ heterocycloalkyl), from two to five carbon atoms (C$_2$-C$_8$ heterocycloalkyl), or two to four carbon atoms (C$_2$-C$_4$ heterocycloalkyl). In some embodiments, the heterocycloalkyl is a 3- to 6-membered heterocycloalkyl. In some embodiments, the cycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to, the monosaccharides, the disaccharides, and the oligosaccharides. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —CF$_3$, —OH, —OMe, —NH$_2$, or —NO$_2$. In some embodiments, a heterocycloalkyl is optionally substituted with oxo, halogen, methyl, ethyl, —CN, —CF$_3$, —OH, or —OMe. In some embodiments, the heterocycloalkyl is optionally substituted with halogen. In some embodiments, the heterocycloalkyl is optionally substituted with —COOH, —COOMe, —CONH$_2$, —CONHMe, or —CONMe$_2$.

"Heteroaryl" refers to a 5- to 14-membered ring system radical comprising hydrogen atoms, one to thirteen carbon atoms, one to six heteroatoms selected from the group consisting of nitrogen, oxygen, phosphorous, and sulfur, and at least one aromatic ring comprising at least one heteroatom. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 5- to 6-membered heteroaryl comprising 1 to 3 heteroatoms selected from the group consisting of nitrogen, oxygen, and sulfur. In some embodiments, the heteroaryl is a 5- to 6-membered heteroaryl comprising 1 to 3 heteroatoms selected from the group consisting of nitrogen and oxygen. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen. In some embodiments, the heteroaryl is optionally substituted with —COOH, —COOMe, —CONH$_2$, —CONHMe, or —CONMe$_2$.

The term "one or more" when referring to an optional substituent means that the subject group is optionally substituted with one, two, three, or four substituents. In some embodiments, the subject group is optionally substituted with one, two, or three substituents. In some embodiments, the subject group is optionally substituted with one or two substituents. In some embodiments, the subject group is optionally substituted with one substituent. In some embodiments, the subject group is optionally substituted with two substituents.

The terms "treat," "treated," "treatment," or "treating" as used herein refers to therapeutic treatment, wherein the object is to prevent or slow (lessen) an undesired physiological condition, disorder, or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. The terms "treat," "treated," "treatment," or "treating" as well as words stemming therefrom, as used herein, do not necessarily imply 100% or complete treatment. Rather, there are varying degrees of treatment of which one of ordinary skill in the art recognizes as having a potential benefit or therapeutic effect. In this respect, the disclosed methods can provide any amount of any level of treatment of the disorder in a mammal. For example, a disorder, including symptoms or conditions thereof, may be reduced by, for example, about 100%, about 90%, about 80%, about 70%, about 60%, about 50%, about 40%, about 30%, about 20%, or about 10%.

The terms "effective amount" or "therapeutically effective amount," as used herein, refer to a sufficient amount of a compound disclosed herein being administered which will relieve to some extent one or more of the symptoms of the disease or condition being treated, e.g., cancer or an inflammatory disease. In some embodiments, the result is a reduction and/or alleviation of the signs, symptoms, or causes of a disease, or any other desired alteration of a biological system. For example, an "effective amount" for therapeutic uses is the amount of the composition comprising a compound disclosed herein required to provide a clinically significant decrease in disease symptoms. In some embodiments, an appropriate "effective" amount in any individual case is determined using techniques, such as a dose escalation study.

The term "ecDNA signature" as used herein, generally refers to one or more characteristics common to tumors or tumor cells that are ecDNA+. In some cases, the ecDNA signature is selected from the group consisting of a gene amplification; a p53 loss of function mutation; absence of microsatellite instability (MSI-H); a low level of PD-L1 expression; a low level of tumor inflammation signature (TIS); a low level of tumor mutational burden (TMB); an increased frequency of allele substitutions, insertions, or deletions (indels); and any combination thereof. In some cases, ecDNA signature includes a detection or identification of ecDNA using an imaging technology. In some cases, ecDNA signature does not include any imaging or direct detection of ecDNA.

Compounds

Described herein are Chk1 inhibitor that are useful for the treatment of cancer.

Disclosed herein is a compound of Formula (I), or a pharmaceutically acceptable salt, solvate, tautomer, or stereoisomer thereof:

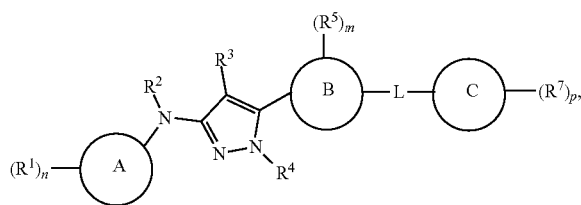

Formula (I)

wherein:
Ring A is cycloalkyl, heterocycloalkyl, aryl, or heteroaryl;
each $R^1$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NHS(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;
or two $R^1$ on the same atom are taken together to form an oxo;
n is 0-4;
$R^2$ is hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;
$R^3$ is hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;
$R^4$ is hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;
Ring B is cycloalkyl, heterocycloalkyl, aryl, or heteroaryl;
each $R^5$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NHS(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;
or two $R^5$ on the same atom are taken together to form an oxo;
m is 0-4;
L is —O— or —NR$^6$—;
$R^6$ is hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;
Ring C is cycloalkyl;
each $R^7$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NHS(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;
or two $R^7$ on the same atom are taken together to form an oxo;
p is 0-8;
each $R^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, or C$_1$-C$_6$aminoalkyl;
each $R^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, or C$_1$-C$_6$aminoalkyl; and
each $R^c$ and $R^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, or C$_1$-C$_6$aminoalkyl;
or $R^c$ and $R^d$ are taken together with the atom to which they are attached to form a heterocycloalkyl optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, or C$_1$-C$_6$aminoalkyl.

Also disclosed herein is a compound of Formula (I'), or a pharmaceutically acceptable salt, solvate, tautomer, or stereoisomer thereof:

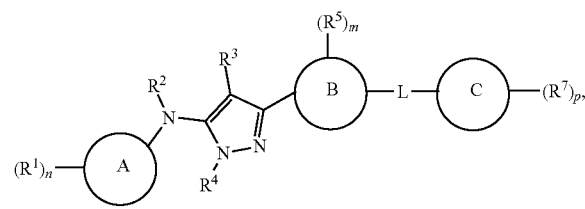

Formula (I')

wherein:

Ring A is cycloalkyl, heterocycloalkyl, aryl, or heteroaryl;

each $R^1$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^cC(=O)NR^cR^d$, —$NR^bC(=O)R^a$, —$NR^bC(=O)OR^b$, —NHS(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^1$ on the same atom are taken together to form an oxo;

n is 0-4;

$R^2$ is hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

$R^3$ is hydrogen, deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

$R^4$ is hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

Ring B is cycloalkyl, heterocycloalkyl, aryl, or heteroaryl;

each $R^5$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC(=O)NR^cR^d$, —$NR^bC(=O)R^a$, —$NR^bC(=O)OR^b$, —NHS(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^5$ on the same atom are taken together to form an oxo;

m is 0-4;

L is —O— or —$NR^6$—;

$R^6$ is hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

Ring C is cycloalkyl;

each $R^7$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC(=O)NR^cR^d$, —$NR^bC(=O)R^a$, —$NR^bC(=O)OR^b$, —NHS(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^7$ on the same atom are taken together to form an oxo;

p is 0-4;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl;

or $R^c$ and $R^d$ are taken together with the atom to which they are attached to form a heterocycloalkyl optionally substituted with one or more oxo, halogen, —CN, —OH, —$OCH_3$, —S(=O)$CH_3$, —S(=O)$_2CH_3$, —S(=O)$_2NH_2$, —S(=O)$_2NHCH_3$, —S(=O)$_2N(CH_3)_2$, —$NH_2$, —$NHCH_3$, —$N(CH_3)_2$, —C(=O)$CH_3$, —C(=O)OH, —C(=O)$OCH_3$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl.

In some embodiments of a compound of Formula (I) or (I'), Ring B is cycloalkyl or heterocycloalkyl. In some embodiments of a compound of Formula (I) or (I'), Ring B is aryl or heteroaryl. In some embodiments of a compound of Formula (I) or (I'), Ring B is aryl. In some embodiments of a compound of Formula (I) or (I'), Ring B is heteroaryl. In some embodiments of a compound of Formula (I) or (I'), Ring B is a 5- or 6-membered heteroaryl. In some embodiments of a compound of Formula (I) or (I'), Ring B is a 6-membered heteroaryl. In some embodiments of a compound of Formula (I) or (I'), Ring B is phenyl. In some embodiments of a compound of Formula (I) or (I'), Ring B is pyridyl.

In some embodiments of a compound of Formula (I) or (I'), each $R^5$ is independently deuterium, halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl. In some embodiments of a compound of Formula (I) or (I'), each R$^5$ is independently halogen, —OR$^a$, C$_1$-C$_6$alkyl, or C$_1$-C$_6$haloalkyl. In some embodiments of a compound of Formula (I) or (I'), each R$^5$ is independently halogen. In some embodiments of a compound of Formula (I) or (I'), each R$^5$ is independently —OR$^a$. In some embodiments of a compound of Formula (I) or (I'), each R$^5$ is independently C$_6$alkyl. In some embodiments of a compound of Formula (I) or (I'), each R$^5$ is independently C$_1$-C$_6$haloalkyl.

In some embodiments of a compound of Formula (I) or (I'), m is 0-2. In some embodiments of a compound of Formula (I) or (I'), m is 0 or 1. In some embodiments of a compound of Formula (I) or (I'), m is 1 or 2. In some embodiments of a compound of Formula (I) or (I'), m is 0. In some embodiments of a compound of Formula (I) or (I'), m is 1. In some embodiments of a compound of Formula (I) or (I'), m is 2. In some embodiments of a compound of Formula (I) or (I'), m is 3.

In some embodiments of a compound of Formula (I), the compound, or a pharmaceutically acceptable salt, solvate, tautomer, or stereoisomer thereof, is a compound of Formula (Ia):

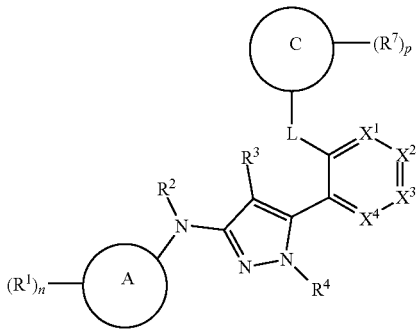

Formula (Ia)

wherein:
X$^1$ is N or CR$^{5a}$;
X$^2$ is N or CR$^{5b}$;
X$^3$ is N or CR$^{5c}$;
X$^4$ is N or CR$^{5d}$;
R$^{5a}$, R$^{5b}$, R$^{5c}$ and R$^{5d}$ are independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NHS(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl.

In some embodiments of a compound of Formula (I'), the compound, or a pharmaceutically acceptable salt, solvate, tautomer, or stereoisomer thereof, is a compound of Formula (Ia'):

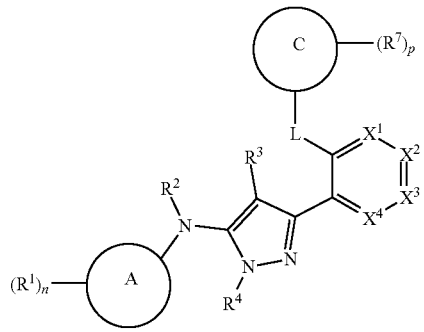

Formula (Ia')

wherein:
X$^1$ is N or CR$^{5a}$;
X$^2$ is N or CR$^{5b}$;
X$^3$ is N or CR$^{5c}$;
X$^4$ is N or CR$^{5d}$;
R$^{5a}$, R$^{5b}$, R$^{5c}$, and R$^{5d}$ are independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NHS(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl.

In some embodiments of a compound of Formula (Ia) or (Ia'), X$^1$ is N. In some embodiments of a compound of Formula (Ia) or (Ia'), X$^1$ is CR$^{5a}$.

In some embodiments of a compound of Formula (Ia) or (Ia'), R$^{5a}$ is hydrogen, deuterium, halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl. In some embodiments of a compound of Formula (Ia) or (Ia'), R$^{5a}$ is hydrogen, halogen, —OR$^a$, C$_1$-C$_6$alkyl, or C$_1$-C$_6$haloalkyl. In some embodiments of a compound of Formula (Ia) or (Ia'), R$^{5a}$ is hydrogen. In some embodiments of a compound of Formula (Ia) or (Ia'), R$^{5a}$ is halogen. In some embodiments of a compound of Formula (Ia) or (Ia'), R$^{5a}$ is —OR$^a$. In some embodiments of a compound of Formula (Ia) or (Ia'), R$^{5a}$ is C$_1$-C$_6$alkyl. In some embodiments of a compound of Formula (Ia) or (Ia'), R$^{5a}$ is C$_1$-C$_6$haloalkyl.

In some embodiments of a compound of Formula (Ia) or (Ia'), X$^2$ is N. In some embodiments of a compound of Formula (Ia) or (Ia'), X$^2$ is CR$^{5b}$.

In some embodiments of a compound of Formula (Ia) or (Ia'), R$^{5b}$ is hydrogen, deuterium, halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl. In some embodiments of a compound of Formula (Ia) or (Ia'), R$^{5b}$ is hydrogen, halogen, —OR$^a$, C$_1$-C$_6$alkyl, or C$_1$-C$_6$haloalkyl. In some embodiments of a compound of Formula (Ia) or (Ia'), R$^{5b}$ is hydrogen. In some embodiments of a compound of Formula (Ia) or (Ia'), R$^{5b}$ is halogen. In some embodiments of a compound of Formula (Ia) or (Ia'), R$^{5b}$ is —OR$^a$. In some embodiments of a compound of Formula (Ia) or (Ia'), R$^{5b}$ is $C_1$-$C_6$alkyl. In some embodiments of a compound of Formula (Ia) or (Ia'), $R^{5b}$ is $C_1$-$C_6$haloalkyl.

In some embodiments of a compound of Formula (Ia) or (Ia'), $X^3$ is N. In some embodiments of a compound of Formula (Ia) or (Ia'), $X^3$ is $CR^{5c}$.

In some embodiments of a compound of Formula (Ia) or (Ia'), $R^{5c}$ is hydrogen, deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (Ia) or (Ia'), $R^{5c}$ is hydrogen, halogen, —$OR^a$, $C_1$-$C_6$alkyl, or $C_1$-$C_6$haloalkyl. In some embodiments of a compound of Formula (Ia) or (Ia'), $R^{5c}$ is hydrogen. In some embodiments of a compound of Formula (Ia) or (Ia'), $R^{5c}$ is halogen. In some embodiments of a compound of Formula (Ia) or (Ia'), $R^{5c}$ is —$OR^{5a}$. In some embodiments of a compound of Formula (Ia) or (Ia'), $R^{5c}$ is $C_1$-$C_6$alkyl. In some embodiments of a compound of Formula (Ia) or (Ia'), $R^{5c}$ is $C_1$-$C_6$haloalkyl.

In some embodiments of a compound of Formula (Ia) or (Ia'), $X^4$ is N. In some embodiments of a compound of Formula (Ia) or (Ia'), $X^4$ is $CR^{5d}$.

In some embodiments of a compound of Formula (Ia) or (Ia'), $R^{5d}$ is hydrogen, deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (Ia) or (Ia'), $R^{5d}$ is hydrogen, halogen, —$OR^a$, $C_1$-$C_6$alkyl, or $C_1$-$C_6$haloalkyl. In some embodiments of a compound of Formula (Ia) or (Ia'), $R^{5d}$ is hydrogen. In some embodiments of a compound of Formula (Ia) or (Ia'), $R^{5d}$ is halogen. In some embodiments of a compound of Formula (Ia) or (Ia'), $R^{5d}$ is —$OR^a$. In some embodiments of a compound of Formula (Ia) or (Ia'), $R^{5d}$ is $C_1$-$C_6$alkyl. In some embodiments of a compound of Formula (Ia) or (Ia'), $R^{5d}$ is $C_1$-$C_6$haloalkyl.

In some embodiments of a compound of Formula (I), (I'), (Ia), or (Ia'), Ring A is cycloalkyl or heterocycloalkyl. In some embodiments of a compound of Formula (I), (I'), (Ia), or (Ia'), Ring A is aryl or heteroaryl. In some embodiments of a compound of Formula (I), (I'), (Ia), or (Ia'), Ring A is heteroaryl. In some embodiments of a compound of Formula (I), (I'), (Ia), or (Ia'), Ring A is 5- or 6-membered heteroaryl.

In some embodiments of a compound of Formula (I), (I'), (Ia), or (Ia), Ring A is 6-membered heteroaryl. In some embodiments of a compound of Formula (I), (I'), (Ia), or (Ia'), Ring A is pyridinyl, pyrimidinyl, or pyrazinyl. In some embodiments of a compound of Formula (I), (I'), (Ia), or (Ia'), Ring A is pyrazinyl.

In some embodiments of a compound of Formula (I), (I'), (Ia), or (Ia'), each $R^1$ is independently deuterium, halogen, —CN, —OH, —$OR^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I), (I'), (Ia), or (Ia'), each $R^1$ is independently deuterium, halogen, —CN, —OH, —$OR^a$, $C_1$-$C_6$alkyl, or $C_1$-$C_6$haloalkyl. In some embodiments of a compound of Formula (I), (I'), (Ia), or (Ia'), each $R^1$ is independently —CN.

In some embodiments of a compound of Formula (I), (I'), (Ia), or (Ia'), n is 0 or 1. In some embodiments of a compound of Formula (I), (I'), (Ia), or (Ia'), n is 0-2. In some embodiments of a compound of Formula (I), (I'), (Ia), or (Ia'), n is 1 or 2. In some embodiments of a compound of Formula (I), (I'), (Ia), or (Ia'), n is 1. In some embodiments of a compound of Formula (I), (I'), (Ia), or (Ia'), n is 0. In some embodiments of a compound of Formula (I), (I'), (Ia), or (Ia'), n is 2.

In some embodiments of a compound of Formula (I), (I'), (Ia), or (Ia'), $R^2$ is hydrogen or $C_1$-$C_6$alkyl. In some embodiments of a compound of Formula (I), (I'), (Ia), or (Ia'), $R^2$ is hydrogen.

In some embodiments of a compound of Formula (I), (I'), (Ia), or (Ia'), $R^3$ is hydrogen, deuterium, halogen, $C_1$-$C_6$alkyl, or $C_1$-$C_6$haloalkyl. In some embodiments of a compound of Formula (I), (I'), (Ia), or (Ia'), $R^3$ is hydrogen.

In some embodiments of a compound of Formula (I), (I'), (Ia), or (Ia'), $R^4$ is hydrogen or $C_1$-$C_6$alkyl. In some embodiments of a compound of Formula (I), (I'), (Ia), or (Ia'), $R^4$ is hydrogen.

In some embodiments of a compound of Formula (I), (I'), (Ia), or (Ia'), L is —O—. In some embodiments of a compound of Formula (I), (I'), (Ia), or (Ia'), L is —$NR^6$—.

In some embodiments of a compound of Formula (I), (I'), (Ia), or (Ia'), $R^6$ is hydrogen or $C_1$-$C_6$alkyl. In some embodiments of a compound of Formula (I), (I'), (Ia), or (Ia'), $R^6$ is hydrogen.

In some embodiments of a compound of Formula (I), (I'), (Ia), or (Ia'), $R^6$ is monocyclic cycloalkyl or bicyclic cycloalkyl. In some embodiments of a compound of Formula (I), (I'), (Ia), or (Ia'), $R^6$ is monocyclic cycloalkyl.

In some embodiments of a compound of Formula (I), (I'), (Ia), or (Ia'), $R^6$ is bicyclic cycloalkyl.

In some embodiments of a compound of Formula (I), (I'), (Ia), or (Ia'), $R^6$ is cyclobutyl, cyclopentyl, cyclohexyl, or cycloheptyl. In some embodiments of a compound of Formula (I), (I'), (Ia), or (Ia'), $R^6$ is cyclobutyl. In some embodiments of a compound of Formula (I), (I'), (Ia), or (Ia'), $R^6$ is cyclopentyl. In some embodiments of a compound of Formula (I), (I'), (Ia), or (Ia'), $R^6$ is cyclohexyl. In some embodiments of a compound of Formula (I), (I'), (Ia), or (Ia'), $R^6$ is cycloheptyl.

In some embodiments of a compound of Formula (I), (I'), (Ia), or (Ia'), each $R^7$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; or two $R^7$ on the same atom are taken together to form an oxo. In some embodiments of a compound of Formula (I), (I'), (Ia), or (Ia'), each $R^7$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl; or two $R^7$ on the same atom are taken together to form an oxo. In some embodiments of a compound of Formula (I), (I'), (Ia), or (Ia'), each $R^7$ is independently —$NR^cR^d$, $C_1$-$C_6$alkyl, or $C_1$-$C_6$haloalkyl. In some embodiments of a compound of Formula (I), (I'), (Ia), or (Ia'), each $R^7$ is independently —$NR^cR^d$.

In some embodiments of a compound of Formula (I), (I'), (Ia), or (Ia'), p is 0-7. In some embodiments of a compound of Formula (I), (I'), (Ia), or (Ia'), p is 0-6. In some embodiments of a compound of Formula (I), (I'), (Ia), or (Ia'), p is 0-5. In some embodiments of a compound of Formula (I), (I'), (Ia), or (Ia'), p is 0-4. In some embodiments of a compound of Formula (I), (I'), (Ia), or (Ia'), p is 0-3. In some embodiments of a compound of Formula (I), (I'), (Ia), or (Ia'), p is 1-3. In some embodiments of a compound of Formula (I), (I'), (Ia), or (Ia'), p is 0-2. In some embodiments of a compound of Formula (I), (I'), (Ia), or (Ia'), p is 0 or 1. In some embodiments of a compound of Formula (I), (I'), (Ia), or (Ia'), p is 1 or 2. In some embodiments of a compound of Formula (I), (I'), (Ia), or (Ia'), p is 1. In some embodiments of a compound of Formula (I), (I'), (Ia), or (Ia'), p is 2. In some embodiments of a compound of Formula (I), (I'), (Ia), or (Ia'), p is 0.

In some embodiments of a compound disclosed herein, each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound disclosed herein, each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, or heterocycloalkyl. In some embodiments of a compound disclosed herein, each $R^a$ is independently $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound disclosed herein, each $R^a$ is independently $C_1$-$C_6$alkyl or $C_1$-$C_6$haloalkyl. In some embodiments of a compound disclosed herein, each $R^a$ is independently $C_1$-$C_6$alkyl.

In some embodiments of a compound disclosed herein, each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound disclosed herein, each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, or heterocycloalkyl. In some embodiments of a compound disclosed herein, each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound disclosed herein, each $R^b$ is independently hydrogen, $C_1$-$C_6$alkyl, or $C_1$-$C_6$haloalkyl. In some embodiments of a compound disclosed herein, each $R^b$ is independently hydrogen or $C_1$-$C_6$alkyl. In some embodiments of a compound disclosed herein, each $R^b$ is independently $C_1$-$C_6$alkyl. In some embodiments of a compound disclosed herein, each $R^a$ is hydrogen.

In some embodiments of a compound disclosed herein, each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound disclosed herein, each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, or heterocycloalkyl. In some embodiments of a compound disclosed herein, each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound disclosed herein, each $R^c$ and $R^d$ are independently hydrogen, $C_1$-$C_6$alkyl, or $C_1$-$C_6$haloalkyl. In some embodiments of a compound disclosed herein, each $R^c$ and $R^d$ are independently hydrogen or $C_1$-$C_6$alkyl. In some embodiments of a compound disclosed herein, each $R^c$ and $R^d$ are independently $C_1$-$C_6$alkyl. In some embodiments of a compound disclosed herein, each $R^c$ and $R^d$ are hydrogen.

In some embodiments of a compound disclosed herein, $R^c$ and $R^d$ are taken together with the atom to which they are attached to form a heterocycloalkyl optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound disclosed herein, $R^c$ and $R^d$ are taken together with the atom to which they are attached to form a heterocycloalkyl optionally substituted with one or more oxo, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl.

In some embodiments of a compound disclosed herein, the heterocycloalkyl formed when $R^c$ and $R^d$ are taken together is independently substituted with one, two, three, or four substituents as defined herein. In some embodiments of a compound disclosed herein, the heterocycloalkyl formed when $R^c$ and $R^d$ are taken together is independently substituted with one, two, or three substituents as defined herein. In some embodiments of a compound disclosed herein, the heterocycloalkyl formed when $R^c$ and $R^d$ are taken together is independently substituted with one or two substituents as defined herein. In some embodiments of a compound disclosed herein, the heterocycloalkyl formed when $R^c$ and $R^d$ are taken together is independently substituted with one substituent as defined herein. In some embodiments of a compound disclosed herein, the heterocycloalkyl formed when $R^c$ and $R^d$ are taken together is independently substituted with two substituents as defined herein. In some embodiments of a compound disclosed herein, the heterocycloalkyl formed when $R^c$ and $R^d$ are taken together is independently substituted with three substituents as defined herein.

In some embodiments of a compound disclosed herein, the compound is selected from a compound of Table 1, Table 2, or Table 3:

TABLE 1

| Ex. | Structure | Name |
|---|---|---|
| 1-1 | 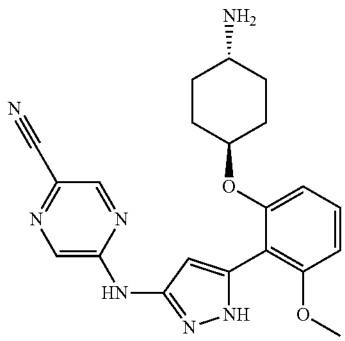 [SMILES: COc1cccc(O[C@H]2CC[C@H](N)CC2)c1-c1cc(Nc2cnc(C#N)cn2)n[nH]1] | 5-((5-(2-(((1r,4r)-4-aminocyclohexyl)oxy)-6-methoxyphenyl)-1H-pyrazol-3-yl)amino)pyrazine-2-carbonitrile |
| 1-4 | 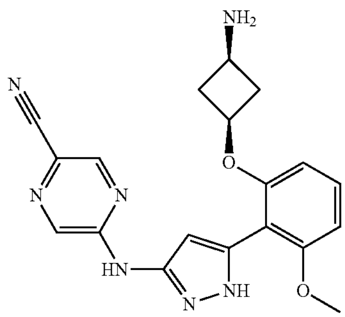 [SMILES: COc1cccc(O[C@H]2C[C@@H](N)C2)c1-c1cc(Nc2cnc(C#N)cn2)n[nH]1] | 5-((5-(2-((1s,3s)-3-aminocyclobutoxy)-6-methoxyphenyl)-1H-pyrazol-3-yl)amino)pyrazine-2-carbonitrile |
| 1-5 | 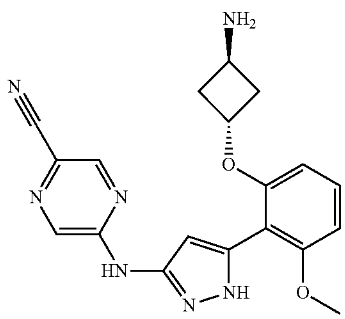 [SMILES: COc1cccc(O[C@H]2C[C@H](N)C2)c1-c1cc(Nc2cnc(C#N)cn2)n[nH]1] | 5-((5-(2-((1r,3r)-3-aminocyclobutoxy)-6-methoxyphenyl)-1H-pyrazol-3-yl)amino)pyrazine-2-carbonitrile |
| 1-6 | 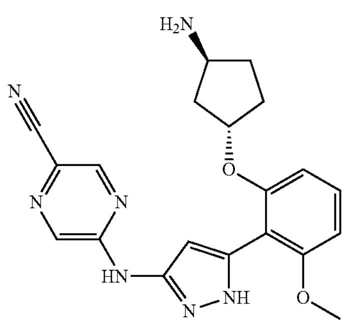 [SMILES: COc1cccc(O[C@H]2CC[C@H](N)C2)c1-c1cc(Nc2cnc(C#N)cn2)n[nH]1] | 5-((5-(2-(((1S,3S)-3-aminocyclopentyl)oxy)-6-methoxyphenyl)-1H-pyrazol-3-yl)amino)pyrazine-2-carbonitrile |
| 1-7 | 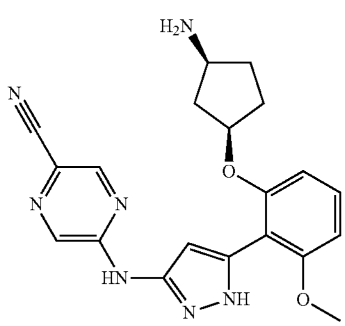 [SMILES: COc1cccc(O[C@@H]2CC[C@H](N)C2)c1-c1cc(Nc2cnc(C#N)cn2)n[nH]1] | 5-((5-(2-(((1R,3S)-3-aminocyclopentyl)oxy)-6-methoxyphenyl)-1H-pyrazol-3-yl)amino)pyrazine-2-carbonitrile |

TABLE 1-continued

| Ex. | Structure | Name |
|---|---|---|
| 1-8 | 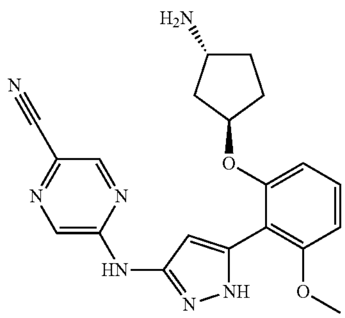 [SMILES: COc1cccc(O[C@@H]2CC[C@@H](N)C2)c1-c1cc(Nc2cnc(C#N)cn2)n[nH]1] | 5-((5-(2-(((1R,3R)-3-aminocyclopentyl)oxy)-6-methoxyphenyl)-1H-pyrazol-3-yl)amino)pyrazine-2-carbonitrile |
| 1-9 | 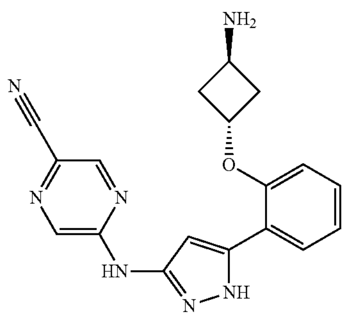 [SMILES: N#Cc1cnc(Nc2cc(-c3ccccc3O[C@H]3C[C@H](N)C3)[nH]n2)cn1] | 5-((5-(2-((1r,3r)-3-aminocyclobutoxy)phenyl)-1H-pyrazol-3-yl)amino)pyrazine-2-carbonitrile |
| 1-10 | 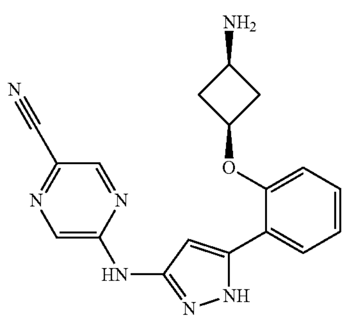 [SMILES: N#Cc1cnc(Nc2cc(-c3ccccc3O[C@H]3C[C@@H](N)C3)[nH]n2)cn1] | 5-((5-(2-((1s,3s)-3-aminocyclobutoxy)phenyl)-1H-pyrazol-3-yl)amino)pyrazine-2-carbonitrile |
| 1-11 | 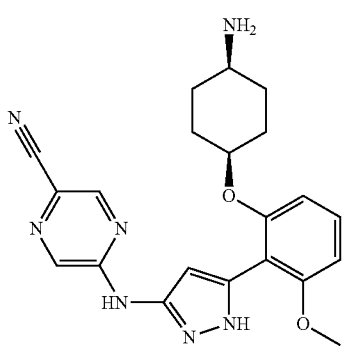 [SMILES: COc1cccc(O[C@H]2CC[C@@H](N)CC2)c1-c1cc(Nc2cnc(C#N)cn2)n[nH]1] | 5-((5-(2-(((1s,4s)-4-aminocyclohexyl)oxy)-6-methoxyphenyl)-1H-pyrazol-3-yl)amino)pyrazine-2-carbonitrile |

TABLE 1-continued

| Ex. | Structure | Name |
|---|---|---|
| 1-12 | 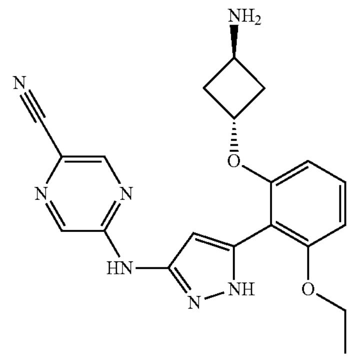 [SMILES: CCOc1cccc(O[C@H]2C[C@H](N)C2)c1-c1cc(Nc2cnc(C#N)cn2)n[nH]1] | 5-((5-(2-((1r,3r)-3-aminocyclobutoxy)-6-ethoxyphenyl)-1H-pyrazol-3-yl)amino)pyrazine-2-carbonitrile |
| 1-13 | 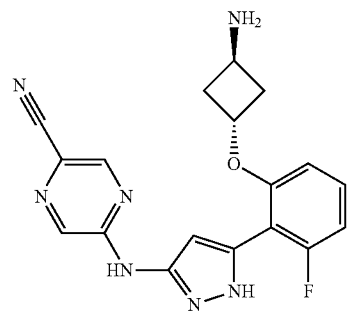 [SMILES: N#Cc1cnc(Nc2cc(-c3c(F)cccc3O[C@H]3C[C@H](N)C3)[nH]n2)cn1] | 5-((5-(2-((1r,3r)-3-aminocyclobutoxy)-6-fluorophenyl)-1H-pyrazol-3-yl)amino)pyrazine-2-carbonitrile |
| 1-14 | 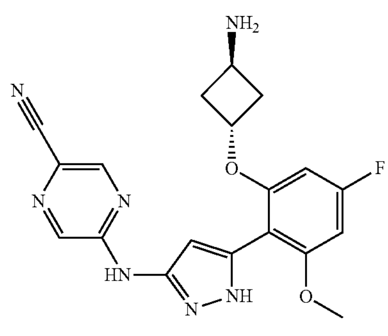 [SMILES: COc1cc(F)cc(O[C@H]2C[C@H](N)C2)c1-c1cc(Nc2cnc(C#N)cn2)n[nH]1] | 5-((5-(2-((1r,3r)-3-aminocyclobutoxy)-4-fluoro-6-methoxyphenyl)-1H-pyrazol-3-yl)amino)pyrazine-2-carbonitrile |
| 1-15 | 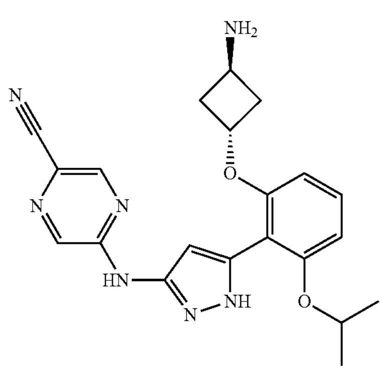 [SMILES: CC(C)Oc1cccc(O[C@H]2C[C@H](N)C2)c1-c1cc(Nc2cnc(C#N)cn2)n[nH]1] | 5-((5-(2-((1r,3r)-3-aminocyclobutoxy)-6-isopropoxyphenyl)-1H-pyrazol-3-yl)amino)pyrazine-2-carbonitrile |

TABLE 1-continued

| Ex. | Structure | Name |
|---|---|---|
| 1-16 | 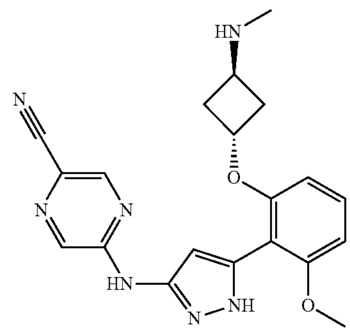 [SMILES: CN[C@H]1C[C@H](Oc2cccc(OC)c2-c2cc(Nc3cnc(C#N)cn3)n[nH]2)C1] | 5-((5-(2-methoxy-6-((1r,3r)-3-(methylamino)cyclobutoxy)phenyl)-1H-pyrazol-3-yl)amino)pyrazine-2-carbonitrile |
| 1-17 | 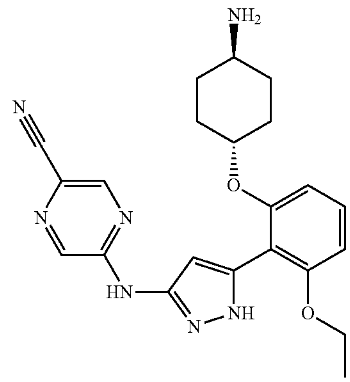 [SMILES: CCOc1cccc(O[C@H]2CC[C@H](N)CC2)c1-c1cc(Nc2cnc(C#N)cn2)n[nH]1] | 5-((5-(2-(((1r,4r)-4-aminocyclohexyl)oxy)-6-ethoxyphenyl)-1H-pyrazol-3-yl)amino)pyrazine-2-carbonitrile |
| 1-18 | 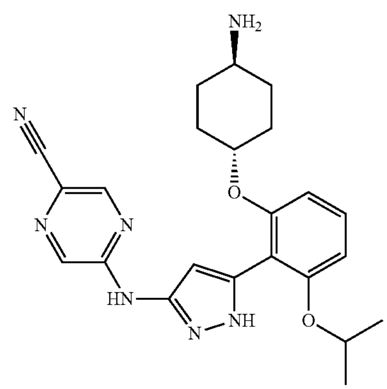 [SMILES: CC(C)Oc1cccc(O[C@H]2CC[C@H](N)CC2)c1-c1cc(Nc2cnc(C#N)cn2)n[nH]1] | 5-((5-(2-(((1r,4r)-4-aminocyclohexyl)oxy)-6-isopropoxyphenyl)-1H-pyrazol-3-yl)amino)pyrazine-2-carbonitrile |
| 1-19 | 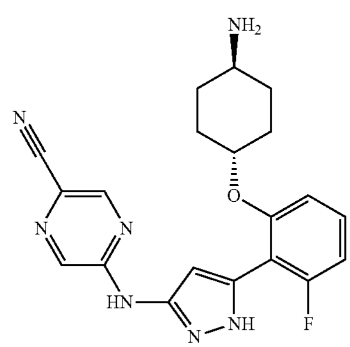 [SMILES: N#Cc1cnc(Nc2cc(-c3c(F)cccc3O[C@H]3CC[C@H](N)CC3)[nH]n2)cn1] | 5-((5-(2-(((1r,4r)-4-aminocyclohexyl)oxy)-6-fluorophenyl)-1H-pyrazol-3-yl)amino)pyrazine-2-carbonitrile |

TABLE 1-continued

| Ex. | Structure | Name |
|---|---|---|
| 1-20 | 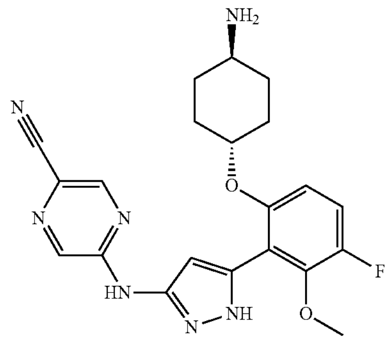 [SMILES: COc1c(F)ccc(O[C@H]2CC[C@H](N)CC2)c1-c1cc(Nc2cnc(C#N)cn2)n[nH]1] | 5-((5-(6-(((1r,4r)-4-aminocyclohexyl)oxy)-3-fluoro-2-methoxyphenyl)-1H-pyrazol-3-yl)amino)pyrazine-2-carbonitrile |
| 1-21 | 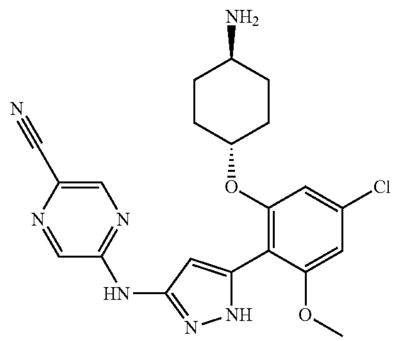 [SMILES: COc1cc(Cl)cc(O[C@H]2CC[C@H](N)CC2)c1-c1cc(Nc2cnc(C#N)cn2)n[nH]1] | 5-((5-(2-(((1r,4r)-4-aminocyclohexyl)oxy)-4-chloro-6-methoxyphenyl)-1H-pyrazol-3-yl)amino)pyrazine-2-carbonitrile |
| 1-22 | 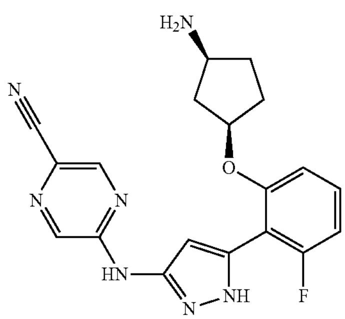 [SMILES: N#Cc1cnc(Nc2cc(-c3c(F)cccc3O[C@@H]3CC[C@H](N)C3)[nH]n2)cn1] | 5-((5-(2-(((1R,3S)-3-aminocyclopentyl)oxy)-6-fluorophenyl)-1H-pyrazol-3-yl)amino)pyrazine-2-carbonitrile |
| 1-23 | 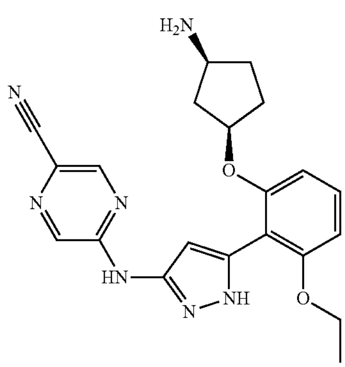 [SMILES: CCOc1cccc(O[C@@H]2CC[C@H](N)C2)c1-c1cc(Nc2cnc(C#N)cn2)n[nH]1] | 5-((5-(2-(((1R,3S)-3-aminocyclopentyl)oxy)-6-ethoxyphenyl)-1H-pyrazol-3-yl)amino)pyazine-2-carbonitrile |

TABLE 1-continued

| Ex. | Structure | Name |
|---|---|---|
| 1-24 | 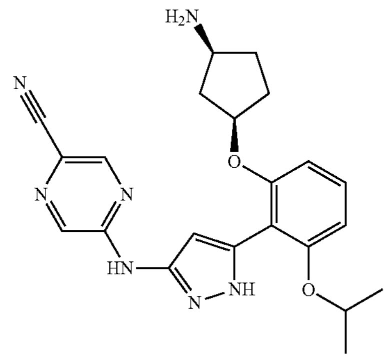 [SMILES: CC(C)Oc1cccc(O[C@@H]2CC[C@H](N)C2)c1-c1cc(Nc2cnc(C#N)cn2)n[nH]1] | 5-((5-(2-(((1R,3S)-3-aminocyclopentyl)oxy)-6-isopropoxyphenyl)-1H-pyrazol-3-yl)amino)pyrazine-2-carbonitrile |
| 1-25 | 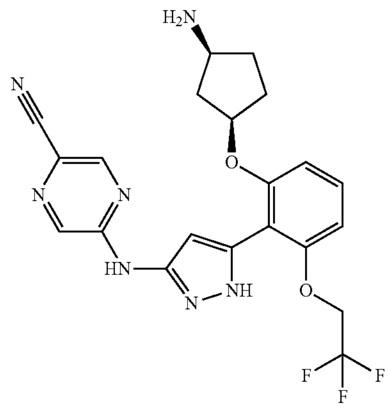 [SMILES: N#Cc1cnc(Nc2cc(-c3c(OCC(F)(F)F)cccc3O[C@@H]3CC[C@H](N)C3)[nH]n2)cn1] | 5-((5-(2-(((1R,3S)-3-aminocyclopentyl)oxy)-6-(2,2,2-trifluoroethoxy)phenyl)-1-pyrazol-3-yl)amino)pyrazine-2-carbonitrile |
| 1-26 | 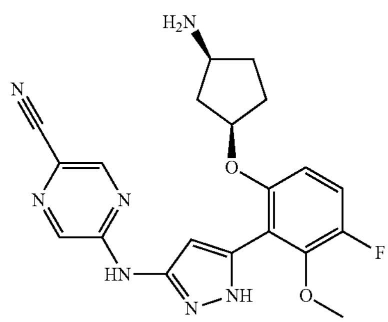 [SMILES: COc1c(F)ccc(O[C@@H]2CC[C@H](N)C2)c1-c1cc(Nc2cnc(C#N)cn2)n[nH]1] | 5-((5-(6-(((1R,3S)-3-aminocyclopentyl)oxy)-3-fluoro-2-methoxyphenyl)-1H-pyrazol-3-yl)amino)pyrazine-2-carbonitrile |
| 1-27 | 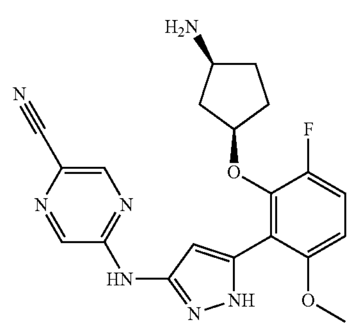 [SMILES: COc1ccc(F)c(O[C@@H]2CC[C@H](N)C2)c1-c1cc(Nc2cnc(C#N)cn2)n[nH]1] | 5-((5-(2-(((1R,3S)-3-aminocyclopentyl)oxy)-3-fluoro-6-methoxyphenyl)-1H-pyrazol-3-yl)amino)pyrazine-2-carbonitrile |

TABLE 1-continued

| Ex. | Structure | Name |
|---|---|---|
| 1-28 | 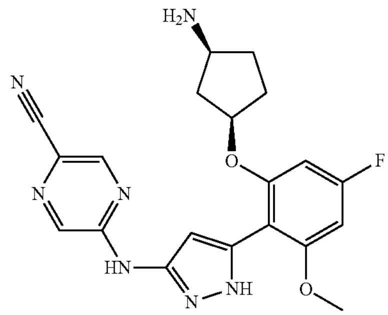 [SMILES: COc1cc(F)cc(O[C@@H]2CC[C@H](N)C2)c1-c1cc(Nc2cnc(C#N)cn2)n[nH]1] | 5-((5-(2-(((1R,3S)-3-aminocyclopentyl)oxy)-4-fluoro-6-methoxyphenyl)-1H-pyrazol-3-yl)amino)pyrazine-2-carbonitrile |
| 1-29 | 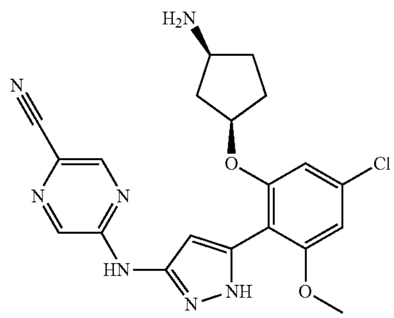 [SMILES: COc1cc(Cl)cc(O[C@@H]2CC[C@H](N)C2)c1-c1cc(Nc2cnc(C#N)cn2)n[nH]1] | 5-((5-(2-(((1R,3S)-3-aminocyclopentyl)oxy)-4-chloro-6-methoxyphenyl)-1H-pyrazol-3-yl)amino)pyrazine-2-carbonitrile |
| 1-30 | 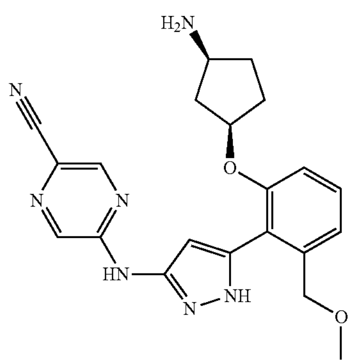 [SMILES: COCc1cccc(O[C@@H]2CC[C@H](N)C2)c1-c1cc(Nc2cnc(C#N)cn2)n[nH]1] | 5-((5-(2-(((1R,3S)-3-aminocyclopentyl)oxy)-6-(methoxymethyl)phenyl)-1H-pyrazol-3-yl)amino)pyrazine-2-carbonitrile |
| 1-31 | 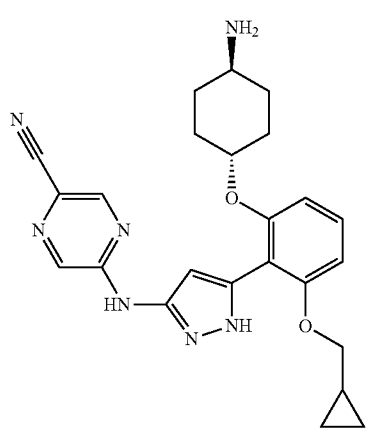 [SMILES: N#Cc1cnc(Nc2cc(-c3c(OCC4CC4)cccc3O[C@H]3CC[C@H](N)CC3)[nH]n2)cn1] | 5-((5-(2-(((1r,4r)-4-aminocyclohexyl)oxy)-6-(cyclopropylmethoxy)phenyl)-1H-pyrazol-3-yl)amino)pyrazine-2-carbonitrile |

TABLE 1-continued

| Ex. | Structure | Name |
|---|---|---|
| 1-32 | 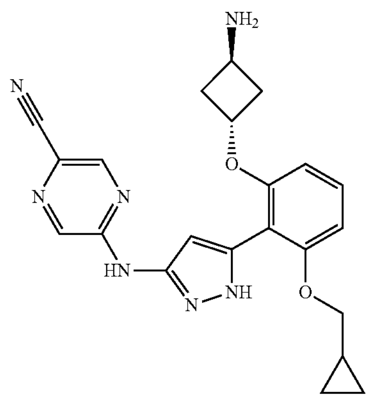 [SMILES: N#Cc1cnc(Nc2cc(-c3c(OCC4CC4)cccc3O[C@H]3C[C@H](N)C3)[nH]n2)cn1] | 5-((5-(2-((1r,3r)-3-aminocyclobutoxy)-6-(cyclopropylmethoxy)phenyl)-1H-pyrazol-3-yl)amino)pyrazine-2-carbonitrile |
| 1-33 | 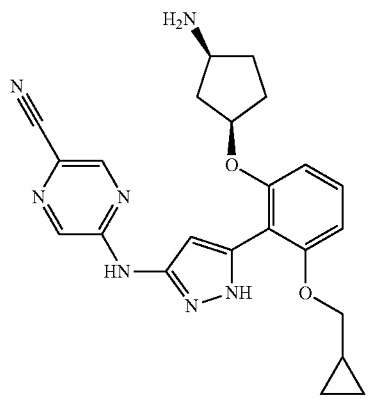 [SMILES: N#Cc1cnc(Nc2cc(-c3c(OCC4CC4)cccc3O[C@@H]3CC[C@H](N)C3)[nH]n2)cn1] | 5-((5-(2-(((1R,3S)-3-aminocyclopentyl)oxy)-6-(cyclopropylmethoxy)phenyl)-1H-pyrazol-3-yl)amino)pyrazine-2-carbonitrile |
| 1-34 | 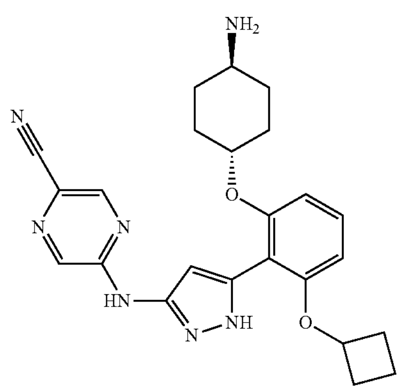 [SMILES: N#Cc1cnc(Nc2cc(-c3c(OC4CCC4)cccc3O[C@H]3CC[C@H](N)CC3)[nH]n2)cn1] | 5-((5-(2-(((1r,4r)-4-aminocyclohexyl)oxy)-6-cyclobutoxyphenyl)-1H-pyrazol-3-yl)amino)pyrazine-2-carbonitrile |
| 1-35 | 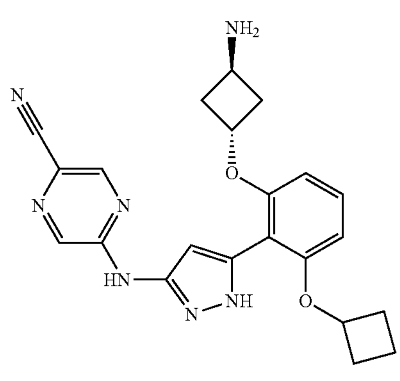 [SMILES: N#Cc1cnc(Nc2cc(-c3c(OC4CCC4)cccc3O[C@H]3C[C@H](N)C3)[nH]n2)cn1] | 5-((5-(2-((1r,3r)-3-aminocyclobutoxy)-6-cyclobutoxyphenyl)-1H-pyrazol-3-yl)amino)pyrazine-2-carbonitrile |

TABLE 1-continued

| Ex. | Structure | Name |
|---|---|---|
| 1-36 | 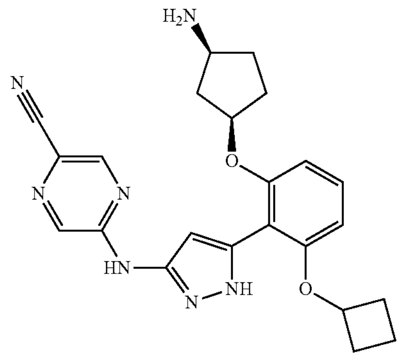 [SMILES: N#Cc1cnc(Nc2cc(-c3c(OC4CCC4)cccc3O[C@@H]3CC[C@H](N)C3)[nH]n2)cn1] | 5-((5-(2-(((1R,3S)-3-aminocyclopentyl)oxy)-6-cyclobutoxyphenyl)-1H-pyrazol-3-yl)amino)pyrazine-2-carbonitrile |
| 1-37 | 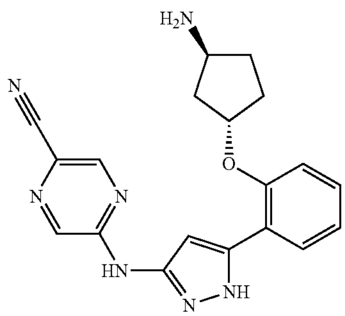 [SMILES: N#Cc1cnc(Nc2cc(-c3ccccc3O[C@H]3CC[C@H](N)C3)[nH]n2)cn1] | 5-((5-(2-(((1R,3R)-3-aminocyclopentyl)oxy)phenyl)-1H-pyrazol-3-yl)amino)pyrazine-2-carbonitrile |
| 1-38 | 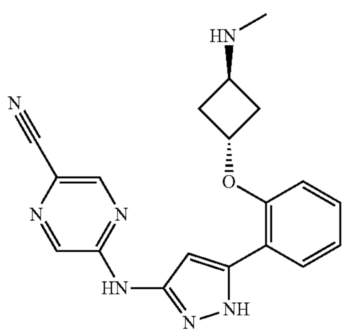 [SMILES: CN[C@H]1C[C@H](Oc2ccccc2-c2cc(Nc3cnc(C#N)cn3)n[nH]2)C1] | 5-((5-(2-((1r,3r)-3-(methylamino)cyclobutoxy)phenyl)-1H-pyrazol-3-yl)amino)pyrazine-2-carbonitrile |
| 1-39 | 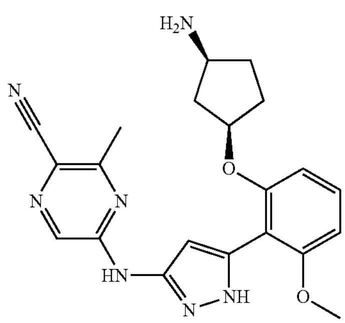 [SMILES: COc1cccc(O[C@@H]2CC[C@H](N)C2)c1-c1cc(Nc2cnc(C#N)c(C)n2)n[nH]1] | 5-((5-(2-(((1R,3S)-3-aminocyclopentyl)oxy)-6-methoxyphenyl)-1H-pyrazol-3-yl)amino)-3-methylpyrazine-2-carbonitrile |

TABLE 1-continued

| Ex. | Structure | Name |
|---|---|---|
| 1-40 | 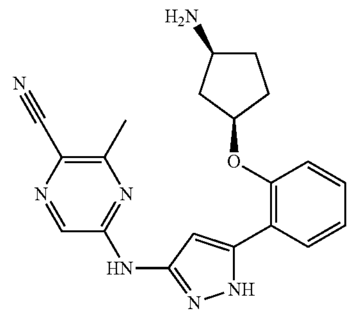 [SMILES: Cc1nc(Nc2cc(-c3ccccc3O[C@@H]3CC[C@H](N)C3)[nH]n2)cnc1C#N] | 5-((5-(2-((((1R,3S)-3-aminocyclopentyl)oxy)phenyl)-1H-pyrazol-3-yl)amino)-3-methylpyrazine-2-carbonitrile |
| 1-41 | 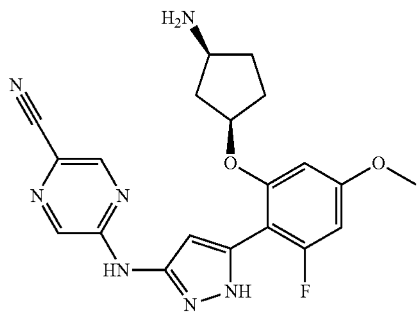 [SMILES: COc1cc(F)c(-c2cc(Nc3cnc(C#N)cn3)n[nH]2)c(O[C@@H]2CC[C@H](N)C2)c1] | 5-((5-(2-((((1R,3S)-3-aminocyclopentyl)oxy)-6-fluoro-4-methoxyphenyl)-1H-pyrazol-3-yl)amino)pyrazine-2-carbonitrile |
| 1-42 | 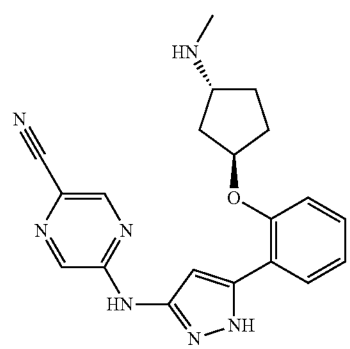 [SMILES: CN[C@@H]1CC[C@@H](Oc2ccccc2-c2cc(Nc3cnc(C#N)cn3)n[nH]2)C1] | 5-((5-(2-((((1R,3R)-3-(methylamino)cyclopentyl)oxy)phenyl)-1H-pyrazol-3-yl)amino)pyrazine-2-carbonitrile |
| 1-43 | 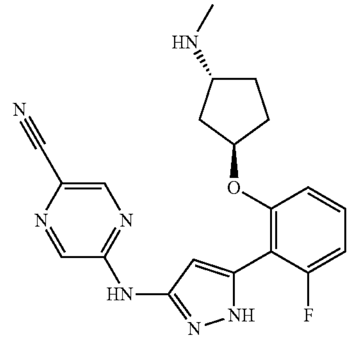 [SMILES: CN[C@@H]1CC[C@@H](Oc2cccc(F)c2-c2cc(Nc3cnc(C#N)cn3)n[nH]2)C1] | 5-((5-(2-fluoro-6-((((1R,3R)-3-(methylamino)cyclopentyl)oxy)phenyl)-1H-pyrazol-3-yl)amino)pyrazine-2-carbonitrile |

TABLE 1-continued

| Ex. | Structure | Name |
|---|---|---|
| 1-44 | 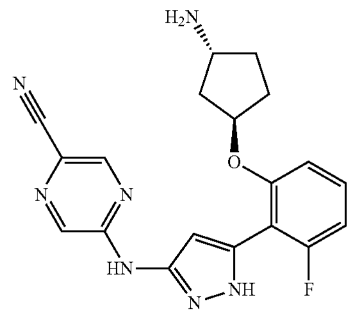 [SMILES: N#Cc1cnc(Nc2cc(-c3c(F)cccc3O[C@@H]3CC[C@@H](N)C3)[nH]n2)cn1] | 5-((5-(2-((((1R,3R)-3-aminocyclopentyl)oxy)-6-fluorophenyl)-1H-pyrazol-3-yl)amino)pyrazine-2-carbonitrile |
| 1-45 | 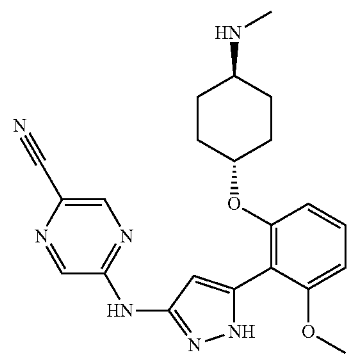 [SMILES: CN[C@H]1CC[C@H](Oc2cccc(OC)c2-c2cc(Nc3cnc(C#N)cn3)n[nH]2)CC1] | 5-((5-(2-methoxy-6-((((1r,4r)-4-(methylamino)cyclohexyl)oxy)phenyl)-1H-pyrazol-3-yl)amino)pyrazine-2-carbonitrile |
| 1-46 | 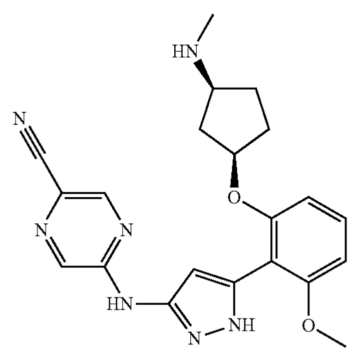 [SMILES: CN[C@H]1CC[C@@H](Oc2cccc(OC)c2-c2cc(Nc3cnc(C#N)cn3)n[nH]2)C1] | 5-((5-(2-methoxy-6-((((1R,3S)-3-(methylamino)cyclopentyl)oxy)phenyl)-1H-pyrazol-3-yl)amino)pyrazine-2-carbonitrile |
| 1-47 | 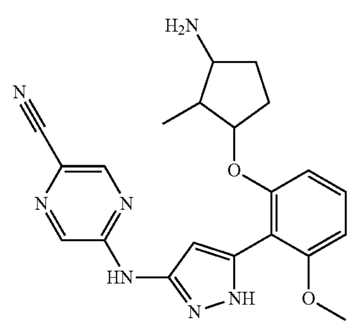 [SMILES: COc1cccc(OC2CCC(N)C2C)c1-c1cc(Nc2cnc(C#N)cn2)n[nH]1] | 5-((5-(2-((3-amino-2-methylcyclopentyl)oxy)-6-methoxyphenyl)-1H-pyrazol-3-yl)amino)pyrazine-2-carbonitrile |

TABLE 1-continued

| Ex. | Structure | Name |
|---|---|---|
| 1-48 | 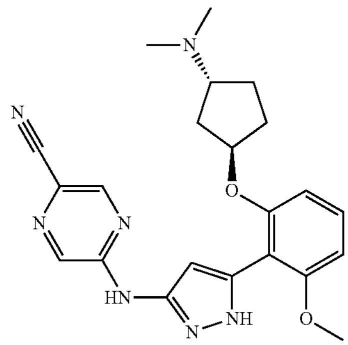 [SMILES: COc1cccc(O[C@@H]2CC[C@@H](N(C)C)C2)c1-c1cc(Nc2cnc(C#N)cn2)n[nH]1] | 5-((5-(2-(((1R,3R)-3-(dimethylamino)cyclopentyl)oxy)-6-methoxyphenyl)-1H-pyrazol-3-yl)amino)pyrazine-2-carbonitrile |
| 1-49 | 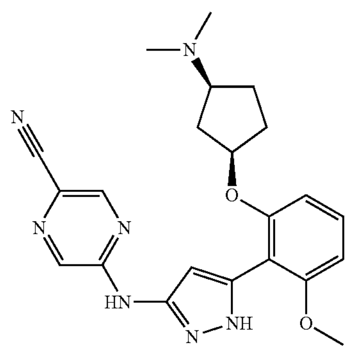 [SMILES: COc1cccc(O[C@@H]2CC[C@H](N(C)C)C2)c1-c1cc(Nc2cnc(C#N)cn2)n[nH]1] | 5-((5-(2-(((1R,3S)-3-(dimethylamino)cyclopentyl)oxy)-6-methoxyphenyl)-1H-pyrazol-3-yl)amino)pyrazine-2-carbonitrile |
| 1-50 | 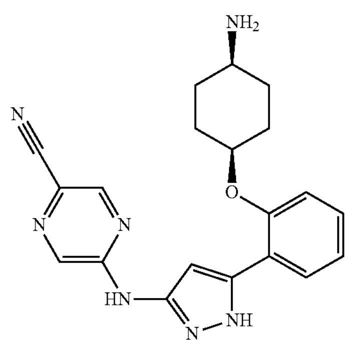 [SMILES: N#Cc1cnc(Nc2cc(-c3ccccc3O[C@H]3CC[C@@H](N)CC3)[nH]n2)cn1] | 5-((5-(2-(((1s,4s)-4-aminocyclohexyl)oxy)phenyl)-1H-pyrazol-3-yl)amino)pyrazine-2-carbonitrile |
| 1-51 | 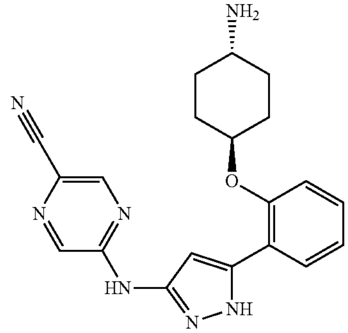 [SMILES: N#Cc1cnc(Nc2cc(-c3ccccc3O[C@H]3CC[C@H](N)CC3)[nH]n2)cn1] | 5-((5-(2-(((1r,4r)-4-aminocyclohexyl)oxy)phenyl)-1H-pyrazol-3-yl)amino)pyrazine-2-carbonitrile |

TABLE 1-continued

| Ex. | Structure | Name |
|---|---|---|
| 1-52 | 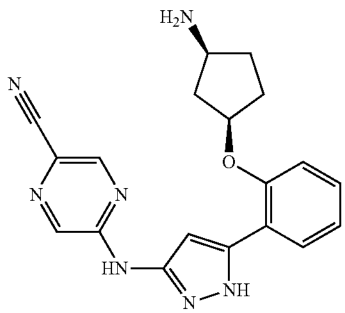 [SMILES: N#Cc1cnc(Nc2cc(-c3ccccc3O[C@@H]3CC[C@H](N)C3)[nH]n2)cn1] | 5-((5-(2-(((1R,3S)-3-aminocyclopentyl)oxy)phenyl)-1H-pyrazol-3-yl)amino)pyrazine-2-carbonitrile |
| 1-53 | 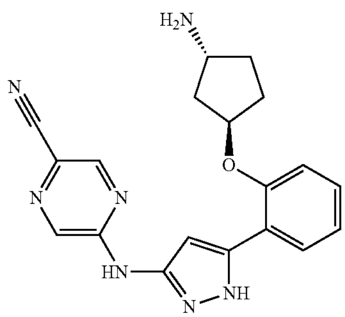 [SMILES: N#Cc1cnc(Nc2cc(-c3ccccc3O[C@@H]3CC[C@@H](N)C3)[nH]n2)cn1] | 5-((5-(2-(((1R,3R)-3-aminocyclopentyl)oxy)phenyl)-1H-pyrazol-3-yl)amino)pyrazine-2-carbonitrile |
| 1-54 | 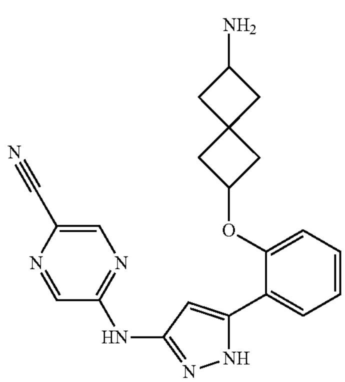 [SMILES: N#Cc1cnc(Nc2cc(-c3ccccc3OC3CC4(CC(N)C4)C3)[nH]n2)cn1] | 5-((5-(2-((6-aminospiro[3.3]heptan-2-yl)oxy)phenyl)-1H-pyrazol-3-yl)amino)pyrazine-2-carbonitrile |
| 1-55 | 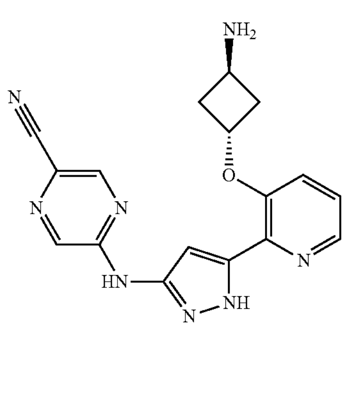 [SMILES: N#Cc1cnc(Nc2cc(-c3ncccc3O[C@H]3C[C@H](N)C3)[nH]n2)cn1] | 5-((5-(3-((1r,3r)-3-aminocyclobutoxy)pyridin-2-yl)-1H-pyrazol-3-yl)amino)pyrazine-2-carbonitrile |

TABLE 1-continued

| Ex. | Structure | Name |
|---|---|---|
| 1-56 | 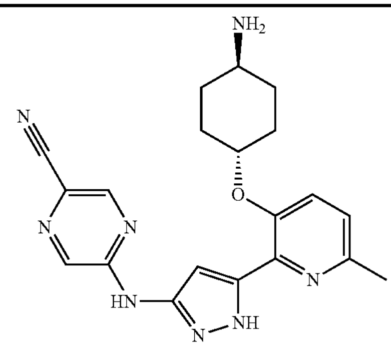 | 5-((5-(3-(((1r,4r)-4-aminocyclohexyl)oxy)-6-methylpyridin-2-yl)-1H-pyrazol-3-yl)amino)pyrazine-2-carbonitrile |
| 1-57 | 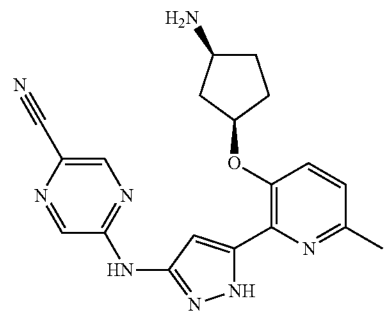 [SMILES: Cc1ccc(O[C@@H]2CC[C@H](N)C2)c(-c2cc(Nc3cnc(C#N)cn3)n[nH]2)n1] | 5-((5-(3-(((1R,3S)-3-aminocyclopentyl)oxy)-6-methylpyridin-2-yl)-1H-pyrazol-3-yl)amino)pyrazine-2-carbonitrile |
| 1-58 | 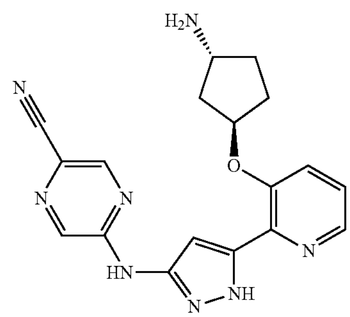 [SMILES: N#Cc1cnc(Nc2cc(-c3ncccc3O[C@@H]3CC[C@@H](N)C3)[nH]n2)cn1] | 5-((5-(3-(((1R,3R)-3-aminocyclopentyl)oxy)pyridin-2-yl)-1H-pyrazol-3-yl)amino)pyrazine-2-carbonitrile |
| 1-59 | 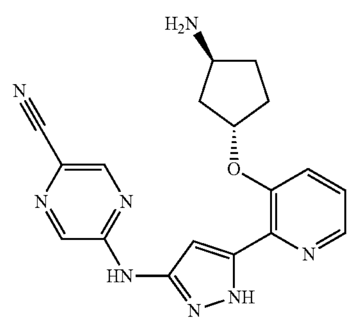 | 5-((5-(3-(((1R,3R)-3-aminocyclopentyl)oxy)pyridin-2-yl)-1H-pyrazol-3-yl)amino)pyrazine-2-carbonitrile |
| 1-60 | 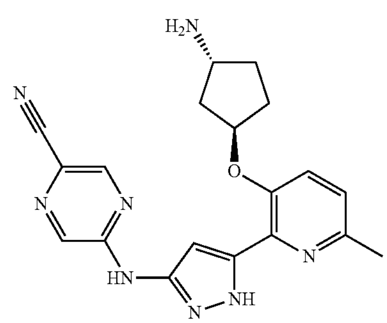 [SMILES: Cc1ccc(O[C@@H]2CC[C@@H](N)C2)c(-c2cc(Nc3cnc(C#N)cn3)n[nH]2)n1] | 5-((5-(3-(((1R,3R)-3-aminocyclopentyl)oxy)-6-methylpyridin-2-yl)-1H-pyrazol-3-yl)amino)pyrazine-2-carbonitrile |

TABLE 1-continued

| Ex. | Structure | Name |
|---|---|---|
| 1-61 | 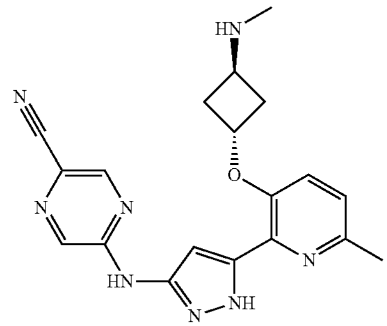 [SMILES: CN[C@H]1C[C@H](Oc2ccc(C)nc2-c2cc(Nc3cnc(C#N)cn3)n[nH]2)C1] | 5-((5-(6-methyl-3-((1r,3r)-3-(methylamino)cyclobutoxy)pyridin-2-yl)-1H-pyrazol-3-yl)amino)pyrazine-2-carbonitrile |
| 1-62 | 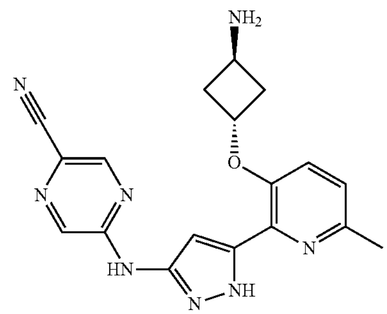 [SMILES: Cc1ccc(O[C@H]2C[C@H](N)C2)c(-c2cc(Nc3cnc(C#N)cn3)n[nH]2)n1] | 5-((5-(3-((1r,3r)-3-aminocyclobutoxy)-6-methylpyridin-2-yl)-1H-pyrazol-3-yl)amino)pyrazine-2-carbonitrile |
| 1-63 | 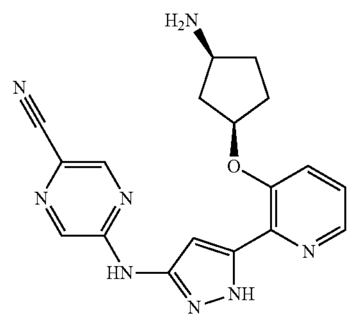 [SMILES: N#Cc1cnc(Nc2cc(-c3ncccc3O[C@@H]3CC[C@H](N)C3)[nH]n2)cn1] | 5-((5-(3-(((1R,3S)-3-aminocyclopentyl)oxy)pyridin-2-yl)-1H-pyrazol-3-yl)amino)pyrazine-2-carbonitrile |
| 1-64 | 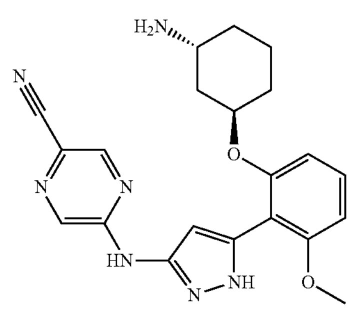 [SMILES: COc1cccc(O[C@@H]2CCC[C@@H](N)C2)c1-c1cc(Nc2cnc(C#N)cn2)n[nH]1] | 5-((5-(2-(((1R,3R)-3-aminocyclohexyl)oxy)-6-methoxyphenyl)-1H-pyrazol-3-yl)amino)pyrazine-2-carbonitrile |
| 1-65 | 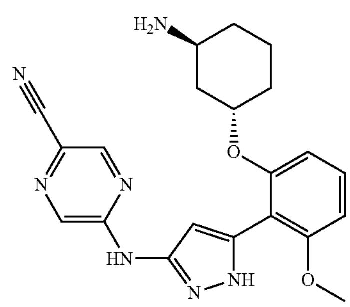 [SMILES: COc1cccc(O[C@H]2CCC[C@H](N)C2)c1-c1cc(Nc2cnc(C#N)cn2)n[nH]1] | 5-[[5-[2-[(1S,3S)-3-aminocyclohexoxy]-6-methoxy-phenyl]-1H-pyrazol-3-yl]amino]pyrazine-2-carbonitrile |

TABLE 1-continued

| Ex. | Structure | Name |
|---|---|---|
| 1-66 | 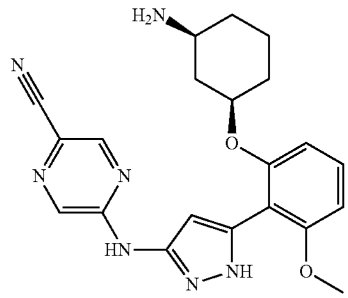 [SMILES: COc1cccc(O[C@@H]2CCC[C@H](N)C2)c1-c1cc(Nc2cnc(C#N)cn2)n[nH]1] | 5-[[5-[2-methoxy-6-[cis-3-aminocyclohexoxy]phenyl]-1H-pyrazol-3-yl]amino]pyrazine-2-carbonitrile |
| 2-1 | 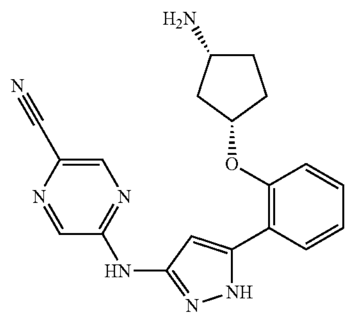 [SMILES: N#Cc1cnc(Nc2cc(-c3ccccc3O[C@H]3CC[C@@H](N)C3)[nH]n2)cn1] | 5-((5-(2-(((1S,3R)-3-aminocyclopentyl)oxy)phenyl)-1H-pyrazol-3-yl)amino)pyrazine-2-carbonitrile |
| 2-2 | 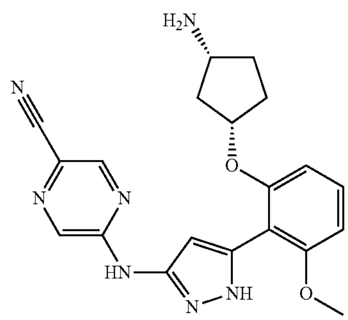 [SMILES: COc1cccc(O[C@H]2CC[C@@H](N)C2)c1-c1cc(Nc2cnc(C#N)cn2)n[nH]1] | 5-((5-(2-(((1S,3R)-3-aminocyclopentyl)oxy)-6-methoxyphenyl)-1H-pyrazol-3-yl)amino)pyrazine-2-carbonitrile |
| 2-3 | 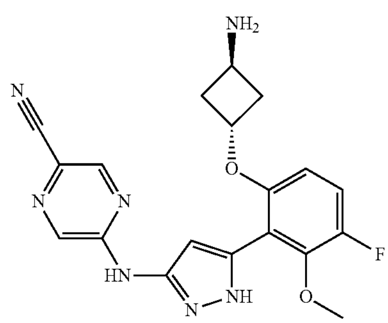 [SMILES: COc1c(F)ccc(O[C@H]2C[C@H](N)C2)c1-c1cc(Nc2cnc(C#N)cn2)n[nH]1] | 5-((5-(6-((1r,3r)-3-aminocyclobutoxy)-3-fluoro-2-methoxyphenyl)-1H-pyrazol-3-yl)amino)pyrazine-2-carbonitrile |
| 2-4 | 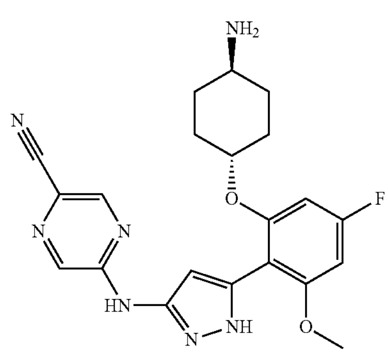 [SMILES: COc1cc(F)cc(O[C@H]2CC[C@H](N)CC2)c1-c1cc(Nc2cnc(C#N)cn2)n[nH]1] | 5-((5-(2-(((1r,4r)-4-aminocyclohexyl)oxy)-4-fluoro-6-methoxyphenyl)-1H-pyrazol-3-yl)amino)pyrazine-2-carbonitrile |

TABLE 1-continued

| Ex. | Structure | Name |
|---|---|---|
| 2-5 | 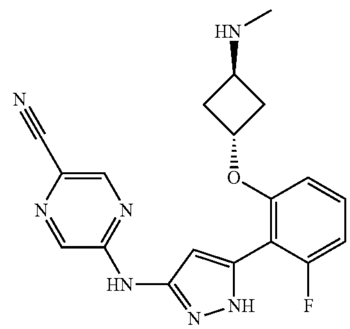 [SMILES: CN[C@H]1C[C@H](Oc2cccc(F)c2-c2cc(Nc3cnc(C#N)cn3)n[nH]2)C1] | 5-((5-(2-fluoro-6-((1r,3r)-3-(methylamino)cyclobutoxy)phenyl)-1H-pyrazol-3-yl)amino)pyrazine-2-carbonitrile |
| 3-1 | 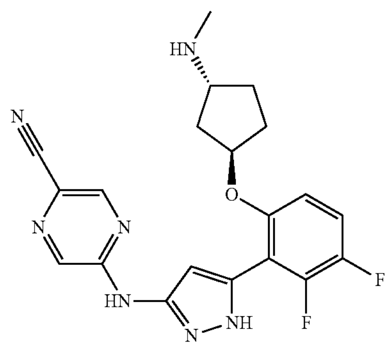 [SMILES: CN[C@@H]1CC[C@@H](Oc2ccc(F)c(F)c2-c2cc(Nc3cnc(C#N)cn3)n[nH]2)C1] | 5-((5-(2,3-difluoro-6-(((1R,3R)-3-(methylamino)cyclopentyl)oxy)phenyl)-1H-pyrazol-3-yl)amino)pyrazine-2-carbonitrile |
| 3-2 | 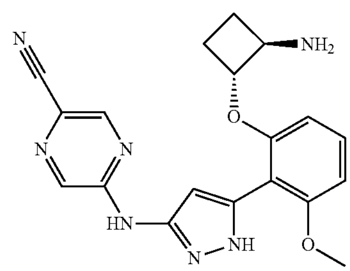 [SMILES: COc1cccc(O[C@@H]2CC[C@H]2N)c1-c1cc(Nc2cnc(C#N)cn2)n[nH]1] | 5-((5-(2-((1R,2R)-2-aminocyclobutoxy)-6-methoxyphenyl)-1H-pyrazol-3-yl)amino)pyrazine-2-carbonitrile |
| 3-3 | 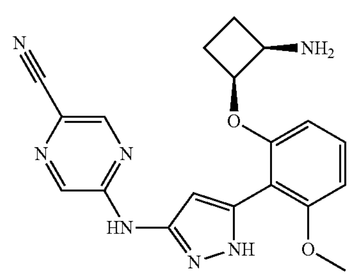 [SMILES: COc1cccc(O[C@H]2CC[C@H]2N)c1-c1cc(Nc2cnc(C#N)cn2)n[nH]1] | 5-((5-(2-((1S,2R)-2-aminocyclobutoxy)-6-methoxyphenyl)-1H-pyrazol-3-yl)amino)pyrazine-2-carbonitrile |
| 3-4 | 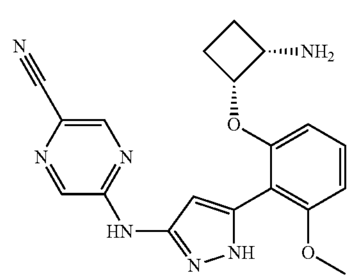 [SMILES: COc1cccc(O[C@@H]2CC[C@@H]2N)c1-c1cc(Nc2cnc(C#N)cn2)n[nH]1] | 5-((5-(2-((1R,2S)-2-aminocyclobutoxy)-6-methoxyphenyl)-1H-pyrazol-3-yl)amino)pyrazine-2-carbonitrile |

TABLE 1-continued

| Ex. | Structure | Name |
|---|---|---|
| 3-5 | 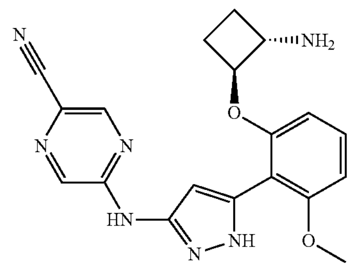 [SMILES: COc1cccc(O[C@H]2CC[C@@H]2N)c1-c1cc(Nc2cnc(C#N)cn2)n[nH]1] | 5-((5-(2-(((1S,2S)-2-aminocyclobutoxy)-6-methoxyphenyl)-1H-pyrazol-3-yl)amino)pyrazine-2-carbonitrile |
| 3-6 | 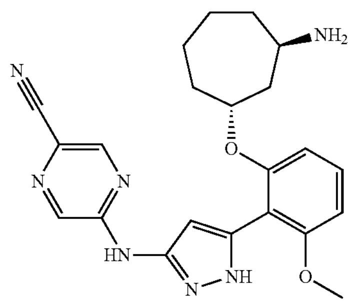 [SMILES: COc1cccc(O[C@@H]2CCCC[C@@H](N)C2)c1-c1cc(Nc2cnc(C#N)cn2)n[nH]1] | 5-((5-(2-(((1R,3R)-3-aminocycloheptyl)oxy)-6-methoxyphenyl)-1H-pyrazol-3-yl)amino)pyrazine-2-carbonitrile |
| 3-7 | 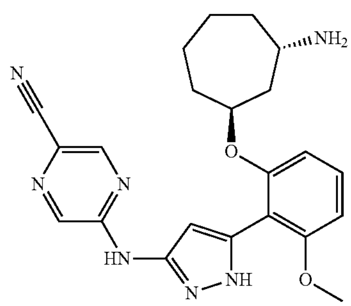 [SMILES: COc1cccc(O[C@H]2CCCC[C@H](N)C2)c1-c1cc(Nc2cnc(C#N)cn2)n[nH]1] | 5-((5-(2-(((1S,3S)-3-aminocycloheptyl)oxy)-6-methoxyphenyl)-1H-pyrazol-3-yl)amino)pyrazine-2-carbonitrile |
| 3-8 | 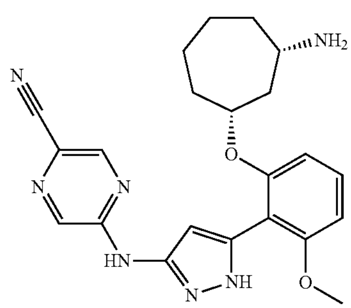 [SMILES: COc1cccc(O[C@@H]2CCCC[C@H](N)C2)c1-c1cc(Nc2cnc(C#N)cn2)n[nH]1] | 5-((5-(2-(((1R,3S)-3-aminocycloheptyl)oxy)-6-methoxyphenyl)-1H-pyrazol-3-yl)amino)pyrazine-2-carbonitrile |
| 3-9 | 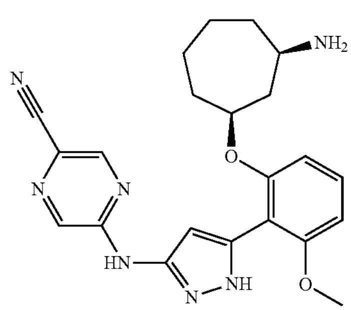 [SMILES: COc1cccc(O[C@H]2CCCC[C@@H](N)C2)c1-c1cc(Nc2cnc(C#N)cn2)n[nH]1] | 5-((5-(2-(((1S,3R)-3-aminocycloheptyl)oxy)-6-methoxyphenyl)-1H-pyrazol-3-yl)amino)pyrazine-2-carbonitrile |

TABLE 1-continued

| Ex. | Structure | Name |
|---|---|---|
| 3-10 | 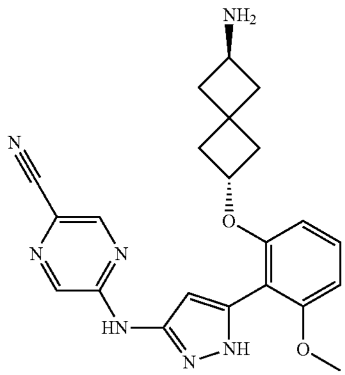 [SMILES: COc1cccc(O[C@H]2CC3(C[C@@H](N)C3)C2)c1-c1cc(Nc2cnc(C#N)cn2)n[nH]1] | 5-((5-(2-(((6-aminospiro[3.3]heptan-2-yl)oxy)-6-methoxyphenyl)-1H-pyrazol-3-yl)amino)pyrazine-2-carbonitrile |
| 3-11 | 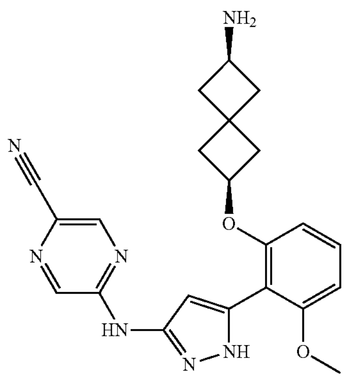 [SMILES: COc1cccc(O[C@H]2CC3(C[C@@H](N)C3)C2)c1-c1cc(Nc2cnc(C#N)cn2)n[nH]1] | 5-((5-(2-(((6-aminospiro[3.3]heptan-2-yl)oxy)-6-methoxyphenyl)-1H-pyrazol-3-yl)amino)pyrazine-2-carbonitrile |
| 3-12 | 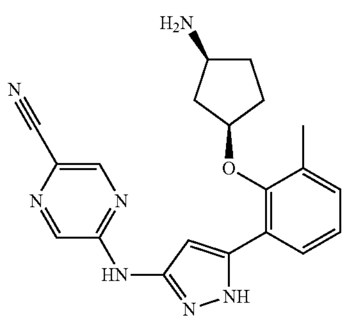 [SMILES: Cc1cccc(-c2cc(Nc3cnc(C#N)cn3)n[nH]2)c1O[C@@H]1CC[C@H](N)C1] | 5-((5-(2-(((1R,3S)-3-aminocyclopentyl)oxy)-3-methylphenyl)-1H-pyrazol-3-yl)amino)pyrazine-2-carbonitrile |
| 3-13 | 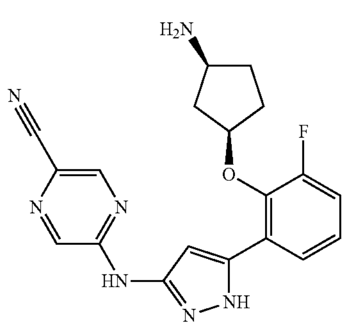 [SMILES: N#Cc1cnc(Nc2cc(-c3cccc(F)c3O[C@@H]3CC[C@H](N)C3)[nH]n2)cn1] | 5-((5-(2-(((1R,3S)-3-aminocyclopentyl)oxy)-3-fluorophenyl)-1H-pyrazol-3-yl)amino)pyrazine-2-carbonitrile |

TABLE 1-continued

| Ex. | Structure | Name |
|---|---|---|
| 3-14 | 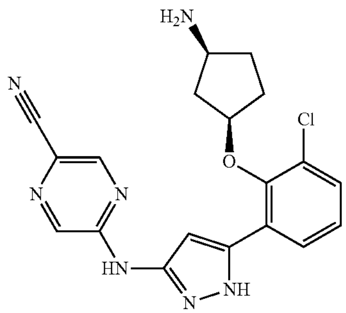 [SMILES: N#Cc1cnc(Nc2cc(-c3cccc(Cl)c3O[C@@H]3CC[C@H](N)C3)[nH]n2)cn1] | 5-((5-(2-(((1R,3S)-3-aminocyclopentyl)oxy)-3-chlorophenyl)-1H-pyrazol-3-yl)amino)pyrazine-2-carbonitrile |
| 3-15 | 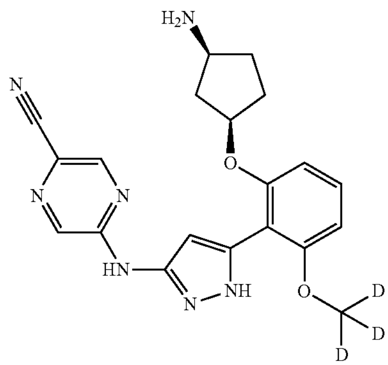 [SMILES: [2H]C([2H])([2H])Oc1cccc(O[C@@H]2CC[C@H](N)C2)c1-c1cc(Nc2cnc(C#N)cn2)n[nH]1] | 5-((5-(2-(((1R,3S)-3-aminocyclopentyl)oxy)-6-(methoxy-d3)phenyl)-1H-pyrazol-3-yl)amino)pyrazine-2-carbonitrile |
| 3-16 | 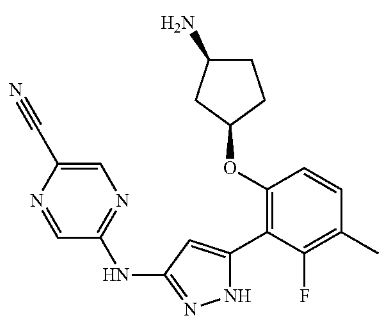 [SMILES: Cc1ccc(O[C@@H]2CC[C@H](N)C2)c(-c2cc(Nc3cnc(C#N)cn3)n[nH]2)c1F] | 5-((5-(6-(((1R,3S)-3-aminocyclopentyl)oxy)-2-fluoro-3-methylphenyl)-1H-pyrazol-3-yl)amino)pyrazine-2-carbonitrile |
| 3-17 | 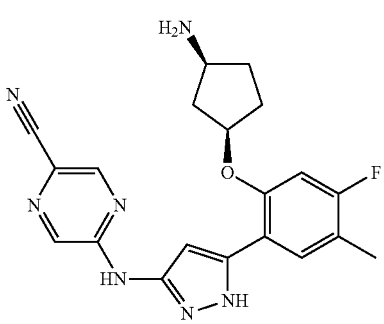 [SMILES: Cc1cc(-c2cc(Nc3cnc(C#N)cn3)n[nH]2)c(O[C@@H]2CC[C@H](N)C2)cc1F] | 5-((5-(2-(((1R,3S)-3-aminocyclopentyl)oxy)-4-fluoro-5-methylphenyl)-1H-pyrazol-3-yl)amino)pyrazine-2-carbonitrile |

TABLE 1-continued

| Ex. | Structure | Name |
|---|---|---|
| 3-18 | 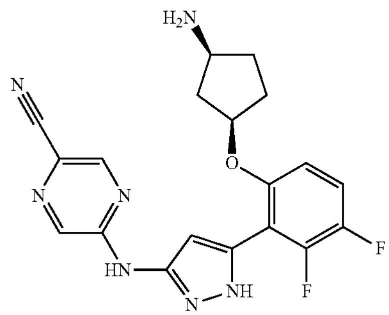 [SMILES: N#Cc1cnc(Nc2cc(-c3c(O[C@@H]4CC[C@H](N)C4)ccc(F)c3F)[nH]n2)cn1] | 5-((5-(6-((((1R,3S)-3-aminocyclopentyl)oxy)-2,3-difluorophenyl)-1H-pyrazol-3-yl)amino)pyrazine-2-carbonitrile |
| 3-19 | 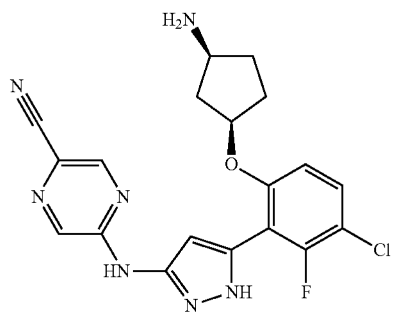 [SMILES: N#Cc1cnc(Nc2cc(-c3c(O[C@@H]4CC[C@H](N)C4)ccc(Cl)c3F)[nH]n2)cn1] | 5-((5-(6-((((1R,3S)-3-aminocyclopentyl)oxy)-3-chloro-2-fluorophenyl)-1H-pyrazol-3-yl)amino)pyrazine-2-carbonitrile |
| 3-20 | 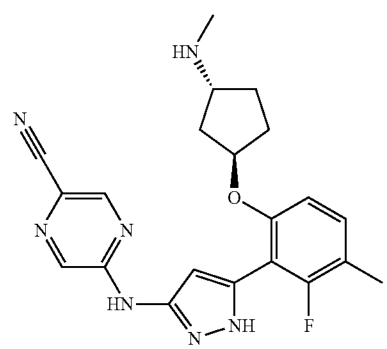 [SMILES: CN[C@@H]1CC[C@@H](Oc2ccc(C)c(F)c2-c2cc(Nc3cnc(C#N)cn3)n[nH]2)C1] | 5-((5-(2-fluoro-3-methyl-6-((((1R,3R)-3-(methylamino)cyclopentyl)oxy)phenyl)-1H-pyrazol-3-yl)amino)pyrazine-2-carbonitrile |
| 3-21 | 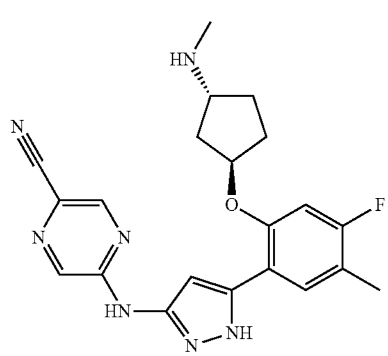 [SMILES: CN[C@@H]1CC[C@@H](Oc2cc(F)c(C)cc2-c2cc(Nc3cnc(C#N)cn3)n[nH]2)C1] | 5-((5-(4-fluoro-5-methyl-2-((((1R,3R)-3-(methylamino)cyclopentyl)oxy)phenyl)-1H-pyrazol-3-yl)amino)pyrazine-2-carbonitrile |

TABLE 1-continued

| Ex. | Structure | Name |
|---|---|---|
| 3-22 | 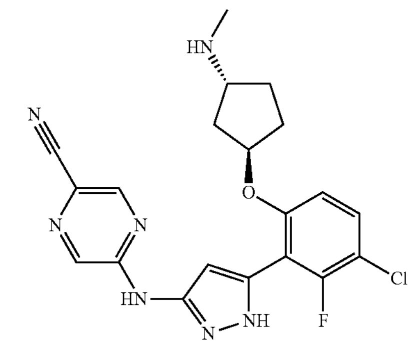 [SMILES: CN[C@@H]1CC[C@@H](Oc2ccc(Cl)c(F)c2-c2cc(Nc3cnc(C#N)cn3)n[nH]2)C1] | 5-((5-(3-chloro-2-fluoro-6-(((1R,3R)-3-(methylamino)cyclopentyl)oxy)phenyl)-1H-pyrazol-3-yl)amino)pyrazine-2-carbonitrile |
| 3-23 | 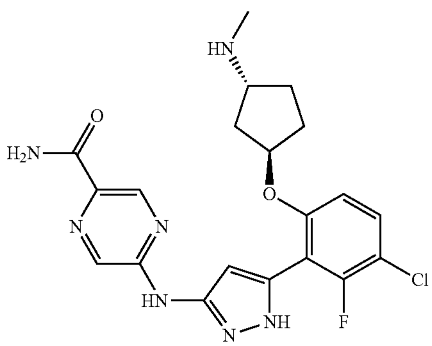 [SMILES: CN[C@@H]1CC[C@@H](Oc2ccc(Cl)c(F)c2-c2cc(Nc3cnc(C(N)=O)cn3)n[nH]2)C1] | 5-((5-(3-chloro-2-fluoro-6-(((1R,3R)-3-(methylamino)cyclopentyl)oxy)phenyl)-1H-pyrazol-3-yl)amino)pyrazine-2-carboxamide |
| 3-24 | 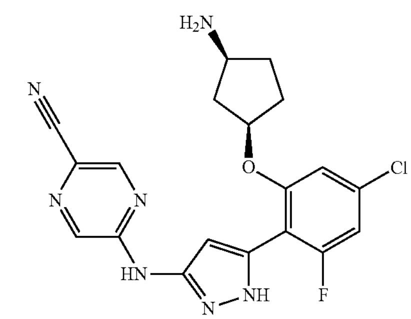 [SMILES: N#Cc1cnc(Nc2cc(-c3c(F)cc(Cl)cc3O[C@@H]3CC[C@H](N)C3)[nH]n2)cn1] | 5-((5-(2-(((1R,3S)-3-aminocyclopentyl)oxy)-4-chloro-6-fluorophenyl)-1H-pyrazol-3-yl)amino)pyrazine-2-carbonitrile |
| 3-25 | 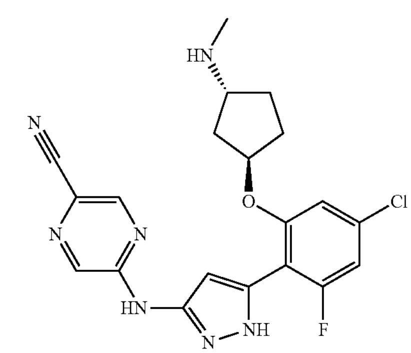 [SMILES: CN[C@@H]1CC[C@@H](Oc2cc(Cl)cc(F)c2-c2cc(Nc3cnc(C#N)cn3)n[nH]2)C1] | 5-((5-(4-chloro-2-fluoro-6-(((1R,3R)-3-(methylamino)cyclopentyl)oxy)phenyl)-1H-pyrazol-3-yl)amino)pyrazine-2-carbonitrile |

TABLE 1-continued

| Ex. | Structure | Name |
|---|---|---|
| 3-26 | 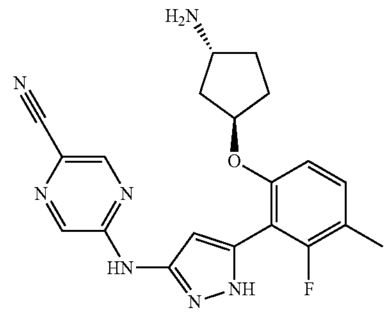 [SMILES: Cc1ccc(O[C@@H]2CC[C@@H](N)C2)c(-c2cc(Nc3cnc(C#N)cn3)n[nH]2)c1F] | 5-((5-(6-(((1R,3R)-3-aminocyclopentyl)oxy)-2-fluoro-3-methylphenyl)-1H-pyrazol-3-yl)amino)pyrazine-2-carbonitrile |
| 3-27 | 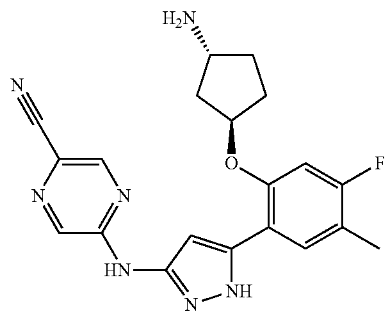 [SMILES: Cc1cc(-c2cc(Nc3cnc(C#N)cn3)n[nH]2)c(O[C@@H]2CC[C@@H](N)C2)cc1F] | 5-((5-(2-(((1R,3R)-3-aminocyclopentyl)oxy)-4-fluoro-5-methylphenyl)-1H-pyrazol-3-yl)amino)pyrazine-2-carbonitrile |
| 3-28 | 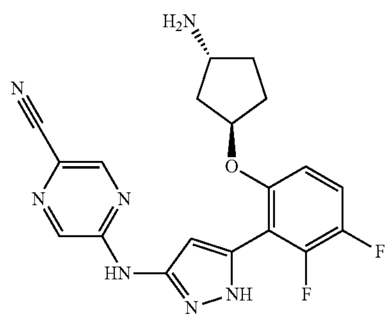 [SMILES: N#Cc1cnc(Nc2cc(-c3c(O[C@@H]4CC[C@@H](N)C4)ccc(F)c3F)[nH]n2)cn1] | 5-((5-(6-(((1R,3R)-3-aminocyclopentyl)oxy)-2,3-difluorophenyl)-1H-pyrazol-3-yl)amino)pyrazine-2-carbonitrile |
| 3-29 | 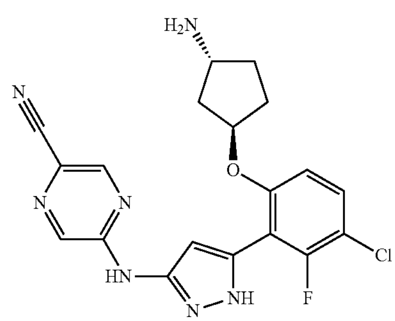 [SMILES: N#Cc1cnc(Nc2cc(-c3c(O[C@@H]4CC[C@@H](N)C4)ccc(Cl)c3F)[nH]n2)cn1] | 5-((5-(6-(((1R,3R)-3-aminocyclopentyl)oxy)-3-chloro-2-fluorophenyl)-1H-pyrazol-3-yl)amino)pyrazine-2-carbonitrile |
| 3-30 | 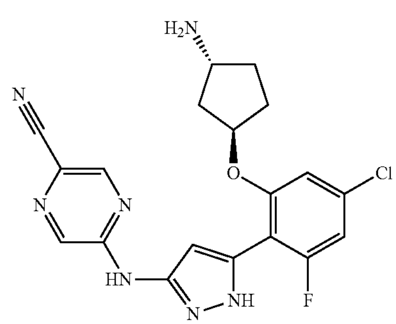 [SMILES: N#Cc1cnc(Nc2cc(-c3c(F)cc(Cl)cc3O[C@@H]3CC[C@@H](N)C3)[nH]n2)cn1] | 5-((5-(2-(((1R,3R)-3-aminocyclopentyl)oxy)-4-chloro-6-fluoropheny)-1H-pyrazol-3-yl)amino)pyrazine-2-carbonitrile |

TABLE 1-continued

| Ex. | Structure | Name |
|---|---|---|
| 3-31 | 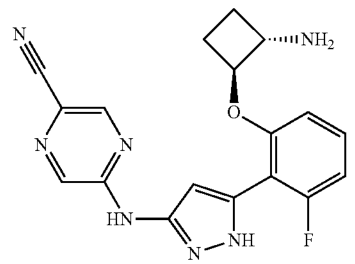 [SMILES: N#Cc1cnc(Nc2cc(-c3c(F)cccc3O[C@H]3CC[C@@H]3N)[nH]n2)cn1] | 5-((5-(2-((1S,2S)-2-aminocyclobutoxy)-6-fluorophenyl)-1H-pyrazol-3-yl)amino)pyrazine-2-carbonitrile |
| 3-32 | 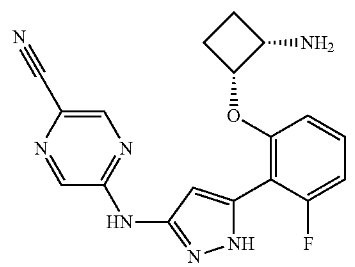 [SMILES: N#Cc1cnc(Nc2cc(-c3c(F)cccc3O[C@@H]3CC[C@@H]3N)[nH]n2)cn1] | 5-((5-(2-((1R,2S)-2-aminocyclobutoxy)-6-fluorophenyl)-1H-pyrazol-3-yl)amino)pyrazine-2-carbonitrile |
| 3-33 | 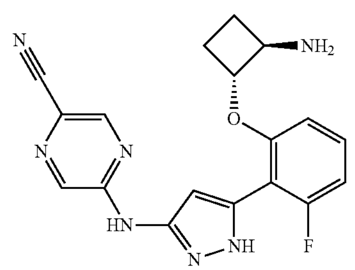 [SMILES: N#Cc1cnc(Nc2cc(-c3c(F)cccc3O[C@@H]3CC[C@H]3N)[nH]n2)cn1] | 5-((5-(2-((1R,2R)-2-aminocyclobutoxy)-6-fluorophenyl)-1H-pyrazol-3-yl)amino)pyrazine-2-carbonitrile |
| 3-34 | 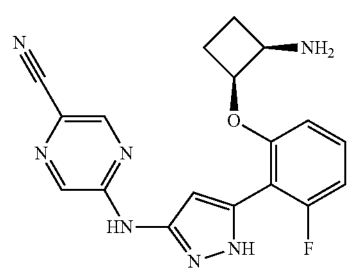 [SMILES: N#Cc1cnc(Nc2cc(-c3c(F)cccc3O[C@H]3CC[C@H]3N)[nH]n2)cn1] | 5-((5-(2-((1S,2R)-2-aminocyclobutoxy)-6-fluorophenyl)-1H-pyrazol-3-yl)amino)pyrazine-2-carbonitrile |
| 3-35 | 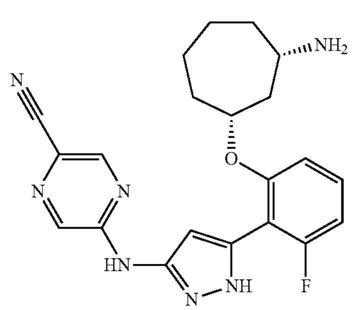 [SMILES: N#Cc1cnc(Nc2cc(-c3c(F)cccc3O[C@@H]3CCCC[C@H](N)C3)[nH]n2)cn1] | 5-((5-(2-(((1R,3S)-3-aminocycloheptyl)oxy)-6-fluorophenyl)-1H-pyrazol-3-yl)amino)pyrazine-2-carbonitrile |

TABLE 1-continued

| Ex. | Structure | Name |
|---|---|---|
| 3-36 | 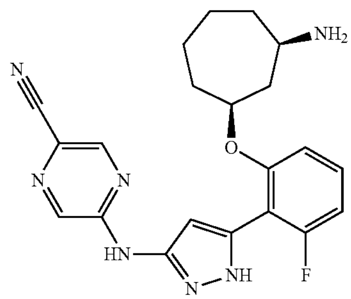 [SMILES: N#Cc1cnc(Nc2cc(-c3c(F)cccc3O[C@H]3CCCC[C@@H](N)C3)[nH]n2)cn1] | 5-((5-(2-(((1S,3R)-3-aminocycloheptyl)oxy)-6-fluorophenyl)-1H-pyrazol-3-yl)amino)pyrazine-2-carbonitrile |
| 3-37 | 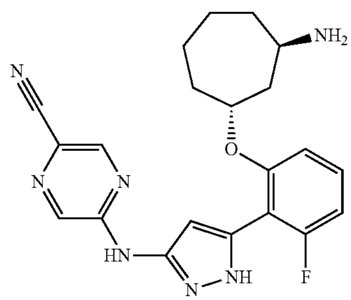 [SMILES: N#Cc1cnc(Nc2cc(-c3c(F)cccc3O[C@@H]3CCCC[C@@H](N)C3)[nH]n2)cn1] | 5-((5-(2-(((1R,3R)-3-aminocycloheptyl)oxy)-6-fluorophenyl)-1H-pyrazol-3-yl)amino)pyrazine-2-carbonitrile |
| 3-38 | 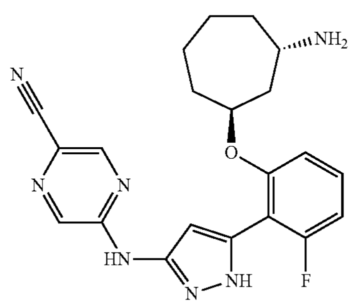 [SMILES: N#Cc1cnc(Nc2cc(-c3c(F)cccc3O[C@H]3CCCC[C@H](N)C3)[nH]n2)cn1] | 5-((5-(2-(((1S,3S)-3-aminocycloheptyl)oxy)-6-fluorophenyl)-1H-pyrazol-3-yl)amino)pyrazine-2-carbonitrile |
| 3-39 | 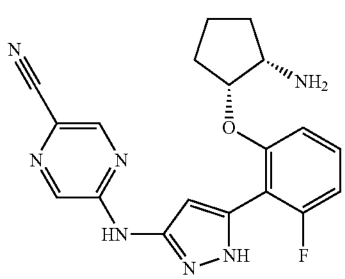 [SMILES: N#Cc1cnc(Nc2cc(-c3c(F)cccc3O[C@@H]3CCC[C@@H]3N)[nH]n2)cn1] | 5-((5-(2-(((1R,2S)-2-aminocyclopentyl)oxy)-6-fluorophenyl)-1H-pyrazol-3-yl)amino)pyrazine-2-carbonitrile |
| 3-40 | 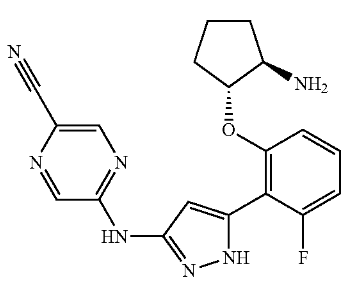 [SMILES: N#Cc1cnc(Nc2cc(-c3c(F)cccc3O[C@@H]3CCC[C@H]3N)[nH]n2)cn1] | 5-((5-(2-(((1R,2R)-2-aminocyclopentyl)oxy)-6-fluorophenyl)-1H-pyrazol-3-yl)amino)pyrazine-2-carbonitrile |

TABLE 1-continued

| Ex. | Structure | Name |
|---|---|---|
| 3-41 | 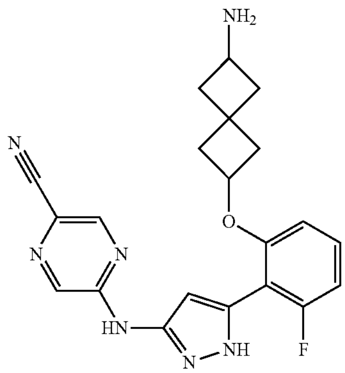 [SMILES: N#Cc1cnc(Nc2cc(-c3c(F)cccc3OC3CC4(CC(N)C4)C3)[nH]n2)cn1] | 5-((5-(2-(((6-aminospiro[3.3]heptan-2-yl)oxy)-6-fluorophenyl)-1H-pyrazol-3-yl)amino)pyrazine-2-carbonitrile |
| 3-42 | 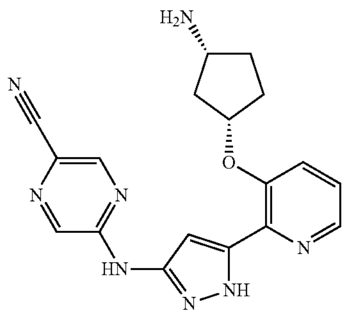 [SMILES: N#Cc1cnc(Nc2cc(-c3ncccc3O[C@H]3CC[C@@H](N)C3)[nH]n2)cn1] | 5-((5-(3-(((1S,3R)-3-aminocyclopentyl)oxy)pyridin-2-yl)-1H-pyrazol-3-yl)amino)pyrazine-2-carbonitrile |
| 3-43 | 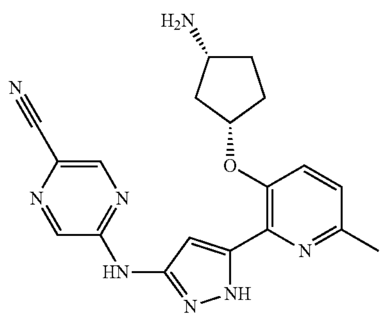 [SMILES: Cc1ccc(O[C@H]2CC[C@@H](N)C2)c(-c2cc(Nc3cnc(C#N)cn3)n[nH]2)n1] | 5-((5-(3-(((1S,3R)-3-aminocyclopentyl)oxy)-6-methylpyridin-2-yl)-1H-pyrazol-3-yl)amino)pyrazine-2-carbonitrile |
| 3-44 | 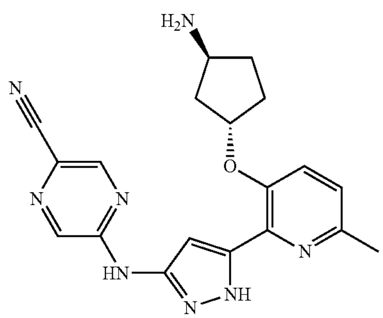 [SMILES: Cc1ccc(O[C@H]2CC[C@H](N)C2)c(-c2cc(Nc3cnc(C#N)cn3)n[nH]2)n1] | 5-((5-(3-(((1S,3S)-3-aminocyclopentyl)oxy)-6-methylpyridin-2-yl)-1H-pyrazol-3-yl)amino)pyrazine-2-carbonitrile |

TABLE 1-continued

| Ex. | Structure | Name |
|---|---|---|
| 3-45 | 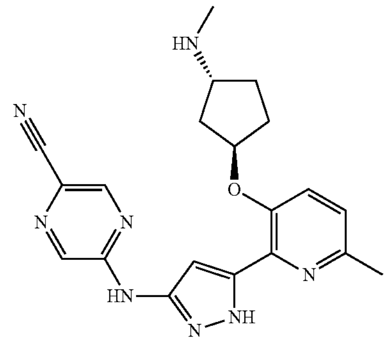 [SMILES: CN[C@@H]1CC[C@@H](Oc2ccc(C)nc2-c2cc(Nc3cnc(C#N)cn3)n[nH]2)C1] | 5-((5-(6-methyl-3-((((1R,3R)-3-(methylamino)cyclopentyl)oxy)pyridin-2-yl)-1H-pyrazol-3-yl)amino)pyrazine-2-carbonitrile |
| 3-46 | 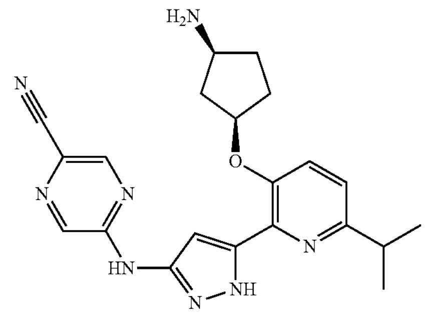 [SMILES: CC(C)c1ccc(O[C@@H]2CC[C@H](N)C2)c(-c2cc(Nc3cnc(C#N)cn3)n[nH]2)n1] | 5-((5-(3-(((1R,3S)-3-aminocyclopentyl)oxy)-6-isopropylpyridin-2-yl)-1H-pyrazol-3-yl)amino)pyrazine-2-carbonitrile |
| 3-47 | 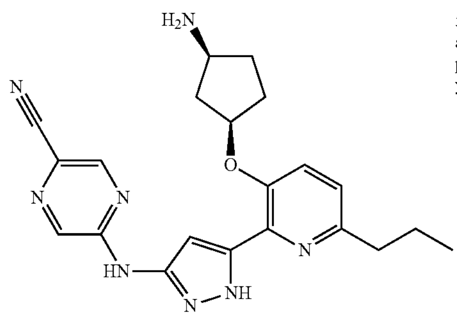 [SMILES: CCCc1ccc(O[C@@H]2CC[C@H](N)C2)c(-c2cc(Nc3cnc(C#N)cn3)n[nH]2)n1] | 5-((5-(3-(((1R,3S)-3-aminocyclopentyl)oxy)-6-propylpyridin-2-yl)-1H-pyrazol-3-yl)amino)pyrazine-2-carbonitrile |
| 3-48 | 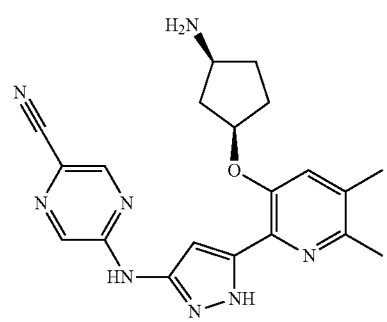 [SMILES: Cc1cc(O[C@@H]2CC[C@H](N)C2)c(-c2cc(Nc3cnc(C#N)cn3)n[nH]2)nc1C] | 5-((5-(3-(((1R,3S)-3-aminocyclopentyl)oxy)-5,6-dimethylpyridin-2-yl)-1H-pyrazol-3-yl)amino)pyrazine-2-carbonitrile |
| 3-49 | 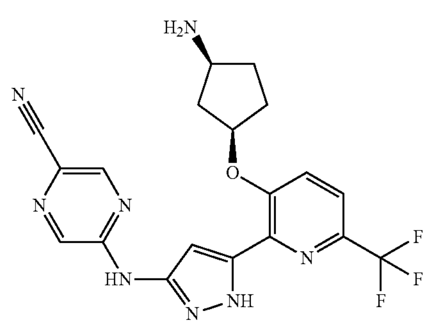 [SMILES: N#Cc1cnc(Nc2cc(-c3nc(C(F)(F)F)ccc3O[C@@H]3CC[C@H](N)C3)[nH]n2)cn1] | 5-((5-(3-(((1R,3S)-3-aminocyclopentyl)oxy)-6-(trifluoromethyl)pyridin-2-yl)-1H-pyrazol-3-yl)amino)pyrazine-2-carbonitrile |

TABLE 1-continued

| Ex. | Structure | Name |
|---|---|---|
| 3-50 | 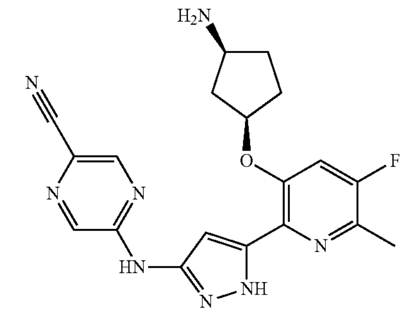 [SMILES: Cc1nc(-c2cc(Nc3cnc(C#N)cn3)n[nH]2)c(O[C@@H]2CC[C@H](N)C2)cc1F] | 5-((5-(3-(((1R,3S)-3-aminocyclopentyl)oxy)-5-fluoro-6-methylpyridin-2-yl)-1H-pyrazol-3-yl)amino)pyrazine-2-carbonitrile |
| 3-51 | 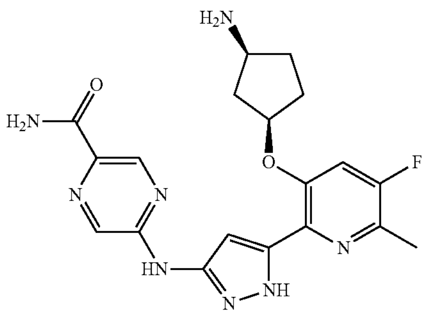 [SMILES: Cc1nc(-c2cc(Nc3cnc(C(N)=O)cn3)n[nH]2)c(O[C@@H]2CC[C@H](N)C2)cc1F] | 5-((5-(3-(((1R,3S)-3-aminocyclopentyl)oxy)-5-fluoro-6-methylpyridin-2-yl)-1H-pyrazol-3-yl)amino)pyrazine-2-carboxamide |
| 3-52 | 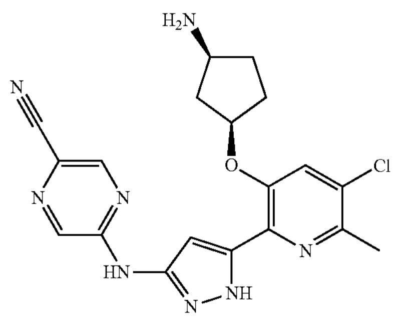 [SMILES: Cc1nc(-c2cc(Nc3cnc(C#N)cn3)n[nH]2)c(O[C@@H]2CC[C@H](N)C2)cc1Cl] | 5-((5-(3-(((1R,3S)-3-aminocyclopentyl)oxy)-5-chloro-6-methylpyridin-2-yl)-1H-pyrazol-3-yl)amino)pyrazine-2-carbonitrile |
| 3-53 | 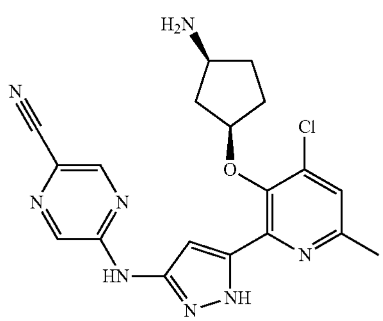 [SMILES: Cc1cc(Cl)c(O[C@@H]2CC[C@H](N)C2)c(-c2cc(Nc3cnc(C#N)cn3)n[nH]2)n1] | 5-((5-(3-(((1R,3S)-3-aminocyclopentyl)oxy)-4-chloro-6-methylpyridin-2-yl)-1H-pyrazol-3-yl)amino)pyrazine-2-carbonitrile |
| 3-54 | 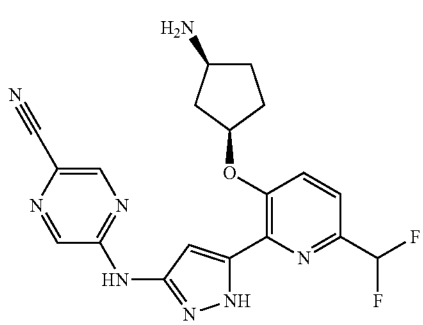 [SMILES: N#Cc1cnc(Nc2cc(-c3nc(C(F)F)ccc3O[C@@H]3CC[C@H](N)C3)[nH]n2)cn1] | 5-((5-(3-(((1R,3S)-3-aminocyclopentyl)oxy)-6-(difluoromethyl)pyridin-2-yl)-1H-pyrazol-3-yl)amino)pyrazine-2-carbonitrile |

TABLE 1-continued

| Ex. | Structure | Name |
|---|---|---|
| 4-1 | 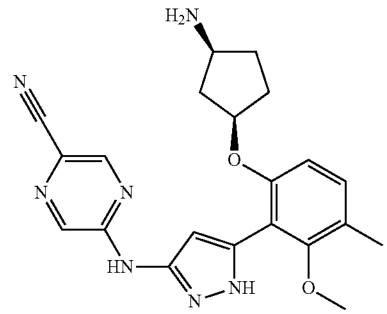 [SMILES: COc1c(C)ccc(O[C@@H]2CC[C@H](N)C2)c1-c1cc(Nc2cnc(C#N)cn2)n[nH]1] | 5-((5-(6-(((1R,3S)-3-aminocyclopentyl)oxy)-2-methoxy-3-methylphenyl)-1H-pyrazol-3-yl)amino)pyrazine-2-carbonitrile |
| 4-2 | 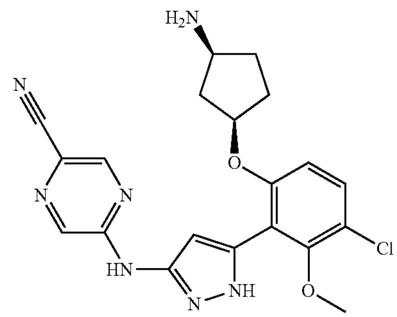 [SMILES: COc1c(Cl)ccc(O[C@@H]2CC[C@H](N)C2)c1-c1cc(Nc2cnc(C#N)cn2)n[nH]1] | 5-((5-(6-(((1R,3S)-3-aminocyclopentyl)oxy)-3-chloro-2-methoxyphenyl)-1H-pyrazol-3-yl)amino)pyrazine-2-carbonitrile |
| 4-3 | 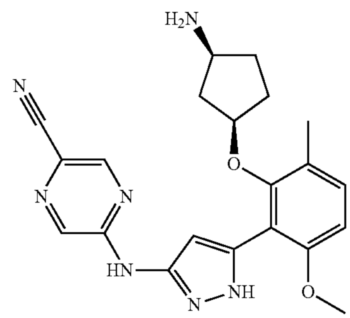 [SMILES: COc1ccc(C)c(O[C@@H]2CC[C@H](N)C2)c1-c1cc(Nc2cnc(C#N)cn2)n[nH]1] | 5-((5-(2-(((1R,3S)-3-aminocyclopentyl)oxy)-6-methoxy-3-methylphenyl)-1 H-pyrazol-3-yl)amino)pyrazine-2-carbonitrile |
| 4-4 | 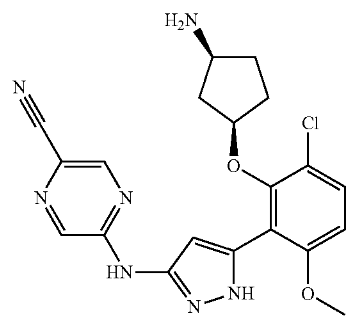 [SMILES: COc1ccc(Cl)c(O[C@@H]2CC[C@H](N)C2)c1-c1cc(Nc2cnc(C#N)cn2)n[nH]1] | 5-((5-(2-(((1R,3S)-3-aminocyclopentyl)oxy)-3-chloro-6-methoxyphenyl)-1H-pyrazol-3-yl)amino)pyrazine-2-carbonitrile |
| 4-5 | 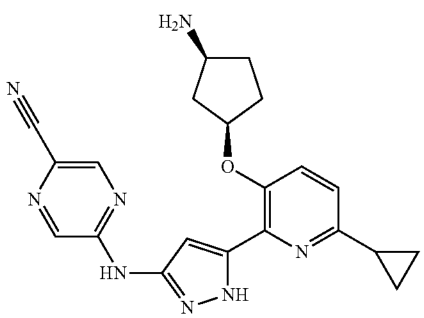 [SMILES: N#Cc1cnc(Nc2cc(-c3nc(C4CC4)ccc3O[C@@H]3CC[C@H](N)C3)[nH]n2)cn1] | 5-((5-(3-(((1R,3S)-3-aminocyclopentyl)oxy)-6-cyclopropylpyridin-2-yl)-1H-pyrazol-3-yl)amino)pyrazine-2-carbonitrile |

TABLE 1-continued

| Ex. | Structure | Name |
|---|---|---|
| 5-1 | 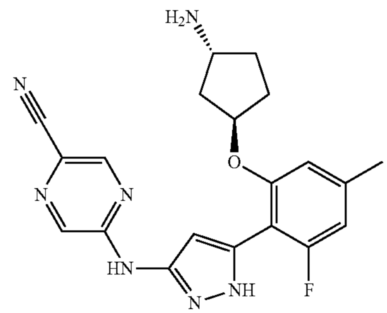 [SMILES: Cc1cc(F)c(-c2cc(Nc3cnc(C#N)cn3)n[nH]2)c(O[C@@H]2CC[C@@H](N)C2)c1] | 5-((5-(2-(((1R,3R)-3-aminocyclopentyl)oxy)-6-fluoro-4-methylphenyl)-1H-pyrazol-3-yl)amino)pyrazine-2-carbonitrile |
| 5-2 | 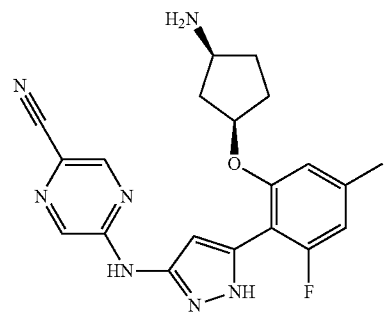 [SMILES: Cc1cc(F)c(-c2cc(Nc3cnc(C#N)cn3)n[nH]2)c(O[C@@H]2CC[C@H](N)C2)c1] | 5-((5-(2-(((1R,3S)-3-aminocyclopentyl)oxy)-6-fluoro-4-methylphenyl)-1H-pyrazol-3-yl)amino)pyrazine-2-carbonitrile |
| 5-3 | 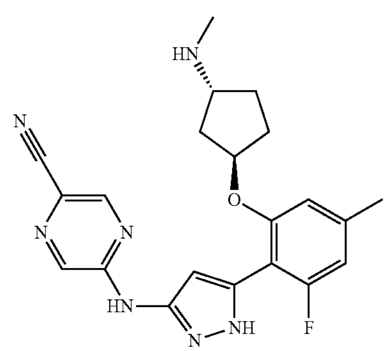 [SMILES: CN[C@@H]1CC[C@@H](Oc2cc(C)cc(F)c2-c2cc(Nc3cnc(C#N)cn3)n[nH]2)C1] | 5-((5-(2-fluoro-4-methyl-6-(((1R,3R)-3-(methylamino)cyclopentyl)oxy)phenyl)-1H-pyrazol-3-yl)amino)pyrazine-2-carbonitrile |
| 5-4 | 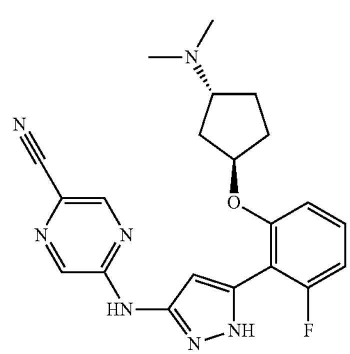 [SMILES: CN(C)[C@@H]1CC[C@@H](Oc2cccc(F)c2-c2cc(Nc3cnc(C#N)cn3)n[nH]2)C1] | 5-((5-(2-(((1R,3R)-3-(dimethylamino)cyclopentyl)oxy)-6-fluorophenyl)-1H-pyrazol-3-yl)amino)pyrazine-2-carbonitrile |

TABLE 2

| Ex. | Structure | Name |
|---|---|---|
| 1-2 | 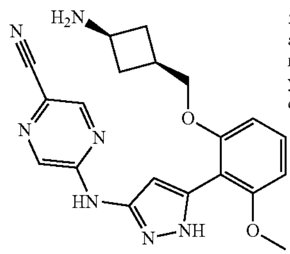 | 5-((5-(2-(((1s,3s)-3-aminocyclobutyl)methoxy)-6-methoxyphenyl)-1H-pyrazol-3-yl)amino)pyrazine-2-carbonitrile |
| 1-3 | 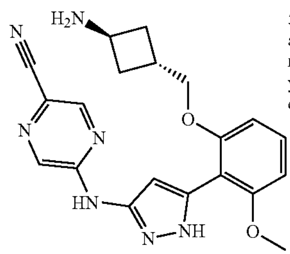 | 5-((5-(2-(((1r,3r)-3-aminocyclobutyl)methoxy)-6-methoxyphenyl)-1H-pyrazol-3-yl)amino)pyrazine-2-carbonitrile |
| 3-55 | 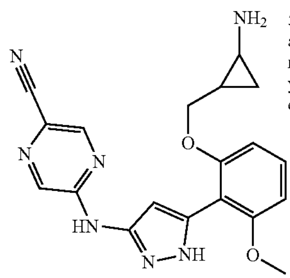 | 5-((5-(2-((2-aminocyclopropyl)methoxy)-6-methoxyphenyl)-1H-pyrazol-3-yl)amino)pyrazine-2-carbonitrile |

TABLE 3

| Structure | Name |
|---|---|
| 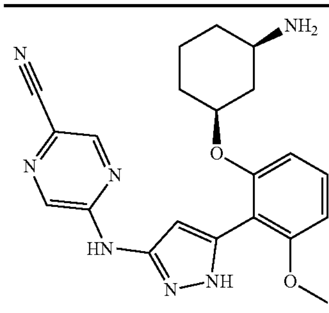 | 5-((5-(2-(((1S,3R)-3-aminocyclohexyl)oxy)-6-methoxyphenyl)-1H-pyrazol-3-yl)amino)pyrazine-2-carbonitrile |
| 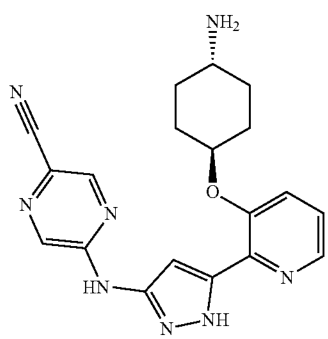 [SMILES: N#Cc1cnc(Nc2cc(-c3ncccc3O[C@H]3CC[C@H](N)CC3)[nH]n2)cn1] | 5-((5-(3-(((1r,4r)-4-aminocyclohexyl)oxy)pyridin-2-yl)-1H-pyrazol-3-yl)amino)pyrazine-2-carbonitrile |

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein, or a solvate, tautomer, or stereoisomer thereof, include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof that contain the aforementioned isotopes and/or other isotopes of other atoms are within the scope of this disclosure. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compound or a pharmaceutically acceptable salt, solvate, tautomer, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein that comprise a free acid group react with a suitable base, such as the hydroxide, carbonate, bicarbonate, or sulfate of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\text{ alkyl})_4$, and the like. Representative salts include the alkali or alkaline earth salts, like lithium, sodium, potassium, calcium, and magnesium, and aluminum salts and the like of the tetrazole.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, such as water, ethanol, and the like. Hydrates are formed when the solvent is water, or alcoholates are formed when the solvent is alcohol. Solvates of the compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH, Inc. (Toronto, Canada), Bionet (Cornwall, U.K.), Chem Service Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line. Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts," Verlag Helvetica Chimica Acta, Zurich, 2002.

Pharmaceutical Compositions

In certain embodiments, the compound described herein is administered as a pure chemical. In some embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, $21^{st}$ Ed. Mack Pub. Co., Easton, Pa. (2005)).

Accordingly, provided herein is a pharmaceutical composition comprising a compound described herein, or a pharmaceutically acceptable salt, solvate, tautomer, or stereoisomer thereof, and a pharmaceutically acceptable excipient.

In certain embodiments, the compound provided herein is substantially pure, in that it contains less than about 5%, or less than about 1%, or less than about 0.1% of other organic small molecules, such as unreacted intermediates or synthesis by-products that are created, for example, in one or more of the steps of a synthesis method.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as increased overall response rate, increased duration of response, more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

In some embodiments, the pharmaceutical composition is formulated for oral, topical (including buccal and sublingual), rectal, vaginal, transdermal, parenteral, intrapulmonary, intradermal, intrathecal, epidural, or intranasal administration. Parenteral administration includes intramuscular, intravenous, intraarterial, intraperitoneal, or subcutaneous administration. In some embodiments, the pharmaceutical composition is formulated for intravenous injection, oral administration, inhalation, nasal administration, topical administration, or ophthalmic administration. In some embodiments, the pharmaceutical composition is formulated for oral administration. In some embodiments, the pharmaceutical composition is formulated for intravenous injection. In some embodiments, the pharmaceutical composition is formulated as a tablet, a pill, a capsule, a liquid, an inhalant, a nasal spray solution, a suppository, a suspension, a gel, a colloid, a dispersion, a suspension, a solution, an emulsion, an ointment, a lotion, an eye drop, or an ear drop. In some embodiments, the pharmaceutical composition is formulated as a tablet.

Suitable doses and dosage regimens are determined by conventional range-finding techniques known to those of ordinary skill in the art. Generally, treatment is initiated with smaller dosages that are less than the optimum dose of the compound disclosed herein. Thereafter, the dosage is increased by small increments until the optimum effect under the circumstances is reached. In some embodiments, the present method involves the administration of about 0.1 µg to about 50 mg of at least one compound described herein per kg body weight of the subject. For a 70 kg patient, dosages of from about 10 µg to about 200 mg of the compound disclosed herein would be more commonly used, depending on a subject's physiological response.

By way of example only, the dose of the compound described herein for methods of treating a disease as described herein is about 0.001 to about 1 mg/kg body weight of the subject per day, for example, about 0.001 mg, about 0.002 mg, about 0.005 mg, about 0.010 mg, 0.015 mg, about 0.020 mg, about 0.025 mg, about 0.050 mg, about 0.075 mg, about 0.1 mg, about 0.15 mg, about 0.2 mg, about 0.25 mg, about 0.5 mg, about 0.75 mg, or about 1 mg/kg body weight per day. In some embodiments, the dose of compound described herein for the described methods is about 1 to about 1000 mg/kg body weight of the subject being treated per day, for example, about 1 mg, about 2 mg, about 5 mg, about 10 mg, about 15 mg, about 20 mg, about 25 mg, about 50 mg, about 75 mg, about 100 mg, about 150 mg, about 200 mg, about 250 mg, about 500 mg, about 750 mg, or about 1000 mg per day.

Methods of Treatment

Disclosed herein are methods for treating cancer in a subject in need thereof, including administering to the subject a therapeutically effective amount of a compound disclosed herein, or a pharmaceutically acceptable salt, solvate, tautomer, or stereoisomer thereof. Disclosed herein are methods for treating a Chk1-related cancer in a subject in need thereof, including administering to the subject a therapeutically effective amount of a compound disclosed herein, or a pharmaceutically acceptable salt, solvate, tautomer, or stereoisomer thereof.

In some embodiments, the cancer includes malignant tumors whose size can be decreased, whose growth or spread can be halted, or whose symptom is in remission or alleviated and/or completely cured by deleting or suppressing and/or inhibiting functions of Chk1. Malignant tumors of interest are, but not limited to, head and neck cancer, gastrointestinal cancer (esophageal cancer, gastric cancer, duodenal cancer, liver cancer, biliary tract cancer (gallbladder, bile duct cancer, etc.), pancreatic cancer, colorectal cancer (colon cancer, rectal cancer, etc.), etc.), lung cancer (non-small cell lung cancer, small cell lung cancer, squamous cell lung carcinoma, mesothelioma, etc.), breast cancer, genital cancer (ovarian cancer, uterine cancer, cervical cancer, endometrial cancer, etc.), urinary cancer (kidney cancer, bladder cancer, prostate cancer, testicular tumor, etc.), hematopoietic tumors (leukemia, malignant lymphoma, multiple myeloma, etc.), bone and soft tissue tumors (e.g., soft tissue sarcomas and osteosarcomas), skin cancer, brain tumor (e.g., glioblastoma) and the like.

In some embodiments, the term cancer is used in accordance with its plain ordinary meaning in light of the present disclosure and refers to all types of cancer, neoplasm or malignant tumors found in mammals, including leukemias, lymphomas, melanomas, neuroendocrine tumors, carcinomas, and sarcomas. Exemplary cancers that may be treated with a compound disclosed herein, or a pharmaceutically acceptable salt, solvate, tautomer, or stereoisomer thereof, pharmaceutical compositions include acute myeloid leukemia, adrenal cortical cancer, adrenal gland cancer, bladder cancer, bone cancer, brain cancer, breast cancer (e.g., ductal carcinoma, lobular carcinoma, primary, metastatic), breast cancer, cancer of the endocrine system, cancer of the hepatic stellate cells, cancer of the pancreatic stellate cells, cervical cancer, colon cancer, colorectal cancer, ductal carcinoma, endometrial cancer, esophageal cancer, gastric cancer, genitourinary tract cancer, glioblastoma, glioma, head and neck cancer, hepatocellular carcinoma, Hodgkin's Disease, kidney cancer, leukemia (e.g., lymphoblastic leukemia, chronic lymphocytic leukemia, hairy cell leukemia), liver cancer (e.g., hepatocellular carcinoma), lobular carcinoma, lung cancer (e.g., non-small cell lung carcinoma, squamous cell lung carcinoma, adenocarcinoma, large cell lung carcinoma, small cell lung carcinoma, carcinoid, sarcoma), lymph node cancer, lymphoma (e.g., Mantel cell lymphoma, follicular lymphoma, diffuse large B-cell lymphoma, marginal zona lymphoma, Burkitt's lymphoma, Non-Hodgkin's Lymphoma) malignant carcinoid, malignant hypercalcemia, malignant pancreatic insulinoma, medullary thyroid cancer, Medulloblastoma, melanoma, mesothelioma, multiple myeloma muscle cancer, neoplasms of the endocrine or exocrine pancreas, neuroblastoma, ovarian cancer, Paget's Disease of the Nipple, pancreatic cancer, papillary thyroid cancer, Phyllodes Tumors, premalignant skin lesions, primary thrombocytosis, prostate cancer (e.g. castration-resistant prostate cancer) rhabdomyosarcoma, salivary gland cancer, sarcoma, soft tissue sarcoma, squamous cell carcinoma (e.g., head, neck, or esophagus), stomach cancer, testicular cancer, thyroid cancer, urinary bladder cancer, or uterine cancer. In embodiments, the cancer is selected from bladder cancer, breast cancer, colon cancer, esophageal cancer, esophageal cancer, glioblastoma, liver cancer, lung cancer, ovarian cancer, pancreatic cancer, prostate cancer, salivary gland cancer, soft tissue sarcoma, squamous cell lung carcinoma, stomach cancer, and uterine cancer.

ecDNA mediates an important and clinically distinct mechanism of resistance to targeted therapies. There are immediate therapeutic opportunities for utility of the one or more Chk1 inhibitor described herein as a single agent or in combination with other therapies. In some embodiments, the one or more Chk1 inhibitor described herein may be used to treat an ecDNA+ cancer, ecDNA+ tumor or ecDNA+ tumor cells. One or more Chk1 inhibitor described herein may be used to treat tumors, such as with one or more amplified oncogenes (e.g. FGFR, EGFR, MET, KRAS, MDM2 amplifications), in some cases, the one or more amplified oncogenes comprise non-mutant forms of the oncogene and in some cases, the amplified oncogenes comprises mutant forms of the oncogenes. One or more Chk1 inhibitor described herein may be used to treat tumors for which there are no approved targeted therapies or for which highly efficacious therapies are lacking. One or more Chk1 inhibitor described herein may be used to treat tumors that have developed resistance to another therapy such as a resistance to a targeted agent. In some cases, a tumor (or tumor cells) treated with one or more targeted agents develops resistance to a targeted agent, such as a targeted agent directed to an oncogene or a targeted agent that directly inhibits activating mutant forms of certain oncoproteins (e.g. KRAS, BRAF, EGFR) or as a consequence of focal amplification such as ecDNA-based amplification of the target gene itself, and the one or more Chk1 inhibitor described herein may be used to treat such tumors or tumor cells.

Provided herein are methods wherein inhibition of Chk1 by the one or more Chk1 inhibitors described herein exhibits synthetic lethality with a cancer-targeted agent. In some embodiments, synthetic lethality arises with one or more Chk1 inhibitors described herein in combination with a cancer targeted agent. In some cases, a tumor background is identified as hyper-sensitive to a Chk1 inhibitor and allows a sufficient therapeutic index to enable tolerated doses that are efficacious. In some embodiments, synthetic lethality arises with one or more Chk1 inhibitors described herein in combination with a cancer targeted agent where the tumor or tumor cells are ecDNA+. In some cases, Chk1 inhibition results in reduced ecDNA copy number. In some cases, Chk1 inhibition results in enhanced cytotoxicity in ecDNA+ cells. In some cases, enhanced cytotoxicity results from the combination of Chk1 inhibition and inhibition of a cancer-target, such as an oncogene.

In an aspect of methods herein, a tumor or tumor cells to be treated are ecDNA+. In some cases, such tumor or tumor cells are determined to have an ecDNA signature. In some cases, a tumor or tumor cells are determined to have an ecDNA signature when the tumor or tumor cells have one or more characteristics associated with ecDNA+ tumors or tumor cells. For example, in some cases, the ecDNA signature is selected from the group consisting of a gene amplification; a p53 loss of function mutation; absence of microsatellite instability (MSI-H); a low level of PD-L1 expression; a low level of tumor inflammation signature (TIS); a low level of tumor mutational burden (TMB); an increased frequency of allele substitutions, insertions, or deletions (indels); and any combination thereof.

Combination Therapy

In certain instances, the compound described herein, or a pharmaceutically acceptable salt, solvate, tautomer, or stereoisomer thereof, is administered in combination with a second therapeutic agent or a cancer-targeted agent.

In an aspect of methods herein, the method further comprises administering a cancer-targeted therapeutic agent, directed to an activity of a protein product of a target gene. In some cases, the treatment with the cancer-targeted therapeutic agent and the Chk1 inhibitor disclosed herein reduces amplification or expression of the target gene in the tumor or tumor cells. In some cases, the cancer-targeted therapeutic agent is administered prior to the Chk1 inhibitor. In some cases, the cancer-targeted therapeutic agent is administered concurrently with the Chk1 inhibitor.

In an aspect of methods herein, the tumor or tumor cells have an ecDNA signature. In some cases, the tumor or tumor cells develop the ecDNA signature after administration of the cancer-targeted therapeutic agent. In some cases, the tumor or tumor cells develop the ecDNA signature prior to treatment. In some cases, the method prevents an increase of ecDNA in the tumor or tumor cells.

In some embodiment, the second therapeutic agent or the cancer-targeted agent includes antimetabolites, platinum drugs, plant alkaloid drugs, and molecular targeting drugs.

In some embodiment, the second therapeutic agent the cancer-targeted agent includes DNA-damaging agents.

In some embodiment, the second therapeutic agent includes a radiation therapy.

In some embodiments, the antimetabolites include 5-fluorouracil, 5-fluoro-2'-deoxyuridine, tegafur, tegafur-uracil, tegafur-gimeracil-oteracil, pemetrexed, trifluridine, trifluridine-tipiracil hydrochloride, fludarabine (or an active metabolite fludarabine nucleoside), cytarabine, gemcitabine, capecitabine, nelarabine, clofarabine, and DNA methylation inhibitors (decitabine, guadecitabine, azacitidine, etc.).

In some embodiments, the platinum drugs include cisplatin, oxaliplatin, carboplatin, and nedaplatin.

In some embodiments, the plant alkaloid drugs include microtube inhibiting drugs such as paclitaxel, docetaxel, vinblastine, vincristine, vindesine, vinorelbine, and eribulin, and topoisomerase inhibiting drugs such as irinotecan (or an active metabolite SN-38), nogitecan, and etoposide.

In some embodiments, the molecular targeting drugs include ATR (ataxia telangiectasia and Rad3 related protein) inhibitors, AXL inhibitors, BRAF inhibitors, CDK4/6 inhibitors, other Chk1 (checkpoint kinase 1) inhibitors, CSF1R (colony-stimulating factor 1 receptor) inhibitors, EGFR (epidermal growth factor receptor) inhibitors, FGFR (fibroblast growth factor receptor) inhibitors, FLT3 (fms-related tyrosine kinase 3) inhibitors, HER2 inhibitors, HSP (heat shock protein) 90 inhibitors, KIT inhibitors, KRAS inhibitors, KRAS inhibitors, MDM2 (murine double minute 2) inhibitors, MDM4 (murine double minute 4) inhibitors, MET inhibitors, MYC inhibitors, PARP (poly ADP ribose polymerase) inhibitors, PDGFR (platelet-derived growth factor receptor) inhibitors, RET inhibitors, RNR (ribonucleotide reductase) inhibitors, TIE2 (tunica interna endothelial cell kinase 2) inhibitors, TRK inhibitors, VEGFR (vascular endothelial growth factor receptor) inhibitors, and Wee1 inhibitors.

In some embodiments, the ATR inhibitors include ART-0380, ATRN-119, ATRN-212, AZ-20, AZZ-6738, BAY-1895344, berzosertib (M-6620), BKT-300, IMP-9064, M-1774, M-4344 (VX-803), M-6620, nLs-BG-129, NU-6027, RP-3500, SC-0245, VE-822, and VX-970.

In some embodiments, the AXL inhibitors include cabozantinib and gilteritinib.

In some embodiments, the BRAF inhibitors include ASN-003, AZ-304, AZ-628, DP-2874, EBI-907, EBI-945, GDC-0879, LYN 204, NMS-P285, NMS-P730, PF-04880594, TL-241, UAI-201, and UB-941. In some embodiments, the BRAF inhibitors include ABM-1310, agerafenib (RXDX-105), ARQ-736, BAL-3833, belvarafenib, BGB-3245, BI-882370, DAY101, lifirafenib, LUT-014, PF-07284890, PLX-8394, RX-208, VS-6766, and XL-281. In some embodiments, the BRAF inhibitors include dabrafenib, encorafenib, and vemurafenib.

In some embodiments, the CDK4/6 inhibitors include AG-122275, AM-5992, AU2-94, IIIM-985, IIIM-290, GW-491619, HEC-80797, MM-D37K, MS-140, NP-102, QHRD-110, R-547, RGB-286199, RGT-419B, riviciclib, RO-0505124, THR-53, THR-79, TQB-3303, TY-302, VS2-370, XH-30002, and WXWH-0240. In some embodiments, the CDK4/6 inhibitors include auceliciclib, AT-7519, BEBT-209, BPI-1178, BPI-16350, CS-3002, fascaplysin, FCN-437, FN-1501, GLR-2007, HS-10342, lerociclib, milciclib maleate, NUV-422, ON-123300, PF-06842874, PF-06873600, PF-07220060, SHR-6390, TQB-3616, TY-302, voruciclib, and XZP-3287. In some embodiments, the CDK4/6 inhibitors include abemaciclib, palbociclib, ribociclib, and trilaciclib.

In some embodiments, the other Chk1 inhibitors include AZD-7762, BEBT-260, GDC-0575, LY-2880070, PF-477736, prexasertib, rabusertib (LY-2603618), RG-7602, SCH-900776, SRA737, and XCCS-605B.

In some embodiments, the CSF1R inhibitors include ARRY-382, BLZ-945, and sunitinib.

In some embodiments, the EGFR inhibitors include small molecule inhibitors such as APL-1898, BDTX-1535, BLU-701, BPI-361175, CH-7233163, DS-2087, E-IOC, FWD-1509, IN-A008, JS-111, JS-113, LL-191, LYN 205, neptinib, NT-004, ORIC-114, PRB-001, SIM-200, TGRX-360, WJ-13404, yinlitinib maleate, and ZSP-0391, and anti-EGFR antibodies such as 705, 707, ABX-900, CMAB-017, GB-263, KN-023, SSGJ-612, and SHR-A1307. In some embodiments, the EGFR inhibitors include small molecule inhibitors such as abivertinib, alflutinib mesylate, agerafenib (RXDX-105), ASK-120067, BBT-176, BDTX-189, BEBT-109, befortinib mesylate, beitatini, BPI-7711, BPI-D0316, BLU-945, CK-101, dositinib, DFP-17729, DZD-9008, epertinib, epitinib (HMPL-813), ES-072, FCN-411, FHND-9041, furmonertinib, GMA-204, Hemay-022, JRF-103, KP-673, larotinib, lazertinib, maihuatinib, marizomib, mobocertinib, naputinib tosilate, nazartinib, NRC-2694-A, OBX1-012, olafertinib, olmutinib, oritinib, pirotinib, poziotinib, SPH-1188, tarloxotinib, theliatinib (HMPL-309), TAS-6417, TPC-064, TQB-3804, TY-9591, WSD-0922, XZP-5809, YK-029A, YZJ-0318, and zorifertinib, and anti-EGFR antibodies such as 602, C-005, CDP1, depatuxizumab, E01001, GC-1118A, GR-1401, HLX-07, HS-627, I-010, imgatuzumab, JMT-101, JZB-28, KN-026, MP-0274, QL-1203, SCT-200, serclutamab, SYN-004, and TAD-011. In some embodiments, the EGFR inhibitors include small molecule inhibitors such as afatinib, amivantamab, aumolertinib (almonertinib), dacomitinib, erlotinib, gefitinib, icotinib, lapatinib, osimertinib, and pyrotinib, and anti-EGFR antibodies such as cetuximab, necitumumab, nimotuzumab, and panitumumab.

In some embodiments, FGFR inhibitors include small molecule inhibitors such as ABSK-012, ABSK-061, AST-56100, BIO-1262, BGS-2219, EVT-601, FPI-1966, JAB-6000, KIN-3248, SAR-439115, SC-0011, and WXSH-0011, and anti-FGFR antibodies such as M-6123, OM-RCA-001. In some embodiments, FGFR inhibitors include small molecule inhibitors such as 3D-185, ABSK-011, ABSK-091, aldafermin, alofanib, AZD-4547, BFKB-8488A, BPI-17509, BPI-43487, CPL-304-110, derazantinib, E-7090, EVER-4010001, FGF-401, fisogatinib, futibatinib, gunagratinib, H3B-6527, HH-185, HMPL-453, HS-236, ICP-105, ICP-192, infigratinib, MAX-40279, RLY-4008, rogaratinib, SAR-442501, SY-4798, TT-00434, and zoligratinib (FF-284), and anti-FGFR antibodies such as bemarituzumab. In some embodiments, FGFR inhibitors include small molecule inhibitors such as erdafitinib and pemigatinib.

In some embodiments, the FLT3 inhibitors include cabozantinib, gilteritinib, midostaurin, sorafenib, and sunitinib.

In some embodiments, the HER2 inhibitors include small molecule inhibitors such as LL-191, NT-004, SPH-3261, and VRN-10, and anti-Her2 antibodies such as 704, 706, AbGn-110, ACE-1702, ALL-C-2137, ANT-043, AT-501, ATV:HER2, BSI-001, GB-251, Herceptarg, HK-001, IGEM-H, KL-A166, KM-254, KM-257, LIN-001, LIN-002, MI-180021, SHR-A1811, SSGJ-612, VB7-756, ZV-0201. In some embodiments, the HER2 inhibitors include small molecule inhibitors such as AR-788, BDTX-189, DZD-1516, epertinib, JRF-103, larotinib, maihuatinib, mobocertinib, NRC-2694-A, pirotinib, poziotinib, tarloxotinib, TAS-0728, and ZN-A-1041, and anti-Her2 antibodies such as AC-101, ARX-788, B00-2, BAT-1006, BAY-2701439, BCD-147, DAC-001, disitamab vedotin, DP-303c, E01001, GP-2, GQ-1001, HLX-22, KN-026, LCB-14, MB-103, MBS-301, MRG-002, MRT-201, MP-0273, PF-06804103, QL-1209, TAA-013, WLB-301, zanidatamab, zenocutuzumab, and ZW-49. In some embodiments, the HER2 inhibitors include small molecule inhibitors such as afatinib, dacomitinib, lapatinib, neratinib, pyrotinib, and tucatinib, and anti-Her2 antibodies such as margetuximab, pertuzumab, and trastuzumab.

In some embodiments, the HSP90 inhibitors include ganetespib, luminespib, and onalespib.

In some embodiments, the KIT inhibitors include lenvatinib, midostaurin, pazopanib, sorafenib, and sunitinib.

In some embodiments, the KRAS include small molecule inhibitors such as ABREV01, ARS-1620, APG-1842, ATG-012, BBP-454, BEPT-607, BI-2852, BI-1823911, BPI-421286, BTX-2541, COT1-219, IMM-1811900, JAB-21000, JAB-22000, JAB-23000, JAB-BX300, JP-002, KR-12, LYN 202, MRTX-1133, RAS-F, RMC-6236, RMC-6291, SDGR 5, STX-301, and YL-15293, and anti-KRAS antibodies such as SBT-100, SBT-102, and SBT-300. In some embodiments, the KRAS include small molecule inhibitors such as adagrasib, ARS-3248, D-1553, GDC-6036, JDQ-443, LY3537982, sotorasib (AMG 510), and BI 1701963.

In some embodiments, MDM2 inhibitors include AD-021.32, CYC700, DS-5272, MI-1061, MI-219, MI-43, MD-224, MK-8242, NU-8231, OM-301, PXN-527, Rigel-3, RO-2468, RO-5353, RO-5963, and SIL-43. In some embodiments, MDM2 inhibitors include ALRN-6924, APG-115, ASTX-295, ATSP-7041, BI-907828, CGM-097, idasanutlin, KRT-232 (AMG-232), MI-77301 (SAR405838, SAR299155), NVP-CGM097, RAIN-32 (milademetan), RG7112 (RO5045337), RG7388 (RG7775), serdemetan (JNJ-26854165), siremadlin, and UBX-0101.

In some embodiments, the MDM4 inhibitors include 17AAG, 489-PXN, CTX1, FL-118, Inulanolide A, K-178, and SAH-p53-8. In some embodiments, the MDM4 inhibitors include APG-115, ALRN-6924, ATSP-7041, and BI-907828.

In some embodiments, the MET small molecule inhibitors such as ABP-1130, BPI-1831, BPI-2021, BYON-3521, CG-203306, CX-1003, Debio-1144, EMD-94283, EMT-100, EMT-101, HE-003, LMV-12, LS-177, NX-125, OMO-2, PF-4254644, PRX-MET, PTX-2173, QBH-196, RP-1400, SAB-Y14, SAR-125844, SGX-126, SYD-3521, WXSH-0011, X-379, and XL-265, and anti-MET antibodies such as ABX-900, GB-263, FS-101, LY-3164530, LY-3343544, PMC-002, and SAIT-301. In some embodiments, the MET small molecule inhibitors such as ABN-401, ABT-700, AMG-208, AMG-337, ARGX-111, BAY-85-3474, BMS-817378, bozitinib, BPI-9016M, glumetinib, golvatinib tartrate, GST-HG161, HQP-8361, I-020, JNJ-38877605, kanitinib, merestinib, MK-2461, MK-8033, OMO-1, pamufetinib, S-49076, savolitinib, SPH-3348, tivantinib, SAR-125844, SCR-1515, and TPX-0022, and anti-MET antibodies such as APL-101, CKD-702, EMB-01, EMI-137, ficlatuzumab, HLX-55, HS-10241, MCLA-129, MT-8633, NOV-1105, RC-108, REGN-5093, SHR-A1403, Sym-015, telisotuzumab vedotin. In some embodiments, the MET small molecule inhibitors such as amivantamab, capmatinib, crizotinib, and tepotinib.

In some embodiments, the PARP inhibitors include niraparib, olaparib, rucaparib, talazoparib, veliparib.

In some embodiments, the PDGFR inhibitors are PDGFRa and/or PDGFRO inhibitors and include lenvatinib, midostaurin, pazopanib, sorafenib, and sunitinib.

In some embodiments, the RET inhibitors include sunitinib, cabozantinib, sorafenib, lenvatinib, and vandetanib.

In some embodiments, the RNR inhibitors include 5-chloro-2-(n-((1S,2R)-2-(6-fluoro-2,3-dimethylphenyl)-1-(5-oxo-4,5-dihydro-1,3,4-oxadiazol-2-yl)propyl)sulfamoyl) benzamide, cladribine, clofarabine, COH29 (N-[4-(3,4-dihydroxyphenyl)-5-phenyl-1,3-thiazol-2-yl]-3,4-dihydroxybenzamide), fluarabine, gemcitabine, hydroxyurea, motexafin gadolinium, osalmid, TAS1553, tezacitabine, and triapine.

In some embodiments, the TIE2 inhibitors include cabozantinib.

In some embodiments, the TRK inhibitors include cabozantinib and entrectinib.

In some embodiments, the VEGFR inhibitors are inhibitors of at least one of VEGFR1, VEGFR2, and VEGFR3 and include small molecule inhibitors such as sunitinib, cabozantinib, midostaurin, sorafenib, vandetanib, pazopanib, lenvatinib, and axitinib, and anti-VEGFR antibodies such as ramucirumab.

In some embodiments, Wee1 inhibitors include adavosertib, AZD1775 (MK1775), Bos-I, bosutinib, DC-859/A, Debio 0123, IMP7068, NUV-569, PD 407824, PD0166285, PDO166285, PD0407824, SC-0191, SDR-7778, SDR-7995, WEEI-IN-3, and ZN-c3.

In some embodiments, the benefit experienced by a patient is increased by administering one of the compounds described herein with a second therapeutic agent (which also includes a therapeutic regimen) that also has therapeutic benefit.

In one specific embodiment, a compound described herein, or a pharmaceutically acceptable salt, solvate, tautomer, or stereoisomer thereof, is co-administered with a second therapeutic agent, wherein the compound described herein, or a pharmaceutically acceptable salt, solvate, tautomer, or stereoisomer thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is additive of the two therapeutic agents or the patient experiences a synergistic benefit.

In certain embodiments, different therapeutically effective dosages of the compounds disclosed herein will be utilized in formulating a pharmaceutical composition and/or in treatment regimens when the compounds disclosed herein are administered in combination with a second therapeutic agent. Therapeutically effective dosages of drugs and other agents for use in combination treatment regimens are optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt, solvate, tautomer, or stereoisomer thereof, is initiated prior to, during, or after treatment with a second agent described herein, and continues until any time during treatment with the second agent or after termination of treatment with the second agent. It also includes treatments in which a compound described herein, or a pharmaceutically acceptable salt, solvate, tautomer, or stereoisomer thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g., the disease, disorder, or condition from which the subject suffers; the age, weight, sex, diet, and medical condition of the subject). Thus, in some instances, the dosage regimen employed varies and, in some embodiments, deviates from the dosage regimens set forth herein.

For combination therapies described herein, dosages of the co-administered compounds vary depending on the type of co-drug employed, on the specific drug employed, on the disease or condition being treated, and so forth. In additional embodiments, when co-administered with a second therapeutic agent, the compound provided herein is administered either simultaneously with the second therapeutic agent, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills, as a single infusion, or as two separate infusions).

The compounds described herein, or a pharmaceutically acceptable salt, solvate, tautomer, or stereoisomer thereof, as well as combination therapies, are administered before, during, or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, the compound described herein, or a pharmaceutically acceptable salt, solvate, tautomer, or stereoisomer thereof, is administered in combination with an adjuvant. In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced).

EXAMPLES

All final compounds were purified by either high-performance liquid chromatography (HPLC) or supercritical fluid chromatography (SFC) and were characterized by proton ($^1$H) NMR. All chemicals were purchased from commercial suppliers and used as received unless otherwise indicated. Proton nuclear magnetic resonance ($^1$H NMR) spectra were recorded on Bruker AVANCE 400 MHz spectrometers. Chemical shifts are expressed in δ ppm and are calibrated to the residual solvent peak (CDCl$_3$, 7.26 ppm; DMSO-d$_6$, 2.54 ppm). Coupling constants (J), when given, are reported in hertz. Multiplicities are reported using the following abbreviations: s=singlet, d=doublet, dd=doublet of doublets, t=triplet, q=quartet, n=multiplet (range of multiplet is given), br=broad signal, and dt=doublet of triplets. Carbon nuclear magnetic resonance ($^{13}$C NMR) spectra were recorded using a Bruker AVANCE HD spectrometer at 100 MHz. Chemical shifts are reported in δ ppm and are calibrated to the solvent peak: carbon (CDCl$_3$, 77.23 ppm).

All final compounds were purified by reverse phase HPLC or SFC. The purity for test compounds was determined by HPLC on a SHIMADZU LC-2010A HT instrument. HPLC conditions were as follows: XBRIDGE C18 column, 3.5 m, 2.1 mm×50 mm, water (+0.05% TFA): acetonitrile (+0.05% TFA), acetonitrile from 0 to 60% over 7 minutes, acetonitrile from 60% to 100% over 1 minute, flow rate 0.8 mL/min, UV detection (λ=214, 254 nm). Mass spectra were obtained using LCMS on a LCMS-Agilent 6125 instrument using electrospray ionization (ESI). LCMS conditions were as follows: Waters Cortecs C18+ column, 2.7 μm, 2.1 mm×30 mm; column temperature 45° C.; mobile phase, acetonitrile (+0.05% formic acid):water (+0.05% formic acid); gradient, 5% acetonitrile to 95% acetonitrile in 1.0 min, hold 1.0 min, total 2.5 min; flow rate 1.8 mL/min; UV detection (λ=214, 254 nm). Chiral purity for test compounds was determined using a Thar SFC prep 80 instrument.

Preparation P1-1: 5-((5-(2-Hydroxy-6-methoxyphenyl)-1H-pyrazol-3-yl)amino)pyrazine-2-carbonitrile

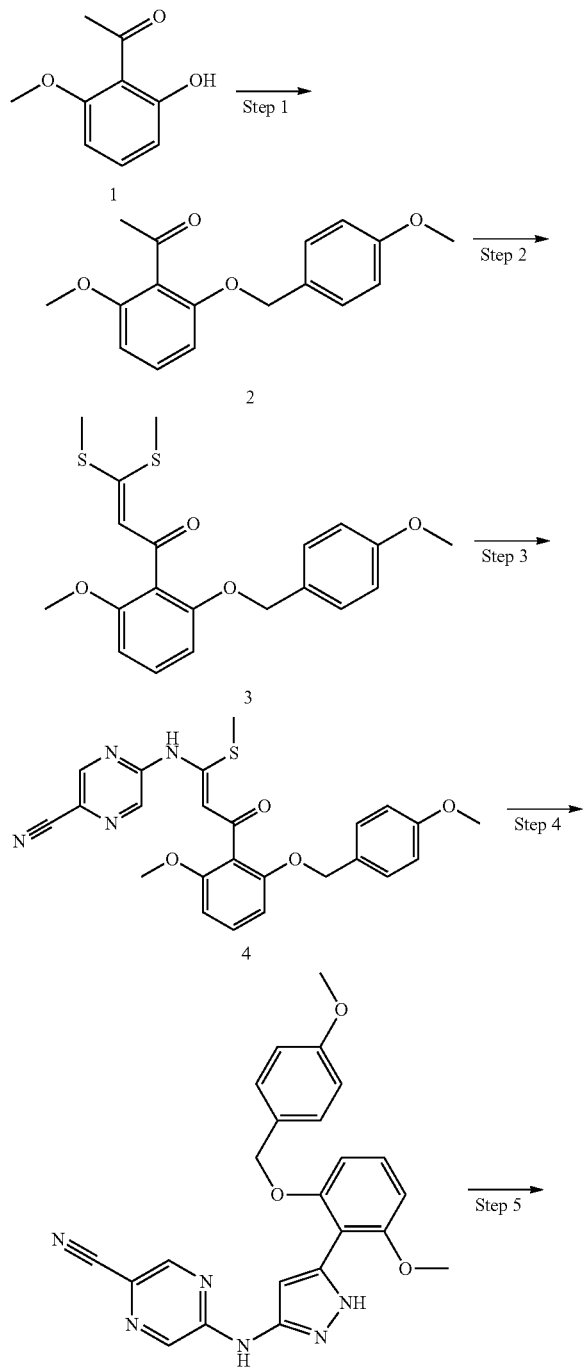

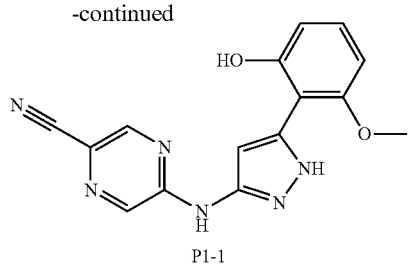

P1-1

Step 1: 1-(2-Methoxy-6-((4-methoxybenzyl)oxy)phenyl)ethan-1-one (2)

To a mixture of 1-(2-hydroxy-6-methoxyphenyl)ethan-1-one (10 g, 60.2 mmol) and potassium carbonate (16.64 g, 120.4 mmol) in anhydrous N,N-dimethylformamide (70 mL) at 0° C. was added 4-methoxybenzyl chloride (10.37 g, 66.2 mmol) dropwise over 10 minutes. The reaction mixture was heated to 35° C. for 18 hours. The reaction mixture was poured into ice water (350 mL) and the mixture was extracted with ethyl acetate (3×200 mL). The combined organic layers were washed with water (3×200 mL) and brine (300 mL), dried over sodium sulfate, filtered, and evaporated. The crude product was purified by gradient silica gel column chromatography to afford the title compound (15 g, 87% yield) as a white solid. LCMS: Rt=1.291 min, ESMS m/z=308.9 [M+Na]+.

Step 2: 1-(2-Methoxy-6-((4-methoxybenzyl)oxy)phenyl)-3,3-bis(methylthio)prop-2-en-1-one (3)

To a mixture of lithium tert-butoxide (8.71 g, 108.8 mmol) in anhydrous dimethyl sulfoxide (160 mL) was added 1-(2-methoxy-6-((4-methoxybenzyl)oxy)phenyl)ethan-1-one (14.5 g, 50.6 mmol) under nitrogen and the reaction mixture was stirred at room temperature for 30 minutes. To the reaction mixture was added carbon disulfide (4.82 g, 63.3 mmol) slowly over 10 minutes while maintaining the internal temperature below 30° C. The reaction mixture was stirred at room temperature for 1 hour. To the reaction mixture was added iodomethane (15.8 g, 111.3 mmol) slowly while maintaining the internal temperature below 30° C. The resulting mixture was stirred at room temperature for 5 hours. The reaction mixture was poured into ice water (600 mL) and the mixture was extracted with ethyl acetate (3×300 mL). The combined organic layers were washed with water (3×300 mL) and brine (300 mL), dried over sodium sulfate, filtered, and evaporated. The crude product was purified by gradient silica gel column chromatography to afford the title compound (18 g, 91% yield) as a yellow solid. LCMS: Rt=1.365 min, ESMS m/z=412.6 [M+Na]+.

Step 3: 5-((3-(2-Methoxy-6-((4-methoxybenzyl)oxy)phenyl)-1-(methylthio)-3-oxoprop-1-en-1-yl)amino)pyrazine-2-carbonitrile (4)

To a mixture of sodium hydride (60% dispersion in mineral oil, 1.54 g, 38.5 mmol) in anhydrous tetrahydrofuran (200 mL) was added 5-aminopyrazine-2-carbonitrile (3.69 g, 30.7 mmol) in four portions over 5 minutes at 0° C. under nitrogen. The reaction mixture was stirred for 45 minutes while allowing the mixture to warm to 5° C. To the reaction mixture was added 1-(2-methoxy-6-((4-methoxybenzyl)oxy)phenyl)-3,3-bis(methylthio)prop-2-en-1-one (10 g, 25.6 mmol) in portions. The resulting slurry was stirred at 5° C. for 5 minutes. The reaction mixture was heated to 66° C. for 8 hours. The reaction was quenched with ice water (300 mL) and the mixture was extracted with ethyl acetate (3×200 mL). The combined organic layers were washed with brine (200 mL), dried over sodium sulfate, filtered, and evaporated to afford the title compound (12 g, crude), which was used without purification. LCMS: Rt=1.386 min, ESMS m/z=462.7 [M+H]+.

Step 4: 5-((5-(2-Methoxy-6-((4-methoxybenzyl)oxy) phenyl)-1H-pyrazol-3-yl)amino)pyrazine-2-carbonitrile (5)

To a mixture of crude 5-((3-(2-methoxy-6-((4-methoxy-benzyl)oxy)phenyl)-1-(methylthio)-3-oxoprop-1-en-1-yl) amino)pyrazine-2-carbonitrile (12 g) and acetic acid (4.67 g, 77.6 mmol) in ethanol (150 mL) was added hydrazine hydrate (2.59 g, 51.8 mmol), resulting in a slight exotherm. The resulting yellow slurry was slowly heated to 70° C. and the reaction mixture was stirred at 70° C. for 6 hours under nitrogen. The thick slurry was slowly cooled to below 30° C. The precipitate was collected and the solid was washed with cold ethanol (200 mL). The product was dried under vacuum at 40° C. to afford the title compound (8 g, 73% yield over two steps) as a yellow solid. LCMS: Rt=1.313 min, ESMS m/z=428.7 [M+H]+.

Step 5: 5-((5-(2-Hydroxy-6-methoxyphenyl)-1H-pyrazol-3-yl)amino)pyrazine-2-carbonitrile (P1-1)

A solution of 5-((5-(2-methoxy-6-((4-methoxybenzyl) oxy)phenyl)-1H-pyrazol-3-yl)amino)pyrazine-2-carbonitrile (8 g, 18.7 mmol) and hydrogen chloride (4M in 1,4-dioxane, 80 mL, 320 mmol) was heated to 65° C. for 5 hours. The brown slurry was cooled to room temperature. The precipitate was collected and the solid was washed with ethyl acetate (150 mL) to afford the title compound as the dihydrochloride salt (7 g, 18.4 mmol). The product (7 g) was suspended in tetrahydrofuran (100 mL). To the mixture was added triethylamine (4.65 g, 46 mmol) and the resulting slurry was stirred at room temperature for 2 hours. The mixture was filtered and the filtrate was evaporated. The residue was suspended in diethyl ether (20 mL) and the mixture was stirred at room temperature for 30 minutes. The precipitate was collected to afford the title compound (5 g, 87% yield) as a yellow solid. LCMS: Rt=1.160 min, ESMS m/z=308.8 [M+H]−. 1H NMR (400 MHz, DMSO-d6) δ ppm 10.83 (s, 1H), 8.65 (s, 1H), 8.56 (s, 1H), 7.15 (t, J=8.4 Hz, 1H), 6.86 (s, 1H), 6.61 (d, J=8.4 Hz, 1H), 6.58 (d, J=8.4 Hz, 1H), 3.79 (s, 3H).

The following compounds were prepared by the same general method:

| Ex. | Structure | MW | LC-MS (m/z) |
|---|---|---|---|
| P1-2 | | 278.1 | 278.9 |
| P1-3 | 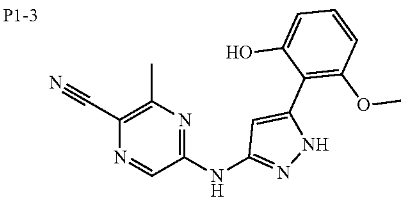 | 322.1 | 323.1 |
| P1-4 | 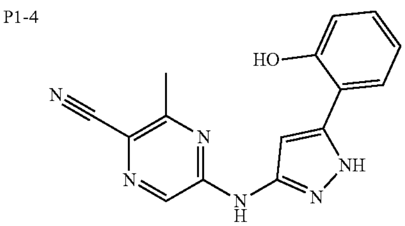 | 292.1 | 293.0 |

Preparation P2-1: 1-(2-((4-Methoxybenzyl)oxy)-6-(2,2,2-trifluoroethoxy)phenyl)ethan-1-one

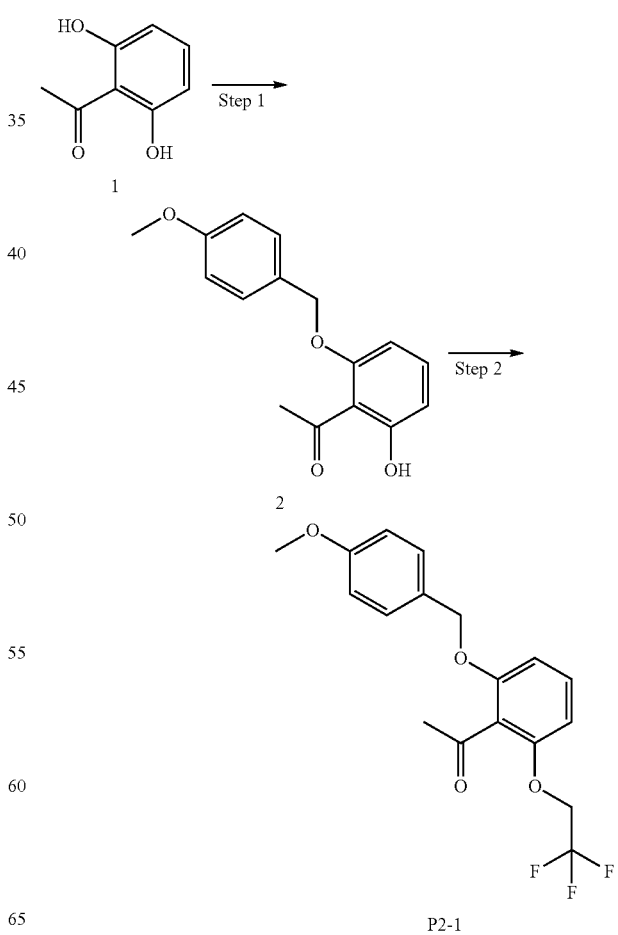

Step 1: 1-(2-Hydroxy-6-((4-methoxybenzyl)oxy) phenyl)ethan-1-one (2)

To a mixture of 1-(2,6-dihydroxyphenyl)ethan-1-one (10 g, 65.7 mmol) and 4-methoxybenzyl alcohol (9.08 g, 65.7 mmol) in N,N-dimethylformamide (50 mL) was added potassium carbonate (8.16 mL, 72.3 mmol) at room temperature. The reaction mixture was heated to 30° C. for 18 h. The reaction mixture was poured into water (100 mL) and extracted with ethyl acetate (3×100 mL). The combined organic layers were washed with brine (100 mL), dried over sodium sulfate, filtered, and evaporated. The residue was purified by gradient silica gel column chromatography to afford the title compound (11 g, 52% yield) as a yellow solid. LCMS: Rt=1.398 min, ESMS m/z=294.8. [M+Na]$^+$.

Step 2: 1-(2-((4-Methoxybenzyl)oxy)-6-(2,2,2-trifluoroethoxy)phenyl)ethan-1-one (P2-1)

To a mixture of 1-(2-hydroxy-6-((4-methoxybenzyl)oxy) phenyl)ethan-1-one (28 g, 102.8 mmol) and 1,1,1-trifluoro-2-iodoethane (30.21 g, 143.9 mmol) in N,N-dimethylformamide (100 mL) was added potassium carbonate (25.57 g, 185 mmol) at room temperature. The reaction mixture was heated to 100° C. for 18 h. The reaction mixture was poured into water (200 mL) and extracted with ethyl acetate (3×300 mL). The combined organic layers were washed with brine (300 mL), dried over sodium sulfate, filtered, and evaporated. The residue was purified by gradient silica gel column chromatography to furnish the title compound (12.57 g, 33% yield) as a white solid. LCMS: Rt=1.393 min, ESMS m/z=376.7 [M+H]$^+$.

The following compounds were prepared by the same general method:

| Ex. | Structure | MW | LC-MS (m/z) |
|---|---|---|---|
| P2-2 | 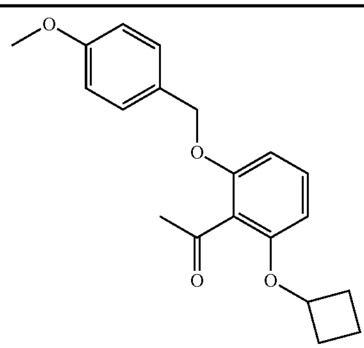 | 326.2 | 349.1 |
| P2-3 | 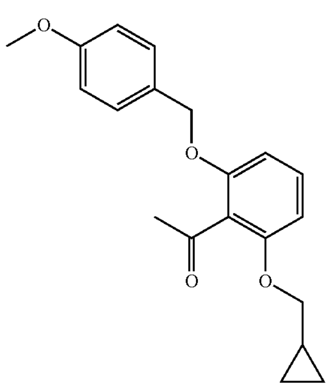 [SMILES: COc1ccc(COc2cccc(OCC3CC3)c2C(C)=O)cc1] | 326.2 | 349.0 |

Preparation P3-1: 1-(4-Fluoro-2-methoxy-6-((4-methoxybenzyl)oxy)phenyl)ethan-1-one

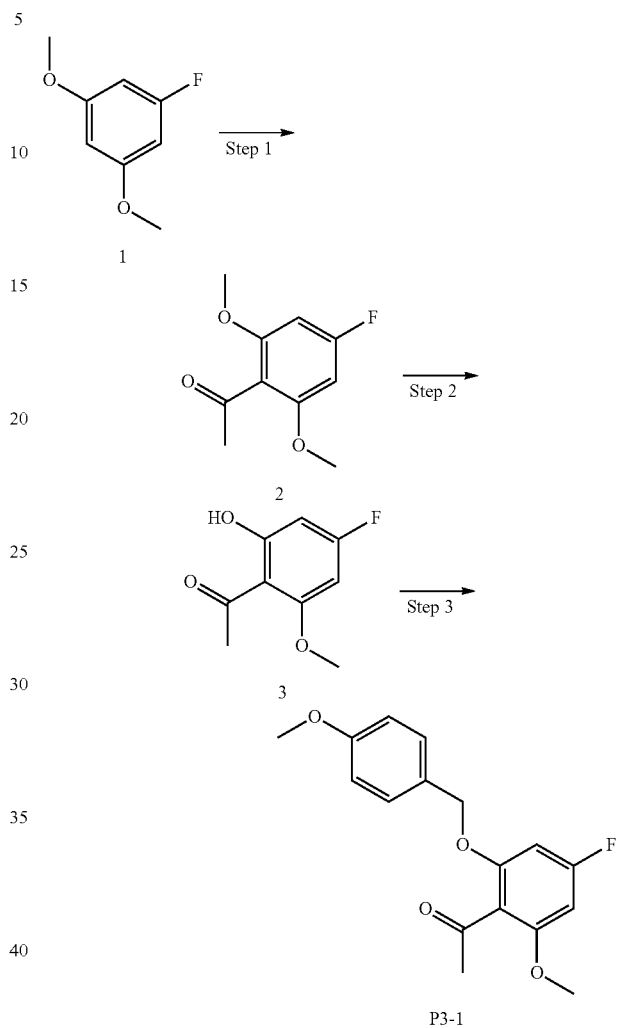

Step 1: 1-(4-Fluoro-2,6-dimethoxyphenyl)ethan-1-one (2)

To a solution of aluminum trichloride (17.15 g, 127.9 mmol) in toluene (80 mL) was added 1-fluoro-3,5-dimethoxybenzene (20 g, 128 mmol) at 0° C. The reaction mixture was stirred at 0° C. for 2 h. To the reaction mixture was added acetyl chloride (9.06 mL, 128.2 mmol) at 0° C. and the reaction mixture was stirred at 0° C. for 30 min. The reaction mixture was evaporated and the residue was purified by gradient silica gel column chromatography to afford the title compound (9.6 g, 38% yield) as a yellow solid. LCMS: Rt=1.090 min, ESMS m/z=199.1 [M+H]$^+$.

Step 2: 1-(4-Fluoro-2-hydroxy-6-methoxyphenyl) ethan-1-one (3)

To a mixture of 1-(4-fluoro-2,6-dimethoxyphenyl)ethan-1-one (3.1 g, 15.6 mmol) in dichloromethane (30 mL) was added boron tribromide (2.25 mL, 23.4 mmol) at −20° C. and the reaction mixture was stirred for 1 h. The reaction mixture was evaporated and the residue was purified by gradient silica gel column chromatography to afford the title compound (2.6 g, 90% yield) as a yellow oil. LCMS: Rt=1.305 min, ESMS m/z=184.9 [M+H]⁺.

Step 3: 1-(4-Fluoro-2-methoxy-6-((4-methoxybenzyl)oxy)phenyl)ethan-1-one (P3-1)

To a mixture of 1-(4-fluoro-2-hydroxy-6-methoxyphenyl)ethan-1-one (2.6 g, 14.1 mmol) and 4-methoxybenzyl chloride (2.25 mL, 16.9 mmol) in anhydrous N,N-dimethylformamide (20 mL) at 0° C. was added potassium carbonate (2.33 g, 16.9 mmol). The reaction mixture was warmed to room temperature and stirred for 18 h. The reaction was quenched with water (20 mL) and the mixture was extracted with ethyl acetate (3×20 mL). The combined organic layers were dried over sodium sulfate, filtered, and evaporated. The crude product was purified by gradient silica gel column chromatography to afford the title compound (3.8 g, 65% yield) as a colorless oil. LCMS: Rt=1.237 min, ESMS m/z=327.1 [M+Na]⁺.

The following compounds were prepared by the same general method:

| Ex. | Structure | MW | LC-MS (m/z) |
|---|---|---|---|
| P3-2 | 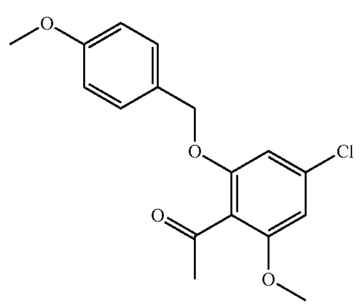 [SMILES: COc1ccc(COc2cc(Cl)cc(OC)c2C(C)=O)cc1] | 320.1 | 342.7 |
| P3-3 | 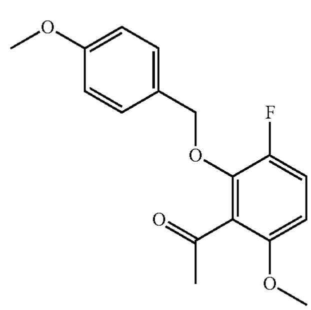 | 304.1 | 326.7 |

Preparation P4-1: 1-(3-((4-Methoxybenzyl)oxy)-6-methylpyridin-2-yl)ethan-1-one

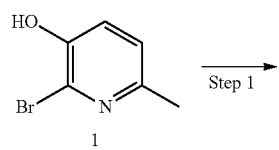

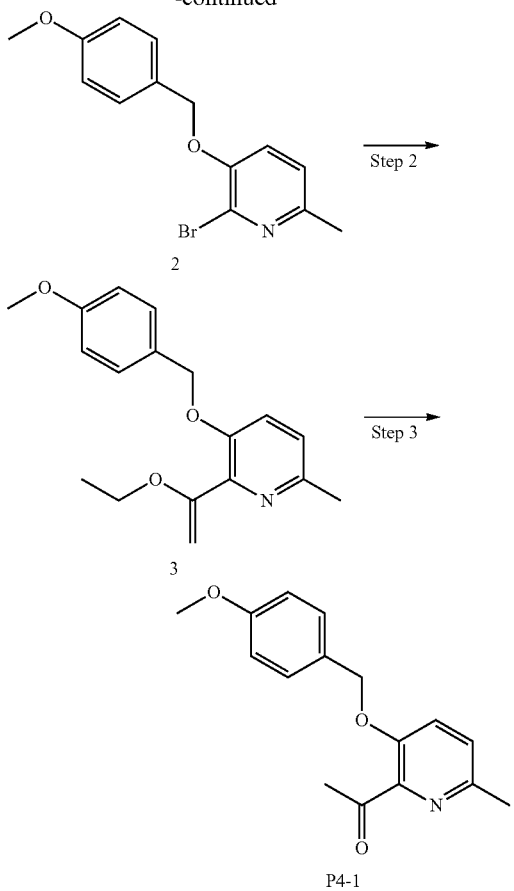

Step 1: 2-Bromo-3-((4-methoxybenzyl)oxy)-6-methylpyridine (2)

To a solution of 2-bromo-6-methylpyridin-3-ol (15 g, 79.8 mmol) and potassium carbonate (27.6 g, 199.5 mmol) in N,N-dimethylformamide (100 mL) was added 4-methoxybenzyl chloride (13 mL, 95.8 mmol) and the reaction mixture was stirred at room temperature for 16 h. The reaction mixture was diluted with ethyl acetate (100 mL), washed with brine (300 mL) and evaporated. The residue was purified by gradient silica gel column chromatography to give the title compound (22 g, 81% yield) as an off-white solid. LCMS: Rt=1.135 min, ESMS m/z=308.0 [M+H]⁺.

Step 2: 2-(1-Ethoxyvinyl)-3-((4-methoxybenzyl)oxy)-6-methylpyridine (3)

To a solution of 2-bromo-3-((4-methoxybenzyl)oxy)-6-methylpyridine (6.6 g, 21.4 mmol) and tributyl(1-ethoxyethenyl)stannane (15.46 g, 42.8 mmol) in toluene (50 mL) was added tetrakis(triphenylphosphine)palladium(0) (7.42 g, 6.42 mmol) and the reaction mixture was stirred at 100° C. for 16 h under nitrogen. The reaction mixture was evaporated and the residue was purified by gradient silica gel column chromatography to give the title compound (6.0 g, 84% yield) as a colorless oil. LCMS: Rt=1.144 min, ESMS m/z=300.0 [M+H]⁺.

Step 3: 1-(3-((4-Methoxybenzyl)oxy)-6-methylpyridin-2-yl)ethan-1-one (P4-1)

To a solution of 2-(1-ethoxyvinyl)-3-((4-methoxybenzyl)oxy)-6-methylpyridine (6.0 g, 20 mmol) in acetonitrile (20 mL) was added 1 N hydrochloric acid (50 mL, 50 mmol) and the reaction mixture was stirred at room temperature for 2 h. The mixture was neutralized (pH 7) by addition of solid sodium bicarbonate. The mixture was evaporated and the residue was purified gradient silica gel column chromatography to furnish the title compound (2.0 g, 33% yield) as an off-white solid. LCMS: Rt=1.332 min, ESMS m/z=272.0 [M+H]$^+$.

Preparation P5-1: 5-((5-(2-Fluoro-6-hydroxyphenyl)-1H-pyrazol-3-yl)amino)pyrazine-2-carbonitrile

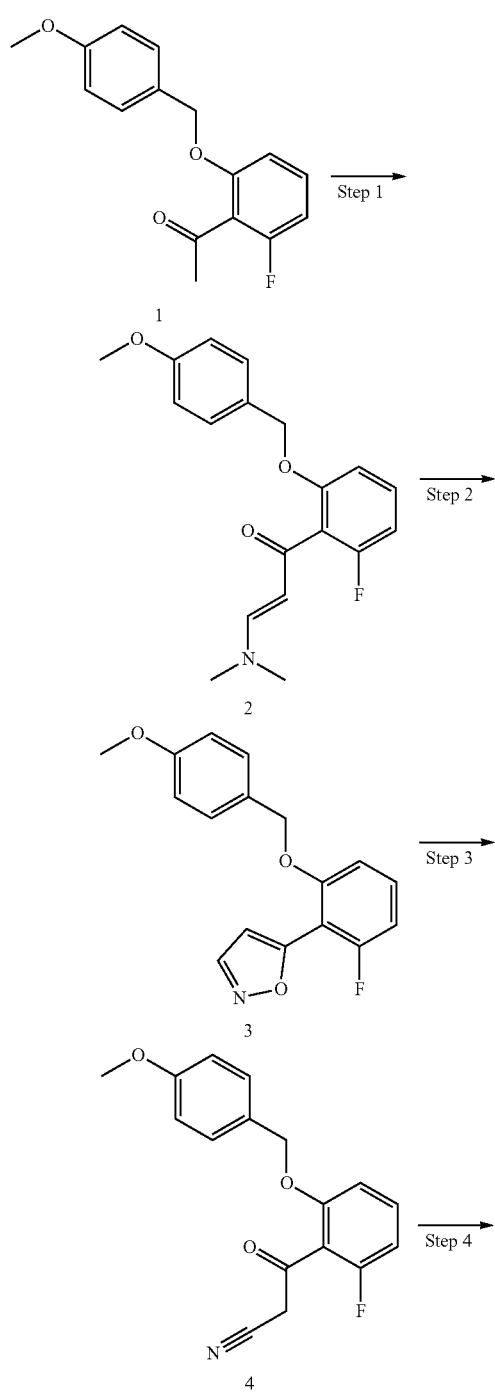

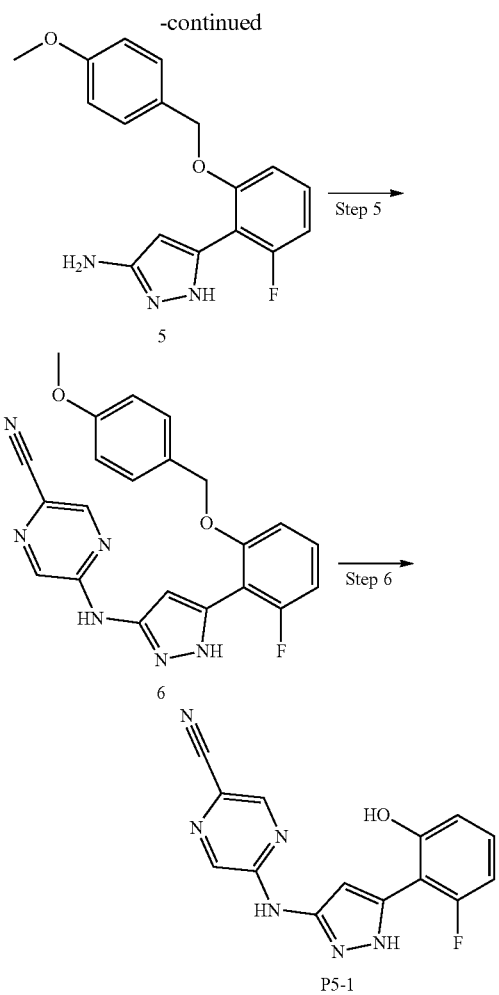

Step 1: 3-(Dimethylamino)-1-(2-fluoro-6-((4-methoxybenzyl)oxy)phenyl)prop-2-en-1-one (2)

A mixture of 1-(2-fluoro-6-((4-methoxybenzyl)oxy)phenyl)ethan-1-one (5 g, 18.24 mmol) and N,N-dimethylformamide dimethylacetal (9.69 mL, 73.0 mmol) in anhydrous N,N-dimethylformamide (40 mL) was heated to 80° C. for 3 h. The reaction mixture was evaporated to afford the crude title compound (6.5 g) as a yellow oil, which was used without purification. LCMS: Rt=1.205 min, ESMS m/z=329.8 [M+H]$^+$.

Step 2: 5-(2-Fluoro-6-((4-methoxybenzyl)oxy)phenyl)isoxazole (3)

A mixture of crude 3-(dimethylamino)-1-(2-fluoro-6-((4-methoxybenzyl)oxy)phenyl)prop-2-en-1-one (5.85 g, 17.78 mmol) and hydroxylamine hydrochloride (1.35 g, 19.6 mmol) in anhydrous ethanol (60 mL) was stirred at 40° C. for 3 h under nitrogen. The mixture was diluted with water (50 mL) and extracted with ethyl acetate (3×30 mL). The combined organic layers were dried over sodium sulfate, filtered, and evaporated. The crude product was taken up in ethyl acetate (20 mL). To the solution was added petroleum ether (30 mL). The precipitate was collected and the solid was dried at 40° C. under vacuum to afford the title compound (4.5 g, 82% yield over 2 steps) as a yellow solid. LCMS: Rt=1.258 min, ESMS m/z=300.1 [M+H]⁺.

Step 3: 3-(2-Fluoro-6-((4-methoxybenzyl)oxy)phenyl)-3-oxopropanenitrile (4)

A mixture of 5-(2-fluoro-6-((4-methoxybenzyl)oxy)phenyl)isoxazole (1 g, 3.34 mmol) and potassium hydroxide (156 mg, 5.02 mmol) in anhydrous ethanol (10 mL) was stirred at 50° C. for 1 h under nitrogen. The reaction mixture was evaporated and the residue was taken up in water (20 mL). The mixture was acidified to pH 5 by addition of saturated citric acid solution. The mixture was extracted with ethyl acetate (3×20 mL). The combined organic layers were dried over sodium sulfate, filtered, and evaporated to give the crude title compound (900 mg) as a yellow solid, which was used without further purification. LCMS: Rt=1.180 min, ESMS m/z=322.1 [M+Na]⁺.

Step 4: 5-(2-Fluoro-6-((4-methoxybenzyl)oxy)phenyl)-1H-pyrazol-3-amine (5)

A mixture of crude 3-(2-fluoro-6-((4-methoxybenzyl)oxy)phenyl)-3-oxopropanenitrile (900 mg), hydrazine hydrate (1.22 mL, 18.06 mmol) and acetic acid (688 µL, 12.04 mmol) in anhydrous ethanol (10 mL) was slowly heated to 80° C. and the reaction mixture was stirred at 80° C. for 18 h under nitrogen. The reaction mixture was evaporated and the crude product was purified by gradient silica gel column chromatography to afford the title compound (900 mg, 86% yield over 2 steps) as a yellow solid. LCMS: Rt=1.017 min. ESMS m/z=314.1 [M+H]⁺.

Step 5: 5-((5-(2-Fluoro-6-((4-methoxybenzyl)oxy)phenyl)-1H-pyrazol-3-yl)amino)pyrazine-2-carbonitrile (6)

To a mixture of 5-(2-fluoro-6-((4-methoxybenzyl)oxy)phenyl)-1H-pyrazol-3-amine (1 g, 3.19 mmol) and 5-chloropyrazine-2-carbonitrile (533 mg, 3.83 mmol) in dimethyl sulfoxide (10 mL) was added 4-ethylmorpholine (1.21 mL, 9.57 mmol) and the reaction mixture was stirred at 80° C. for 3 h. The reaction mixture was cooled to room temperature and diluted with water (20 mL). The mixture was extracted with ethyl acetate (3×20 mL) and the combined organic layers were dried over sodium sulfate, filtered, and evaporated. The crude product was purified by gradient silica gel column chromatography to afford the title compound (600 mg, 45% yield) as a yellow solid. LCMS: Rt=1.196 min. ESMS m/z=417.1 [M+H]⁺.

Step 6: 5-((5-(2-Fluoro-6-hydroxyphenyl)-1H-pyrazol-3-yl)amino)pyrazine-2-carbonitrile (P5-1)

A solution of 5-((5-(2-fluoro-6-((4-methoxybenzyl)oxy)phenyl)-1H-pyrazol-3-yl)amino)pyrazine-2-carbonitrile (560 mg, 1.89 mmol) and hydrogen chloride (4M in 1,4-dioxane, 5 mL, 20 mmol) was heated to 40 EC for 1 h. The reaction mixture was cooled to room temperature and the precipitate was collected. The filter cake was washed with ethyl acetate (30 mL) to afford the crude dihydrochloride salt (400 mg). The crude solid was suspended in tetrahydrofuran (10 mL). To the mixture was added triethylamine (336 µL, 2.42 mmol) and the slurry was stirred at room temperature for 2 h. The mixture was filtered and evaporated. The residue was suspended in diethyl ether (10 mL) and the mixture was stirred at room temperature for 30 min. The precipitate was collected and dried to give the title compound (210 mg, 53% yield) as a yellow solid. LCMS: Rt=1.101 min, ESMS m/z=297.2 [M+H]⁺.

The following compounds were prepared by the same general method:

| Ex. | Structure | MW | LC-MS (m/z) |
|---|---|---|---|
| P5-2 | 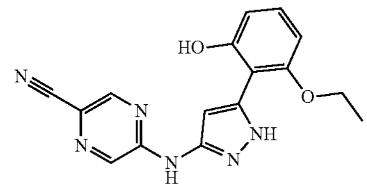 [SMILES: CCOc1cccc(O)c1-c1cc(Nc2cnc(C#N)cn2)n[nH]1] | 322.1 | 323.2 |
| P5-3 | 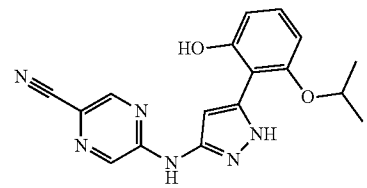 [SMILES: CC(C)Oc1cccc(O)c1-c1cc(Nc2cnc(C#N)cn2)n[nH]1] | 336.1 | 337.2 |
| P5-4 | 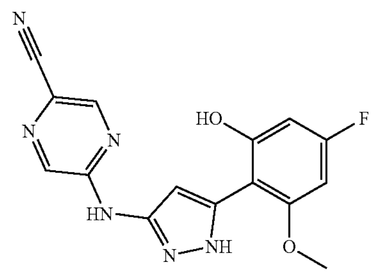 [SMILES: COc1cc(F)cc(O)c1-c1cc(Nc2cnc(C#N)cn2)n[nH]1] | 326.1 | 326.8 |
| P5-5 | 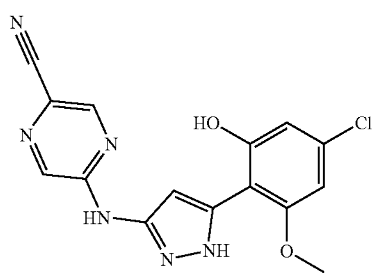 [SMILES: COc1cc(Cl)cc(O)c1-c1cc(Nc2cnc(C#N)cn2)n[nH]1] | 342.1 | 343.0 |
| P5-6 | 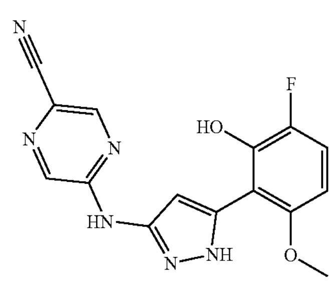 [SMILES: COc1ccc(F)c(O)c1-c1cc(Nc2cnc(C#N)cn2)n[nH]1] | 326.1 | 327.0 |

| Ex. | Structure | MW | LC-MS (m/z) |
|---|---|---|---|
| P5-7 | 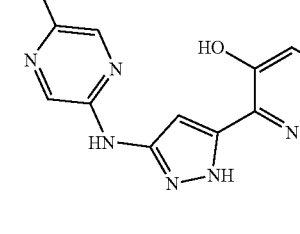 | 348.1 | 349.0 |
| P5-8 | | 348.1 | 349.1 |
| P5-9 | | 326.1 | 327.1 |
| P5-10 | | 376.1 | 377.1 |
| P5-11 | | 322.1 | 323.0 |
| Ex. | Structure | MW | LC-MS (m/z) |
|---|---|---|---|
| P5-12 | 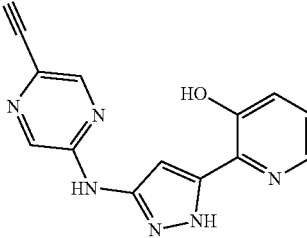 | 279.1 | 280.0 |
| P5-13 | | 293.1 | 294.0 |
Preparation P6-1: tert-Butyl ((1S,3R)-3-((2-acetyl-6-cyclopropylpyridin-3-yl)oxy)cyclopentyl)carbamate
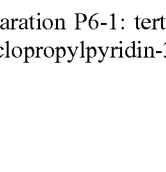

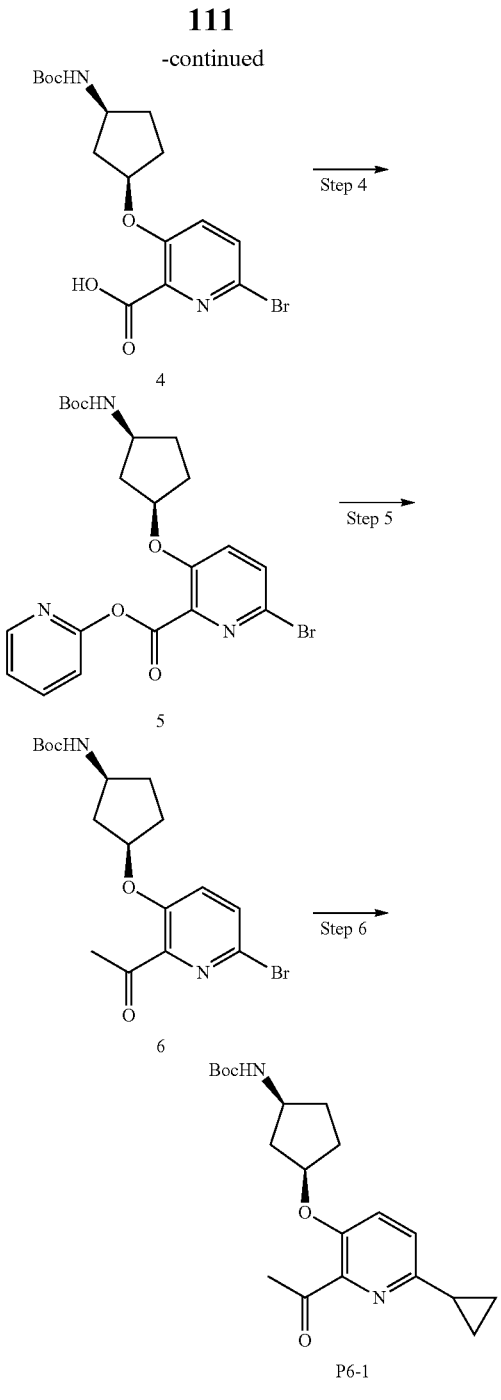

Step 1: Methyl 6-bromo-3-hydroxypicolinate (2)

To a solution of methyl 3-hydroxypyridine-2-carboxylate (3 g, 19.6 mmol) in water (30 mL) was added bromine (1.20 mL, 23.5 mmol) dropwise at −15° C. under nitrogen. The reaction mixture was stirred at room temperature for 4 h. The reaction was quenched with saturated aqueous sodium thiosulfate (20 mL) and the mixture was extracted with dichloromethane (3×50 mL). The combined organic layers were washed with brine (50 mL), dried over sodium sulfate, filtered, and evaporated. The residue was purified by gradient silica gel column chromatography to afford the title compound (2.6 g, 59% yield) as a yellow solid. LCMS: Rt=1.165 min, ESMS m/z=232.0 [M+H]$^+$.

Step 2: Methyl 6-bromo-3-(((1R,3S)-3-((tert-butoxycarbonyl)amino)cyclopentyl)oxy)picolinate (3)

To a solution of methyl 6-bromo-3-hydroxypicolinate (1.5 g, 6.5 mmol), tert-butyl ((1S,3S)-3-hydroxycyclopentyl)carbamate (1.57 g, 7.8 mmol) and triphenylphosphine (3.41 g, 13 mmol) in anhydrous dichloromethane (15 mL) was added diisopropyl azodicarboxylate (2.56 mL, 13 mmol) at 0° C. under nitrogen. The reaction mixture was stirred room temperature for 6 h. The reaction mixture was poured into water (30 mL) and extracted with ethyl acetate (3×20 mL). The combined organic layers were washed with brine (30 mL), dried over sodium sulfate, filtered, and evaporated. The residue was purified by gradient silica gel column chromatography to afford the title compound (2.6 g, 52% yield) as a yellow solid. LCMS: Rt=1.344 min, ESMS m/z=436.9 [M+Na]$^+$.

Step 3: 6-Bromo-3-(((1R,3S)-3-((tert-butoxycarbonyl)amino)cyclopentyl)oxy)picolinic acid (4)

To a solution of methyl 6-bromo-3-{[(1S,3S)-3-{[(tert-butoxy)carbonyl]amino}cyclopentyl]oxy}pyridine-2-carboxylate (2.6 g, 6.3 mmol) in methanol (15 mL) was added aqueous sodium hydroxide (5.4 M, 2.3 mL, 12.6 mmol) dropwise at 0° C. under nitrogen. The reaction mixture was stirred at room temperature for 18 h. The reaction mixture was evaporated. The residue was diluted with water (20 mL) and the mixture was neutralized (pH 7) by addition of 1N hydrochloric acid. The mixture was extracted with ethyl acetate (3×20 mL) and the combined organic layers were dried over sodium sulfate, filtered, and evaporated. The residue was purified by gradient silica gel column chromatography to furnish the title compound (1.9 g, 68% yield) as a colorless oil. LCMS: Rt=1.229 min, ESMS m/z=423.1 [M+Na]$^+$.

Step 4: Pyridin-2-yl 6-bromo-3-(((1R,3S)-3-((tert-butoxycarbonyl)amino)cyclopentyl)oxy)picolinate (5)

A mixture of 6-bromo-3-(((1R,3S)-3-((tert-butoxycarbonyl)amino)cyclopentyl)oxy)picolinic acid (1.9 g, 4.7 mmol), picolinic anhydride (1.53 g, 7.1 mmol) and 4-(dimethylamino)pyridine (57 mg, 0.47 mmol) in dichloromethane (20 mL) was stirred for 2 h under nitrogen. The mixture was extracted with dichloromethane (3×20 mL). The combined organic layers were dried over sodium sulfate, filtered, and evaporated. The residue was purified by gradient silica gel column chromatography to afford the title compound (1.6 g, 71% yield) as a colorless oil. LCMS: Rt=1.335 min, ESMS m/z=478.1 [M+H]$^+$.

Step 5: tert-Butyl ((1S,3R)-3-((2-acetyl-6-bromopyridin-3-yl)oxy)cyclopentyl)(methyl)carbamate (6)

To a solution of pyridin-2-yl 6-bromo-3-(((1R,3S)-3-((tert-butoxycarbonyl)amino)cyclopentyl)oxy)picolinate (1.6 g, 3.3 mmol) in tetrahydrofuran (15 mL) was added a solution of methylmagnesium bromide (3 M in diethyl ether, 1.2 mL, 3.6 mmol) dropwise at 0° C. under nitrogen. The reaction mixture was stirred at 0° C. for 1 h. The reaction was quenched with saturated aqueous ammonium chloride (30 mL) and the mixture was extracted with ethyl acetate (3×20 mL). The combined organic layers were dried over sodium sulfate, filtered, and evaporated. The crude product was purified by gradient silica gel column chromatography to afford the title compound (170 mg, 14% yield) as a yellow oil. LCMS: Rt=1.374 min, ESMS m/z=421.1 [M+Na]⁺.

Step 6: tert-Butyl ((1S,3R)-3-((2-acetyl-6-cyclopropylpyridin-3-yl)oxy)cyclopentyl)carbamate (P6-1)

A mixture of tert-butyl ((1S,3R)-3-((2-acetyl-6-bromopyridin-3-yl)oxy)cyclopentyl)carbamate (170 mg, 0.425 mmol), cyclopropylboronic acid (73 mg, 0.85 mmol), tetrakis(triphenylphosphine)palladium(0) (98 mg, 0.085 mmol) and cesium carbonate (277 mg, 0.85 mmol) in a mixture of 1,4-dioxane and water (5:1, 6 mL) was stirred at 90° C. for 18 h under nitrogen. The reaction mixture was evaporated and the residue was purified by gradient silica gel column chromatography to afford the title compound (25 mg, 16% yield) as a yellow oil. LCMS: Rt=1.448 min, ESMS m/z=361.1 [M+H]⁺.

Preparation P7-1: tert-Butyl ((1S,3R)-3-(2-acetyl-4-chloro-3-methoxyphenoxy)cyclopentyl)carbamate

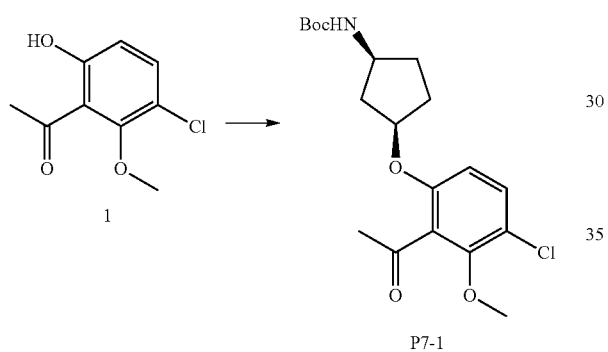

P7-1

To a mixture of 1-(3-chloro-6-hydroxy-2-methoxyphenyl)ethan-1-one (2.0 g, 9.97 mmol), tert-butyl ((1S,3S)-3-hydroxycyclopentyl)carbamate (2.4 g, 11.96 mmol) and triphenylphosphine (5.2 g, 19.93 mmol) in anhydrous tetrahydrofuran (20 mL) was added diisopropyl azodicarboxylate (3.89 mL, 19.93 mmol) at 0'° C. The reaction mixture was stirred at room temperature for 2 h. The reaction was quenched with water (50 mL) and the mixture was extracted with ethyl acetate (3×30 mL). The combined organic layers were dried over anhydrous sodium sulfate, filtered and evaporated. The crude product was purified by gradient silica gel column chromatography to afford the title compound (2.6 g, 68% yield) as a yellow oil. LCMS: Rt=1.415 min, ESMS m/z=406.1 [M+Na]⁺.

The following compound was prepared by the same general method:

| Ex. | Structure | MW | LC-MS (m/z) |
|---|---|---|---|
| P7-2 | BocHN... | 383.1 | 406.1 |

Preparation P8-1: tert-Butyl ((1S,3R)-3-(2-acetyl-3-methoxy-4-methylphenoxy)cyclopentyl)carbamate

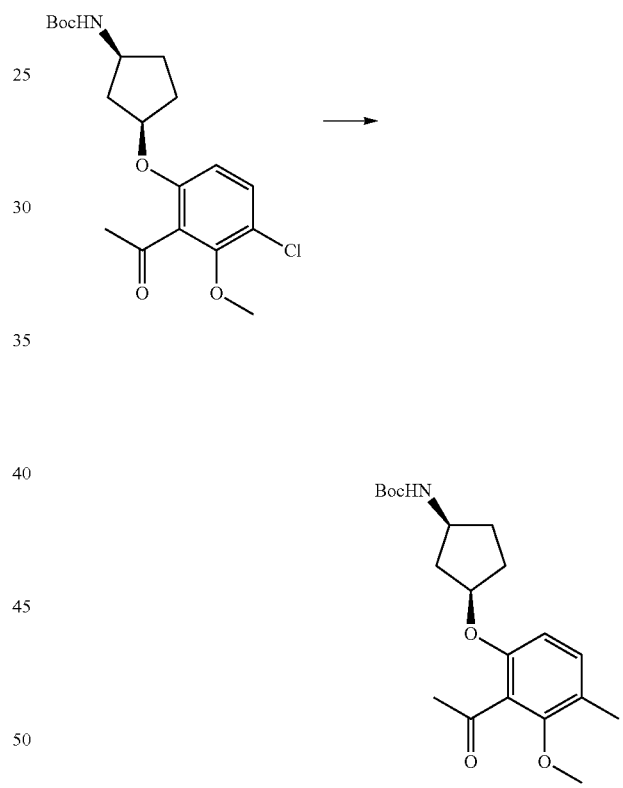

A mixture of tert-butyl ((1S,3R)-3-(2-acetyl-4-chloro-3-methoxyphenoxy)cyclopentyl)carbamate (1.0 g, 2.6 mmol), trimethylboroxine (490 mg, 3.9 mmol), [1,3-bis(2,6-diisopropylphenyl)imidazol-2-ylidene](3-chloropyridyl)palladium(II) dichloride (PEPPSI-IPr, 180 mg, 0.26 mmol) and potassium carbonate (1.08 g, 7.8 mmol) in 1,4-dioxane (10 mL) was heated to 100° C. for 18 h under nitrogen. The mixture was evaporated and the residue was purified by gradient silica gel column chromatography to give the title compound (800 mg, 85% yield) as a white solid. LCMS: Rt=1.403 min, ESMS m/z=386.0 [M+Na]⁺.

The following compound was prepared by the same general method:

| Ex. | Structure | MW | LC-MS (m/z) |
|---|---|---|---|
| P8-2 | BocHN, cyclopentyl-O-aryl structure | 363.2 | 386.0 |

Preparation P9-1: 1-(2-Fluoro-6-hydroxy-4-methylphenyl)ethan-1-one

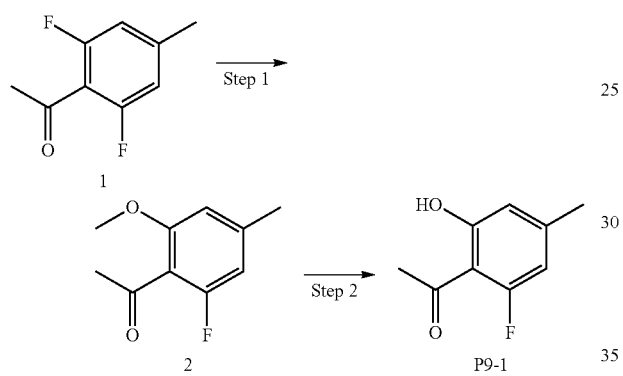

Step 1: 1-(2-Fluoro-6-methoxy-4-methylphenyl)ethan-1-one (2)

To a solution of 1-(2,6-difluoro-4-methylphenyl)ethan-1-one (690 mg, 4.05 mmol) in methanol (10 mL) was added sodium methoxide (5.4 M in methanol, 1.12 mL, 6.07 mmol) at room temperature. The reaction mixture was heated to 70° C. for 2 h. The reaction mixture was evaporated. The crude product was taken up in water (30 mL) and the mixture was extracted with dichloromethane (3×50 mL). The combined organic layers were dried over sodium sulfate, filtered, and evaporated. The crude product was purified by gradient silica gel column chromatography to give the title compound (410 mg, 50% yield) as a white solid. LCMS: Rt=1.246 min, ESMS m/z=183.1 [M+1]$^+$.

Step 2: 1-(2-Fluoro-6-hydroxy-4-methylphenyl)ethan-1-one

To a mixture of 1-(2-fluoro-6-methoxy-4-methylphenyl)ethan-1-one (410 mg, 1.7 mmol) in dichloromethane (10 mL) was added aluminum trichloride (453 mg, 3.4 mmol) at 0° C. and the reaction mixture was stirred at room temperature for 2 h under nitrogen. The reaction was quenched with water (50 mL) and the mixture was extracted with dichloromethane (3×20 mL). The combined organic layers were dried over sodium sulfate, filtered, and evaporated. The crude product was purified by gradient silica gel column chromatography to afford the title compound (220 mg, 69% yield) as a colorless oil. LCMS: Rt=1.336 min, ESMS no mass.

Preparation P10-1: 3-Fluoro-2-(isoxazol-5-yl)-5-methylphenol

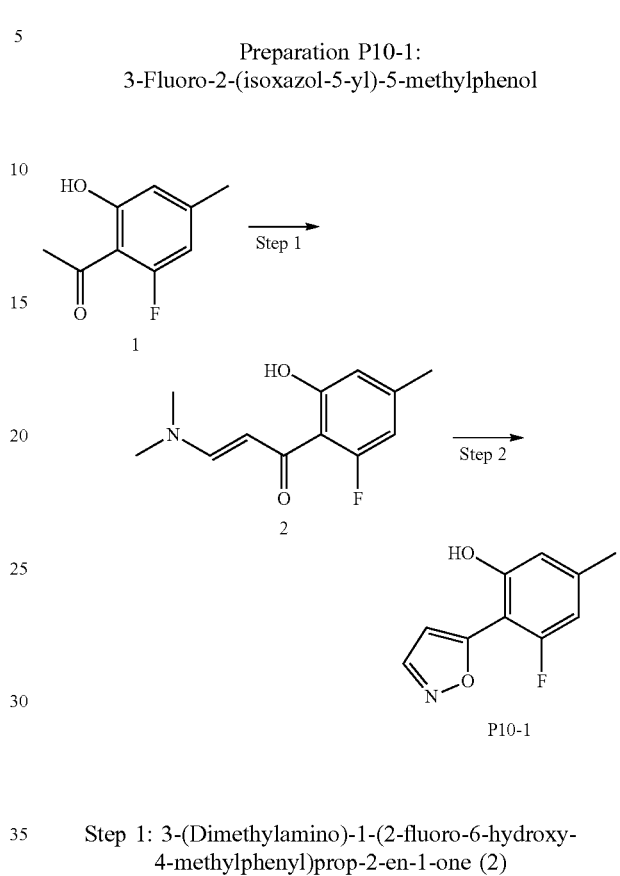

Step 1: 3-(Dimethylamino)-1-(2-fluoro-6-hydroxy-4-methylphenyl)prop-2-en-1-one (2)

A mixture of 1-(2-fluoro-6-hydroxy-4-methylphenyl)ethan-1-one (220 mg, 1.31 mmol) and N,N-dimethylformamide dimethylacetal (522 μL, 3.9 mmol) in anhydrous N,N-dimethylformamide (5 mL) was heated to 80° C. for 18 h. The reaction mixture was evaporated to afford the crude title compound (240 mg) as a yellow oil, which was used without purification. LCMS: Rt=1.266 min, ESMS m/z=224.2 [M+H]$^+$.

Step 2: 3-Fluoro-2-(isoxazol-5-yl)-5-methylphenol (P10-1)

A mixture of crude 3-(dimethylamino)-1-(2-fluoro-6-hydroxy-4-methylphenyl)prop-2-en-1-one (240 mg) and hydroxylamine hydrochloride (112 mg, 1.61 mmol) in anhydrous ethanol (5 mL) was stirred at 50° C. for 1 h under nitrogen. The reaction mixture was evaporated and the residue was taken up in water (30 mL). The mixture was extracted with ethyl acetate (3×20 mL) and the combined organic layers were dried over sodium sulfate, filtered, and evaporated. The crude product was purified by gradient silica gel column chromatography to give the title compound (180 mg, 71% yield over 2 steps) as a yellow solid. LCMS: Rt=1.168 min, ESMS m/z=194.1 [M+H]$^+$.

The following compound was prepared by the same general method:

| Ex. | Structure | MW | LC-MS (m/z) |
|---|---|---|---|
| P10-2 | 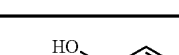 | 179.1 | 180.1 |

Preparation P11-1: (1s,3s)-3-((tert-Butoxycarbonyl)(methyl)amino)cyclobutyl methanesulfonate

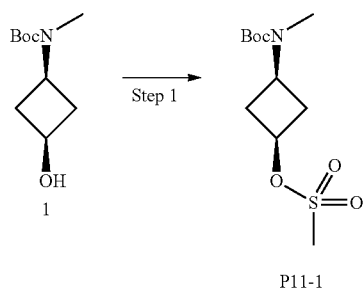

P11-1

To a solution of tert-butyl ((1s,3s)-3-hydroxycyclobutyl)(methyl)carbamate (300 mg, 1.48 mmol) and triethylamine (620 μL, 4.45 mmol) in dichloromethane (10 mL) was added methanesulfonyl chloride (190 μL, 2.22 mmol) and the reaction mixture was stirred at room temperature for 18 h under nitrogen. The reaction mixture was evaporated to afford the crude title compound (450 mg) as white solid, which was used without purification. LCMS: Rt=1.222 min, ESMS m/z=302.1 [M+Na]⁺.

The following compounds were prepared by the same general method:

| Ex. | Structure | MW | LC-MS (m/z) |
|---|---|---|---|
| P11-2 | 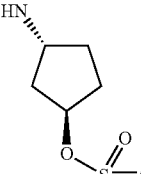 | 279.1 | 302.2 |
| P11-3 | 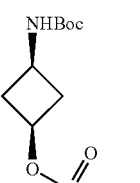 | 265.1 | 288.0 |
| P11-4 | 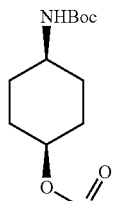 | 293.1 | 316.0 |

Preparation P12-1: tert-Butyl 3-((tert-butoxycarbonyl)(5-cyanopyrazin-2-yl)amino)-5-(4,4,5,5-tetramethyl-1,3,2-dioxaborolan-2-yl)-1H-pyrazole-1-carboxylate

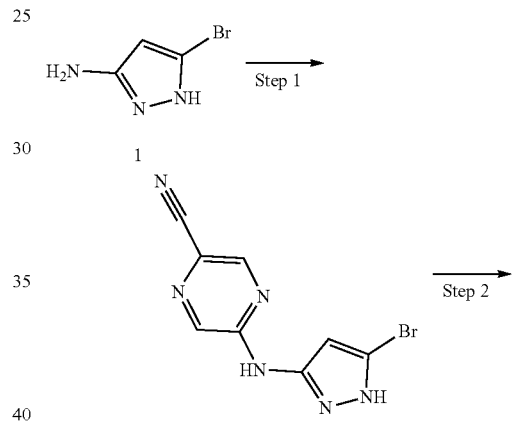

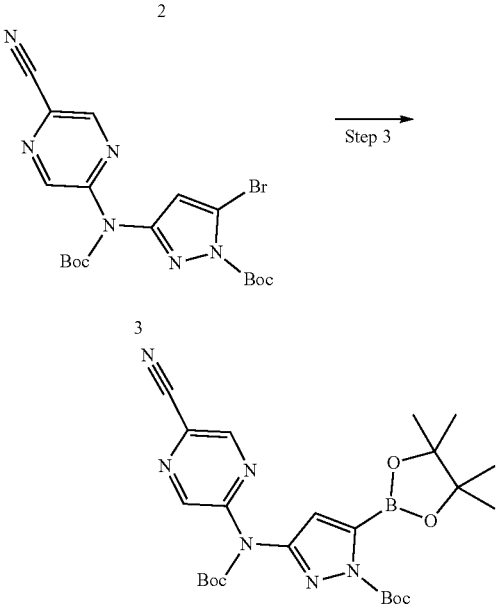

P12-1

Step 1: 5-((5-bromo-1H-pyrazol-3-yl)amino)pyrazine-2-carbonitrile (2)

A mixture of 5-chloropyrazine-2-carbonitrile (10 g, 71.7 mmol), 5-bromo-1H-pyrazol-3-amine (12.19 g, 75.25 mmol) and cesium carbonate (70.0 g, 215 mmol) in dimethyl sulfoxide (250 mL) was stirred at 80° C. for 18 h. The reaction mixture was poured into ice water (1 L) and the mixture was stirred for 30 min. The precipitate was collected and the filter cake was washed with water (1 L) and dried to give the title compound (18 g, 95% yield) as light-brown solid. LCMS: Rt=1.080 min, ESMS m/z=264.9 [M+H]$^+$.

Step 2: tert-Butyl 5-bromo-3-((tert-butoxycarbonyl)(5-cyanopyrazin-2-yl)amino)-1H-pyrazole-1-carboxylate (3)

A mixture of 5-((5-bromo-1H-pyrazol-3-yl)amino)pyrazine-2-carbonitrile (18 g, 67.9 mmol) and di-tert-butyldicarbonate (76 g, 348 mmol) was heated to 80° C. for 18 h. The mixture was evaporated under vacuum and the crude product was purified by gradient silica gel column chromatography to give the title compound (28 g, 89% yield) as a white solid. LCMS: Rt=1.440 min, ESMS m/z=486.9 [M+Na]$^+$.

Step 3: tert-Butyl 3-((tert-butoxycarbonyl)(5-cyanopyrazin-2-yl)amino)-5-(4,4,5,5-tetramethyl-1,3,2-dioxaborolan-2-yl)-1H-pyrazole-1-carboxylate (P12-1)

A mixture of tert-butyl 5-bromo-3-((tert-butoxycarbonyl)(5-cyanopyrazin-2-yl)amino)-1H-pyrazole-1-carboxylate (3.0 g, 6.46 mmol), bis(pinacolato)diboron (2.3 g, 9.06 mmol), [1,1'-bis(diphenylphosphino)ferrocene]dichloropalladium(II) (948 mg, 1.30 mmol) and potassium acetate (1.27 g, 12.94 mmol) in 1,4-dioxane (100 mL) was stirred at 90° C. for 2.5 h under nitrogen. The mixture was cooled to room temperature and diluted with dichloromethane (100 mL). The mixture was filtered and the solid was washed with dichloromethane (2×100 mL). The filtrate was evaporated and the residue was taken up in dichloromethane (20 mL). The crude product was purified by gradient silica gel column chromatography to afford the title compound (2.2 g, 66% yield) as a yellow oil. LCMS: Rt=1.261 min, ESMS m/z=331.1 [M+H-Boc-pinacol]$^+$.

Preparation P13-1: 2-Bromo-5-fluoro-6-methylpyridin-3-ol

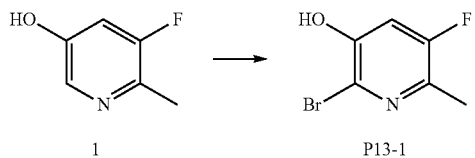

To a solution of 5-fluoro-6-methylpyridin-3-ol (100 mg, 0.79 mmol) in pyridine (3 mL) was added bromine (44 µL, 0.87 mmol) dropwise at 0° C. under nitrogen. The reaction mixture was stirred at 30° C. for 18 h. The reaction mixture was poured into water (10 mL) and extracted with ethyl acetate (3×20 mL). The combined organic layers were washed with brine, dried over sodium sulfate, filtered, and evaporated. The residue was purified by gradient silica gel column chromatography to give the title compound (200 mg, 97% yield) as a light orange oil. LCMS: Rt=1.087 min, ESMS m/z=206.0 [M+H]$^+$.

Preparation P14-1: tert-Butyl ((1S,3R)-3-(3-fluoro-2-iodo-4-methylphenoxy)cyclopentyl)carbamate

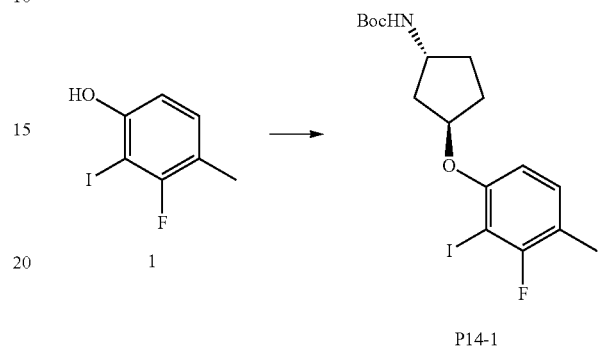

To a mixture of 3-fluoro-2-iodo-4-methylphenol (300 mg, 1.19 mmol), tert-butyl ((1S,3S)-3-hydroxycyclopentyl) carbamate (288 mg, 1.43 mmol) and triphenylphosphine (624 mg, 2.38 mmol) in anhydrous tetrahydrofuran (5 mL) was added diisopropyl azodicarboxylate (469 µL, 2.38 mmol) at 0° C. under nitrogen. The reaction mixture was stirred at room temperature for 18 h. The reaction mixture was poured into water (10 mL) and extracted with ethyl acetate (3×10 mL). The combined organic layers were washed with brine (10 mL), dried over sodium sulfate, filtered, and evaporated. The residue was purified by gradient silica gel column chromatography to afford the title compound (350 mg, 61% yield) as a yellow solid. LCMS: Rt=1.530 min, ESMS m/z=458.0 [M+Na]$^+$.

The following compounds were prepared by the same general method:

| Ex. | Structure | MW | LC-MS (m/z) |
|---|---|---|---|
| P14-2 | NHBoc | 411.1 | 434.0 |

-continued

| Ex. | Structure | MW | LC-MS (m/z) |
|---|---|---|---|
| P14-3 | 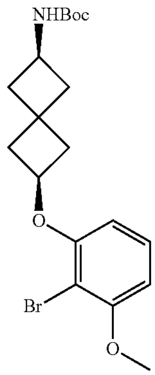 [SMILES: COc1cccc(O[C@H]2CC3(C[C@H](NC(=O)OC(C)(C)C)C3)C2)c1Br] | 411.1 | 434.0 |
| P14-4 | 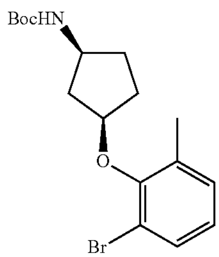 [SMILES: Cc1cccc(Br)c1O[C@@H]1CC[C@H](NC(=O)OC(C)(C)C)C1] | 369.1 | 392.0 |
| P14-5 | 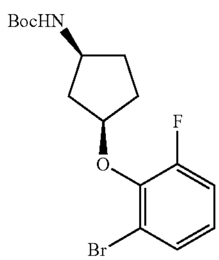 [SMILES: CC(C)(C)OC(=O)N[C@H]1CC[C@@H](Oc2c(F)cccc2Br)C1] | 373.1 | 395.9 |
| P14-6 | 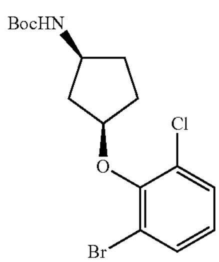 [SMILES: CC(C)(C)OC(=O)N[C@H]1CC[C@@H](Oc2c(Cl)cccc2Br)C1] | 389.0 | 412.0 |
| P14-7 | 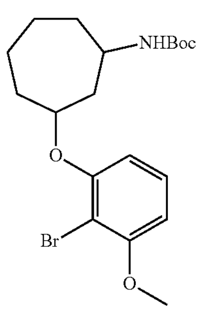 [SMILES: COc1cccc(OC2CCCCC(NC(=O)OC(C)(C)C)C2)c1Br] | 413.1 | 436.0 |

-continued

| Ex. | Structure | MW | LC-MS (m/z) |
|---|---|---|---|
| P14-8 | 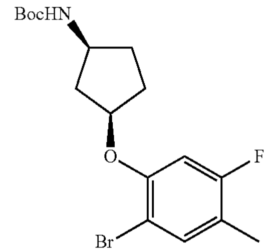 [SMILES: Cc1cc(Br)c(O[C@@H]2CC[C@H](NC(=O)OC(C)(C)C)C2)cc1F] | 387.1 | 410.1 |
| P14-9 | 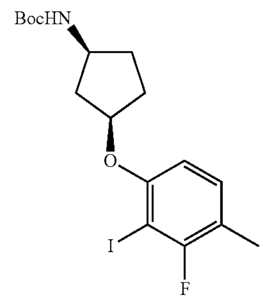 [SMILES: Cc1ccc(O[C@@H]2CC[C@H](NC(=O)OC(C)(C)C)C2)c(I)c1F] | 435.1 | 436.1 |
| P14-10 | 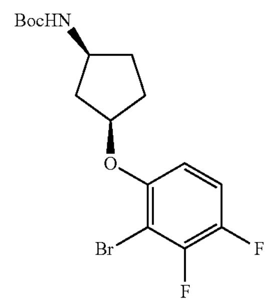 [SMILES: CC(C)(C)OC(=O)N[C@H]1CC[C@@H](Oc2ccc(F)c(F)c2Br)C1] | 391.1 | 413.9 |
| P14-11 | 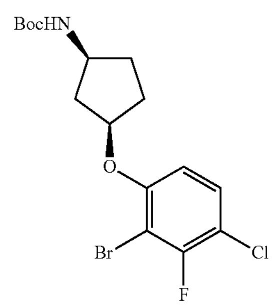 [SMILES: CC(C)(C)OC(=O)N[C@H]1CC[C@@H](Oc2ccc(Cl)c(F)c2Br)C1] | 407.0 | 429.9 |
| P14-12 | 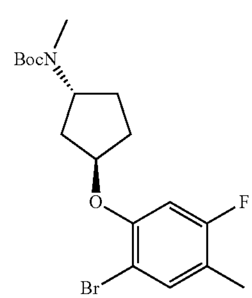 [SMILES: Cc1cc(Br)c(O[C@@H]2CC[C@@H](N(C)C(=O)OC(C)(C)C)C2)cc1F] | 401.1 | 424.1 |

-continued

| Ex. | Structure | MW | LC-MS (m/z) |
|---|---|---|---|
| P14-13 | 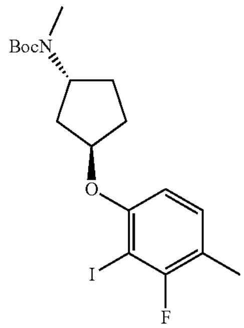 [SMILES: Cc1ccc(O[C@@H]2CC[C@@H](N(C)C(=O)OC(C)(C)C)C2)c(I)c1F] | 449.1 | 450.1 |
| P14-14 | 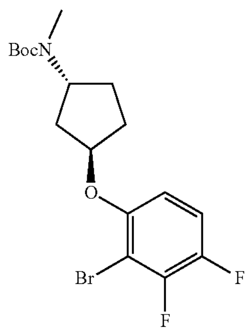 [SMILES: CN(C(=O)OC(C)(C)C)[C@@H]1CC[C@@H](Oc2ccc(F)c(F)c2Br)C1] | 405.1 | 427.9 |
| P14-15 | 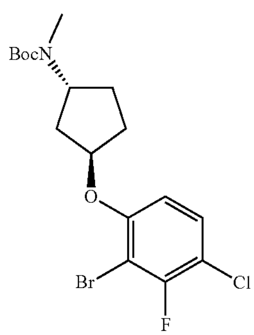 [SMILES: CN(C(=O)OC(C)(C)C)[C@@H]1CC[C@@H](Oc2ccc(Cl)c(F)c2Br)C1] | 421.1 | 444.0 |
| P14-16 | 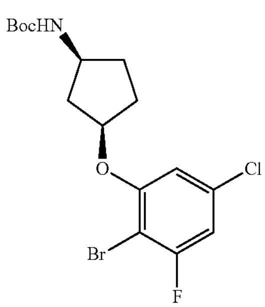 [SMILES: CC(C)(C)OC(=O)N[C@H]1CC[C@@H](Oc2cc(Cl)cc(F)c2Br)C1] | 407.0 | 429.9 |

-continued

| Ex. | Structure | MW | LC-MS (m/z) |
|---|---|---|---|
| P14-17 | 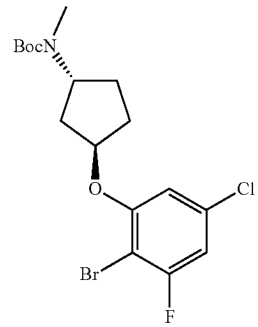 [SMILES: CN(C(=O)OC(C)(C)C)[C@@H]1CC[C@@H](Oc2cc(Cl)cc(F)c2Br)C1] | 421.0 | 444.0 |
| P14-18 | 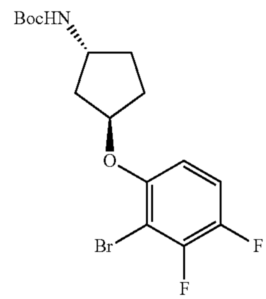 [SMILES: CC(C)(C)OC(=O)N[C@@H]1CC[C@@H](Oc2ccc(F)c(F)c2Br)C1] | 391.1 | 413.9 |
| P14-19 | 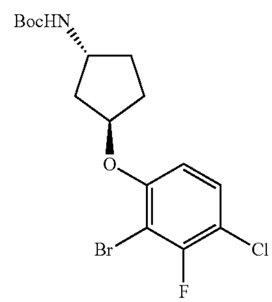 [SMILES: CC(C)(C)OC(=O)N[C@@H]1CC[C@@H](Oc2ccc(Cl)c(F)c2Br)C1] | 407.0 | 430.1 |
| P14-20 | 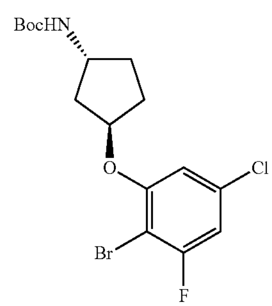 [SMILES: CC(C)(C)OC(=O)N[C@@H]1CC[C@@H](Oc2cc(Cl)cc(F)c2Br)C1] | 407.0 | 408.2 |
| P14-21 | 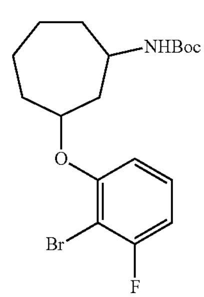 [SMILES: CC(C)(C)OC(=O)NC1CCCCC(Oc2cccc(F)c2Br)C1] | 401.1 | 424.1 |

-continued

| Ex. | Structure | MW | LC-MS (m/z) |
|---|---|---|---|
| P14-22 | (2-bromo-3-fluorophenoxy)cyclopentyl-NHBoc | 373.1 | 396.1 |
| P14-23 | (2-bromo-3-fluorophenoxy)cyclopentyl-NHBoc (diastereomer) | 373.1 | 395.9 |
| P14-24 | spiro[3.3]heptyl-(2-bromo-3-fluorophenoxy)-NHBoc | 399.1 | 422.1 |
| P14-25 | BocHN-cyclopentyl-O-(2-bromopyridin-3-yl) | 356.1 | 379.0 |
| P14-26 | BocHN-cyclopentyl-O-(2-bromo-6-methylpyridin-3-yl) | 370.1 | 371.0 |

-continued

| Ex. | Structure | MW | LC-MS (m/z) |
|---|---|---|---|
| P14-27 | BocN(Me)-cyclopentyl-O-(2-bromo-6-methylpyridin-3-yl) | 384.1 | 385.0 |
| P14-28 | BocHN-cyclopentyl-O-(2-bromo-5,6-dimethylpyridin-3-yl) | 384.1 | 385.0 |
| P14-29 | BocHN-cyclopentyl-O-(2-bromo-6-trifluoromethylpyridin-3-yl) | 424.1 | 447.1 |
| P14-30 | BocHN-cyclopentyl-O-(2-bromo-5-fluoro-6-methylpyridin-3-yl) | 388.1 | 411.0 |
| P14-31 | BocHN-cyclopentyl-O-(2-bromo-5-chloro-6-methylpyridin-3-yl) | 404.0 | 405.1 |

| Ex. | Structure | MW | LC-MS (m/z) |
|---|---|---|---|
| P14-32 | 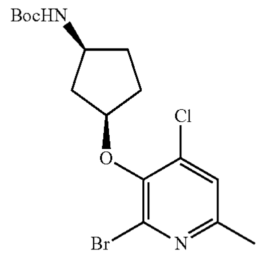 [SMILES: Cc1cc(Cl)c(O[C@@H]2CC[C@H](NC(=O)OC(C)(C)C)C2)c(Br)n1] | 404.0 | 405.1 |

Preparation P15-1: N-((1S,2S)-2-(2-Bromo-3-fluorophenoxy)cyclobutyl)-2-methylpropane-2-sulfinamide and Preparation P15-2: N-((1S,2R)-2-(2-bromo-3-fluorophenoxy)cyclobutyl)-2-methylpropane-2-sulfinamide

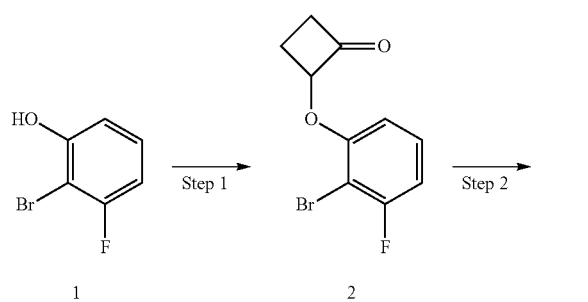

Step 1:
2-(2-Bromo-3-fluorophenoxy)cyclobutan-1-one (2)

A mixture of 2-bromo-3-fluorophenol (3 g, 16 mmol), 2-bromocyclobutan-1-one (7.07 g, 80 mmol) and potassium carbonate (5.45 g, 40 mmol) in N,N-dimethylformamide (30 mL) was stirred at 50° C. for 12 h. The reaction mixture was filtered and evaporated. The residue was purified by gradient silica gel column chromatography to give the title compound (1.65 g, 42% yield) as a white solid. LCMS: Rt=1.303 min, ESMS m/z=258.9 [M+H]$^+$.

Step 2: N-((1S,2S)-2-(2-Bromo-3-fluorophenoxy)cyclobutyl)-2-methylpropane-2-sulfinamide and N-((1S,2R)-2-(2-bromo-3-fluorophenoxy)cyclobutyl)-2-methylpropane-2-sulfinamide (P15-1 and P15-2)

A solution of 2-(2-bromo-3-fluorophenoxy)cyclobutan-1-one (200 mg, 0.772 mmol), (S)-2-methylpropane-2-sulfinamide (103 mg, 0.849 mmol) and titanium(IV) ethoxide (302 μL, 1.16 mmol) in tetrahydrofuran (6 mL) was stirred at room temperature for 3 h under nitrogen. To the reaction mixture was added sodium borohydride (58 mg, 1.54 mmol) at 0° C. The reaction mixture was heated to 40° C. for 2 h. The reaction was quenched by addition of methanol (5 mL) and water (50 mL). The mixture was extracted with ethyl acetate (3×50 mL). The combined organic layers were dried over sodium sulfate, filtered, and evaporated. The residue was purified by preparative HPLC to afford N-((1S,2S)-2-(2-bromo-3-fluorophenoxy)cyclobutyl)-2-methylpropane-2-sulfinamide (30 mg, 12% yield) as a white solid and N-((1S,2R)-2-(2-bromo-3-fluorophenoxy)cyclobutyl)-2-methylpropane-2-sulfinamide (30 mg, 12% yield) as a white solid.

The isomers were assigned arbitrarily.

Isomer 1 LCMS: Rt=1.332 min, ESMS m/z=364.0 [M+H]$^+$.

Isomer 2 LCMS: Rt=1.366 min, ESMS m/z=364.0 [M+H]$^+$.

The following compounds were prepared by the same general method:

| Ex. | Structure | MW | LC-MS (m/z) |
|---|---|---|---|
| P15-3 | 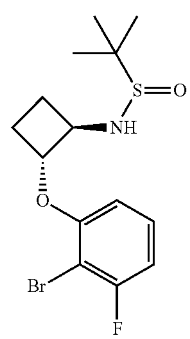 [SMILES: CC(C)(C)S(=O)N[C@@H]1CC[C@H]1Oc1cccc(F)c1Br] | 363.0 | 364.0 |
| P15-4 | 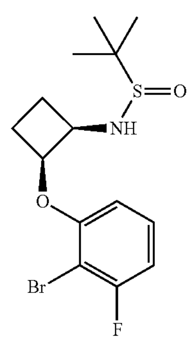 [SMILES: CC(C)(C)S(=O)N[C@@H]1CC[C@@H]1Oc1cccc(F)c1Br] | 363.0 | 364.0 |

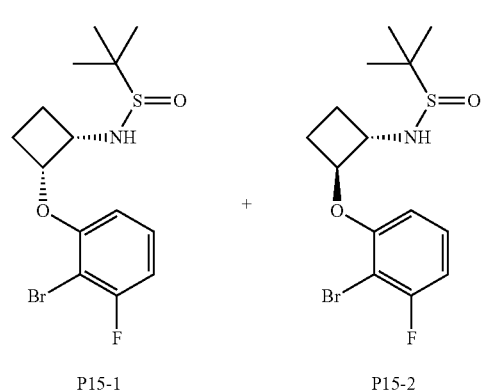

| Ex. | Structure | MW | LC-MS (m/z) |
|---|---|---|---|
| P15-5 | 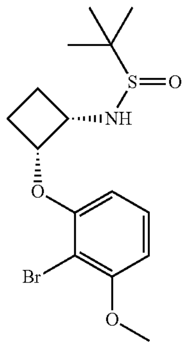 [SMILES: COc1cccc(O[C@@H]2CC[C@@H]2NS(=O)C(C)(C)C)c1Br] | 375.1 | 376.0 |
| P15-6 | 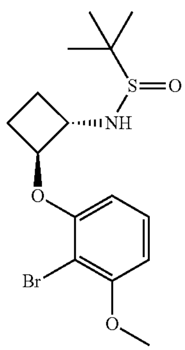 [SMILES: COc1cccc(O[C@H]2CC[C@@H]2NS(=O)C(C)(C)C)c1Br] | 375.1 | 376.0 |
| P15-7 | 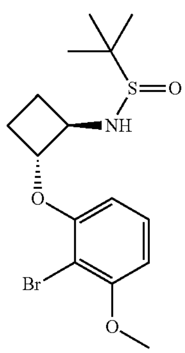 [SMILES: COc1cccc(O[C@@H]2CC[C@H]2NS(=O)C(C)(C)C)c1Br] | 375.1 | 376.0 |
| P15-8 | 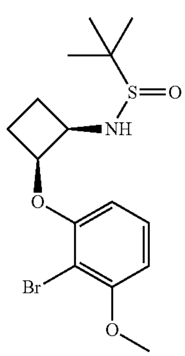 [SMILES: COc1cccc(O[C@H]2CC[C@H]2NS(=O)C(C)(C)C)c1Br] | 375.1 | 376.0 |
Preparation P16-1: tert-Butyl ((1S,3R)-3-((2-bromo-6-isopropylpyridin-3-yl)oxy)cyclopentyl)carbamate and Preparation P16-2: tert-butyl ((1S,3R)-3-((2-bromo-6-propylpyridin-3-yl)oxy)cyclopentyl)carbamate
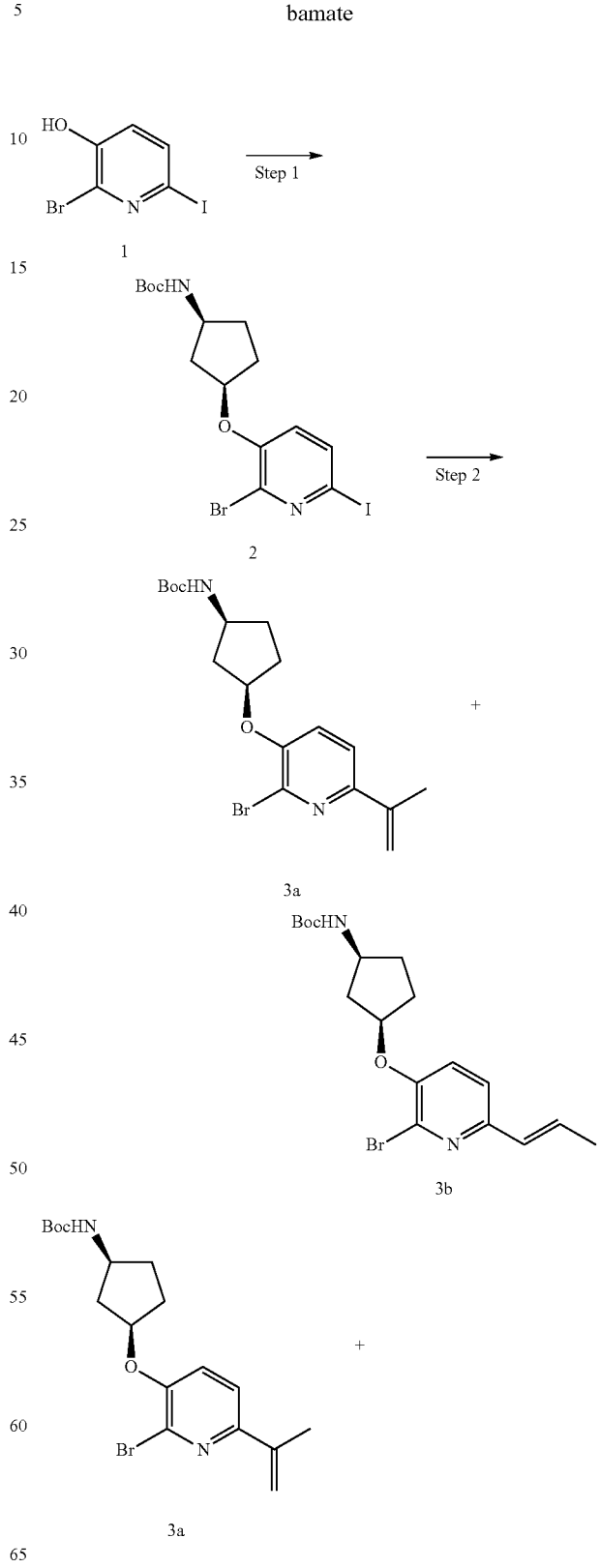

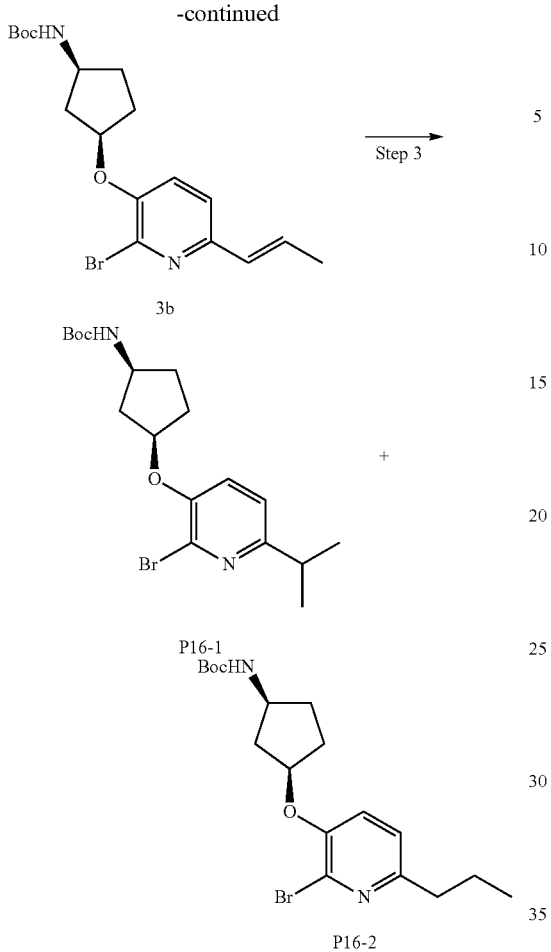

Step 1: tert-Butyl ((1S,3R)-3-((2-bromo-6-iodopyridin-3-yl)oxy)cyclopentyl)carbamate (2)

To a solution of 2-bromo-6-iodopyridin-3-ol (2.0 g, 6.67 mmol), tert-butyl ((1S,3S)-3-hydroxycyclopentyl) carbamate (1.6 g, 8.00 mmol) and triphenylphosphine (2.5 g, 9.34 mmol) in dichloromethane (20 mL) was added diisopropyl azodicarboxylate (1.95 mL, 10.0 mmol) at 0° C. under nitrogen. The reaction mixture was stirred at room temperature for 18 h. The reaction mixture was poured into water (20 mL) and extracted with dichloromethane (3×20 mL). The combined organic layers were washed with brine (20 mL), dried over sodium sulfate, filtered, and evaporated. The crude product was purified by gradient silica gel column chromatography to afford the title compound (2.4 g, 74% yield) as a yellow oil. LCMS: Rt=1.446 min, ESMS m/z=504.8 [M+Na]+.

Step 2: tert-Butyl ((1S,3R)-3-((2-bromo-6-(prop-1-en-2-yl)pyridin-3-yl)oxy)cyclopentyl)carbamate and tert-butyl ((1S,3R)-3-((2-bromo-6-(prop-1-en-1-yl)pyridin-3-yl)oxy)cyclopentyl)carbamate (3a and 3b)

To a solution of tert-butyl ((1S,3R)-3-((2-bromo-6-iodopyridin-3-yl)oxy)cyclopentyl)carbamate (1.0 g, 2.07 mmol), 4,4,5,5-tetramethyl-2-(prop-1-en-2-yl)-1,3,2-dioxaborolane (400 mg, 2.48 mmol) and sodium carbonate (700 mg, 6.21 mmol) in a mixture of 1,4-dioxane and water (5:1, 12 mL) was added tetrakis(triphenylphosphine)palladium(0) (500 mg, 0.41 mmol) and the reaction mixture was stirred at 70° C. for 18 h under nitrogen. The mixture was poured into water (20 mL) and extracted with ethyl acetate (3×20 mL). The combined organic layers were washed with brine (20 mL), dried over sodium sulfate, filtered, and evaporated. The residue was purified by gradient silica gel column chromatography to afford a mixture of the title compounds (400 mg, 49% yield) as a colorless oil, which was used without further purification. LCMS: Rt=1.488 min, ESMS m/z=397.0 [M+H]+.

Step 3: tert-Butyl ((1S,3R)-3-((2-bromo-6-isopropylpyridin-3-yl)oxy)cyclopentyl)carbamate and tert-butyl ((1S,3R)-3-((2-bromo-6-propylpyridin-3-yl)oxy)cyclopentyl)carbamate (P16-1 and P16-2)

To a mixture of tert-butyl ((1S,3R)-3-((2-bromo-6-(prop-1-en-2-yl)pyridin-3-yl)oxy)cyclopentyl)carbamate and tert-butyl ((1S,3R)-3-((2-bromo-6-(prop-1-en-1-yl)pyridin-3-yl)oxy)cyclopentyl)carbamate (200 mg, 0.51 mmol) in methanol (5 mL) was added tris(triphenylphosphine)rhodium(I) chloride (93 mg, 0.10 mmol) and the reaction mixture was stirred at room temperature for 18 h under a hydrogen atmosphere. The mixture was filtered and evaporated. The residue was purified by preparative thin layer chromatography to afford a mixture of the title compounds (120 mg, 60% yield) as a colorless oil, which was used without further purification. LCMS: Rt=1.477 min, ESMS m/z=398.9 [M+H]+.

Preparation P17-1: tert-Butyl ((1S,3R)-3-((2-bromo-6-(difluoromethyl)pyridin-3-yl)oxy)cyclopentyl)carbamate

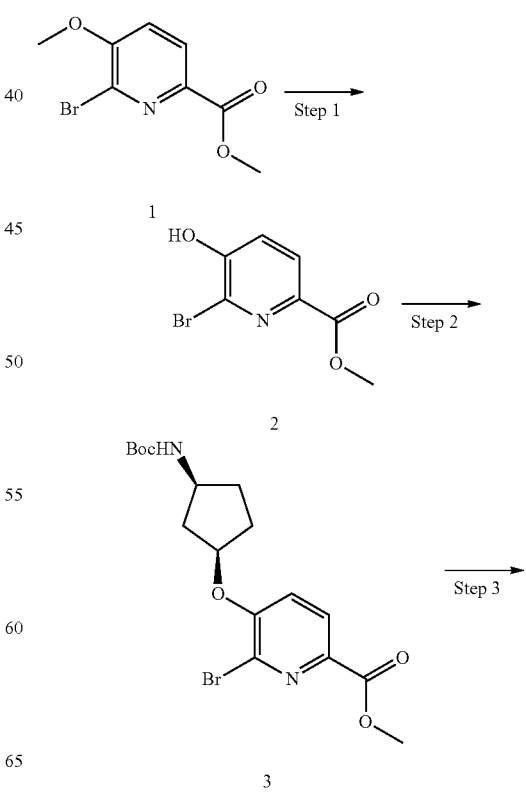

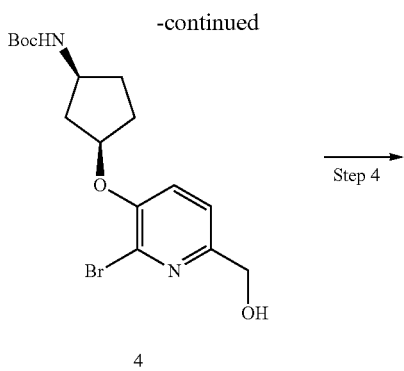

4

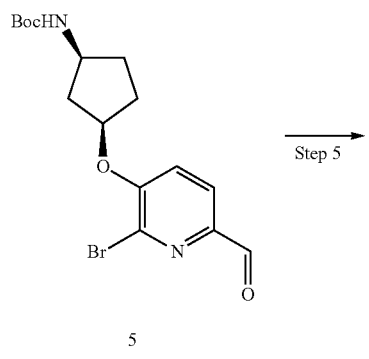

5

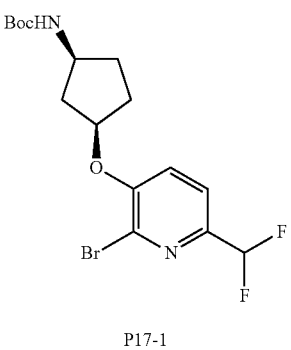

P17-1

Step 1: Methyl 6-bromo-5-hydroxypicolinate (2)

To a solution of methyl 6-bromo-5-methoxypicolinate (600 mg, 2.45 mmol) in anhydrous dichloromethane (10 mL) was added aluminum trichloride (326 mg, 2.45 mmol) at 0° C. The reaction mixture was heated to 40° C. for 50 h under nitrogen. The reaction mixture was poured into water (60 mL) and extracted with dichloromethane (3×40 mL). The combined organic layers were washed with brine (40 mL), dried over sodium sulfate, filtered, and evaporated. The residue was purified by gradient silica gel column chromatography to furnish the title compound (300 mg, 53% yield) as a white solid. LCMS: Rt=1.008 min, ESMS m/z=232.0 [M+H]$^+$.

Step 2: Methyl 6-bromo-5-(((1R,3S)-3-((tert-butoxycarbonyl)amino)cyclopentyl)oxy)picolinate (3)

A solution of methyl 6-bromo-5-hydroxypicolinate (300 mg, 1.30 mmol), tert-butyl ((1S,3S)-3-hydroxycyclopentyl) carbamate (314 mg, 1.56 mmol), triphenylphosphine (511 mg, 1.95 mmol) and diisopropyl azodicarboxylate (384 μL, 1.95 mmol) in anhydrous dichloromethane (20 mL) was stirred at room temperature for 18 h under nitrogen. The reaction mixture was poured into water (60 mL) and extracted with dichloromethane (3×40 mL). The combined organic layers were washed with brine (40 mL), dried over sodium sulfate, filtered, and evaporated. The residue was purified by gradient silica gel column chromatography to afford the title compound (420 mg, 78% yield) as a white solid. LCMS: Rt=1.306 min, ESMS m/z=437.1 [M+Na]$^+$.

Step 3: tert-Butyl ((1S,3R)-3-((2-bromo-6-(hydroxymethyl)pyridin-3-yl)oxy)cyclopentyl)carbamate (4)

A mixture of methyl 6-bromo-5-(((1R,3S)-3-((tert-butoxycarbonyl)amino)cyclopentyl)oxy)picolinate (420 mg, 1.01 mmol), sodium borohydride (39 mg, 1.01 mmol) and calcium chloride (112 mg, 1.01 mmol) in anhydrous ethanol (20 mL) was heated to reflux for 1 h under nitrogen. The reaction mixture was poured into water (60 mL) and the mixture was extracted with dichloromethane (3×40 mL). The combined organic layers were washed with brine (40 mL), dried over sodium sulfate, filtered, and evaporated. The crude product was purified by gradient silica gel column chromatography to give the title compound (310 mg, 79% yield) as a white solid. LCMS: Rt=1.229 min, ESMS m/z=387.1 [M+H]$^+$.

Step 4: tert-Butyl ((1S,3R)-3-((2-bromo-6-formylpyridin-3-yl)oxy)cyclopentyl)carbamate (5)

A solution of tert-butyl ((1S,3R)-3-((2-bromo-6-(hydroxymethyl)pyridin-3-yl)oxy)cyclopentyl)carbamate (310 mg, 0.80 mmol) and Dess-Martin periodinane (339 mg, 0.80 mmol) in anhydrous dichloromethane (10 mL) was stirred at room temperature for 1 h under nitrogen. The reaction mixture was poured into water (60 mL) and extracted with dichloromethane (3×40 mL). The combined organic layers were washed with brine (40 mL), dried over sodium sulfate, filtered, and evaporated. The residue was purified by gradient silica gel column chromatography to afford the title compound (220 mg, 57% yield) as a white solid. LCMS: Rt=1.340 min, 407.1 [M+Na]$^+$.

Step 5: tert-Butyl ((1S,3R)-3-((2-bromo-6-(difluoromethyl)pyridin-3-yl)oxy)cyclopentyl)carbamate (P17-1)

To a solution of tert-butyl ((1S,3R)-3-((2-bromo-6-formylpyridine-3-yl)oxy)cyclopentyl)carbamate (220 mg, 0.57 mmol) in anhydrous dichloromethane (10 mL) was added bis(2-methoxyethyl)aminosulfur trifluoride (BAST, 378 mg, 1.71 mmol) at 0° C. The reaction mixture was heated to 40° C. for 1 h under nitrogen. The reaction mixture was poured into water (60 mL) and extracted with dichloromethane (3×40 mL). The combined organic layers were washed with brine (40 mL), dried over sodium sulfate, filtered, and evaporated. The residue was purified by gradient silica gel column chromatography to give the title compound (150 mg, 65% yield) as a yellow solid. LCMS: Rt=1.331 min. ESMS m/z=407.1 [M+H]$^+$.

Preparation P18-1: tert-Butyl ((1S,3R)-3-(2-bromo-3-(methoxy-d₃)phenoxy)cyclopentyl)carbamate

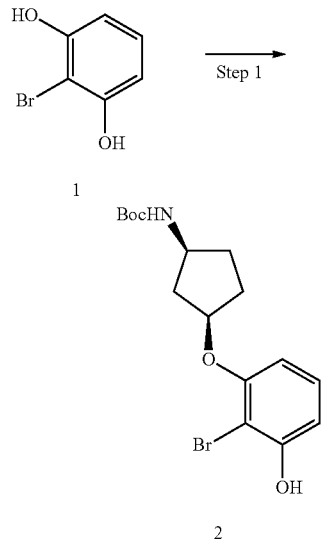

Step 1: tert-Butyl ((1S,3R)-3-(2-bromo-3-hydroxyphenoxy)cyclopentyl)carbamate (2)

To a solution of 2-bromobenzene-1,3-diol (220 mg, 1.17 mmol), tert-butyl ((1S,3S)-3-hydroxycyclopentyl) carbamate (235 mg, 1.17 mmol) and triphenylphosphine (613 mg, 2.34 mmol) in tetrahydrofuran (5 mL) at 0° C. was added diisopropyl azodicarboxylate (460 µL, 2.34 mmol). The reaction mixture was warmed to room temperature and was stirred for 2 h. The reaction was quenched with water (20 mL) and the mixture was extracted with ethyl acetate (3×20 mL). The combined organic layers were dried over sodium sulfate, filtered, and evaporated. The crude product was purified by gradient silica gel column chromatography to give the title compound (180 mg, 41% yield) as a yellow solid. LCMS: Rt=1.307 min, ESMS m/z=393.9 [M+Na]⁺.

Step 2: tert-Butyl ((1S,3R)-3-(2-bromo-3-(methoxy-d₃)phenoxy)cyclopentyl)carbamate (P18-1)

To a mixture of tert-butyl ((1S,3R)-3-(2-bromo-3-hydroxyphenoxy)cyclopentyl)carbamate (126 mg, 0.34 mmol) and potassium carbonate (70 mg, 0.51 mmol) in acetonitrile (5 mL) was added iodomethane-d₃ (106 µL, 1.70 mmol) dropwise. The reaction mixture was stirred at room temperature for 18 h. The reaction was quenched with water (50 mL) and the mixture was extracted with ethyl acetate (3×30 mL). The combined organic layers were dried over sodium sulfate, filtered, and evaporated. The crude product was purified by gradient silica gel column chromatography to give the title compound (100 mg, 75% yield) as a yellow solid. LCMS: Rt=1.419 min, ESMS m/z=411.1 [M+Na]⁺.

Preparation P19-1: tert-Butyl (2-((2-bromo-3-methoxyphenoxy)methyl)cyclopropyl)carbamate

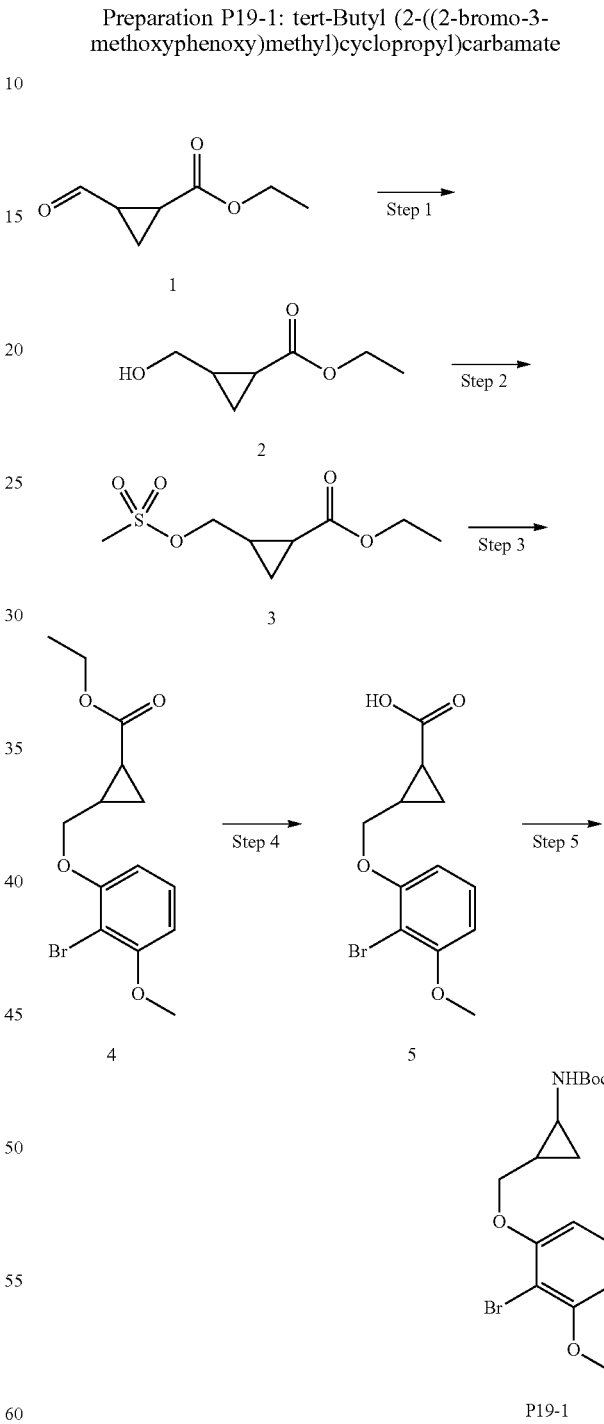

Step 1: Ethyl 2-(hydroxymethyl)cyclopropane-1-carboxylate (2)

To a mixture of ethyl 2-formylcyclopropane-1-carboxylate (5 g, 35 mmol) in anhydrous ethanol (50 mL) was added sodium borohydride (3.99 g, 105 mmol) at 0° C. and the reaction mixture was stirred at room temperature for 2 h under nitrogen. The mixture was cooled to 0° C. and the reaction was quenched with 1 N hydrochloric acid (10 mL). The mixture was poured into water (50 mL) and extracted with dichloromethane (3×60 mL). The combined organic layers were washed with brine (60 mL), dried over sodium sulfate, filtered, and evaporated. The residue was purified by gradient silica gel column chromatography to afford the title compound (5 g, 80% yield) as a white oil. LCMS: Rt=0.947 min, ESMS m/z=145.1 [M+H]$^+$.

Step 2: Ethyl 2-(((methylsulfonyl)oxy)methyl)cyclopropane-1-carboxylate (3)

To a mixture of ethyl 2-(hydroxymethyl)cyclopropane-1-carboxylate (5 g, 34.7 mmol) and methanesulfonic anhydride (6.65 g, 38.2 mmol) in dichloromethane (35 mL was added triethylamine (7.74 mL, 41.6 mmol) and the reaction mixture was stirred at room temperature for 18 h under nitrogen. The mixture was poured into water (20 mL) and extracted with dichloromethane (3×20 mL). The combined organic layers were washed with brine (20 mL), dried over sodium sulfate, filtered, and evaporated. The residue was purified by gradient silica gel column chromatography to afford the title compound (4 g, 42% yield) as a white oil. LCMS: Rt=1.109 min, ESMS m/z=223.1 [M+H]$^+$.

Step 3: Ethyl 2-((2-bromo-3-methoxyphenoxy)methyl)cyclopropane-1-carboxylate (4)

To a mixture of ethyl 2-(((methylsulfonyl)oxy)methyl)cyclopropane-1-carboxylate (4 g, 18 mmol) and 2-bromo-3-methoxyphenol (4.75 g, 23.4 mmol) in N,N-dimethylformamide (15 mL) was added cesium carbonate (8.21 g, 25.2 mmol) and the reaction mixture was heated to 65° C. for 18 h under nitrogen. The reaction mixture was poured into water (20 mL) and extracted with dichloromethane (3×20 mL). The combined organic layers were washed with brine (20 mL), dried over sodium sulfate, filtered, and evaporated. The crude product was purified by gradient silica gel column chromatography to give the title compound (2.6 g, 39% yield) as a colorless oil. LCMS: Rt=1.374 min, ESMS m/z=329.0 [M+H]$^+$.

Step 4: 2-((2-Bromo-3-methoxyphenoxy)methyl)cyclopropane-1-carboxylic acid (5)

To a solution of ethyl 2-((2-bromo-3-methoxyphenoxy)methyl)cyclopropane-1-carboxylate (2.6 g, 7.92 mmol) in methanol (10 mL) was added sodium hydroxide (4 M aqueous solution, 5 mL, 20 mmol) and the reaction mixture was stirred at room temperature for 18 h under nitrogen. The reaction mixture was poured into water (20 mL) and extracted with dichloromethane (3×10 mL). The combined organic layers were washed with brine (15 mL), dried over sodium sulfate, filtered, and evaporated. The crude product was purified by gradient silica gel column chromatography to give the title compound (2 g, 77% yield) as a white oil. LCMS: Rt=1.199 min, ESMS m/z=301.0 [M+H]$^+$.

Step 5: tert-butyl (2-((2-bromo-3-methoxyphenoxy)methyl)cyclopropyl)carbamate (P19-1)

To a solution of 2-((2-bromo-3-methoxyphenoxy)methyl)cyclopropane-1-carboxylic acid (400 mg, 1.33 mmol) in dichloromethane (10 mL) was added oxalyl chloride (337 µL, 3.99 mmol) and N,N-dimethylformamide (2 drops) at 0° C. The reaction mixture was stirred at room temperature for 2 h. The mixture was evaporated and the residue was dissolved in N,N-dimethylformamide (6 mL). To the solution was added sodium azide (259 mg, 3.99 mmol) at 0° C. The reaction mixture was stirred at room temperature for 2 hours. The mixture was poured into water (20 mL) and extracted with ethyl acetate (3×20 mL). The combined organic layers were washed with brine (20 mL), dried over sodium sulfate, filtered, and evaporated. The residue was taken up in a mixture of toluene and tert-butanol (5:1, 6 mL) and the reaction mixture was heated to 110° C. for 18 h. The mixture was poured into water (20 mL) and extracted with dichloromethane (3×20 mL). The combined organic layers were washed with brine (20 mL), dried over sodium sulfate, filtered, and evaporated. The crude product was purified by gradient silica gel column chromatography to furnish the title compound (260 mg, 55% yield) as a colorless oil. LCMS: Rt=1.383 min, ESMS m/z=393.9 [M+Na]$^+$.

Preparation P20-1: 5-((5-(3-Fluoro-2-hydroxy-6-methoxyphenyl)-1H-pyrazol-3-yl)amino)pyrazine-2-carbonitrile

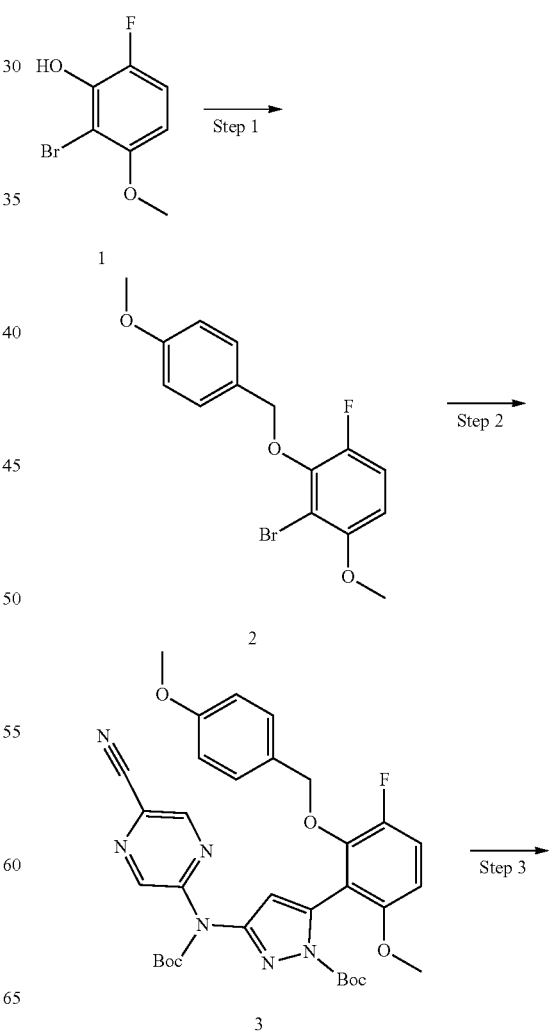

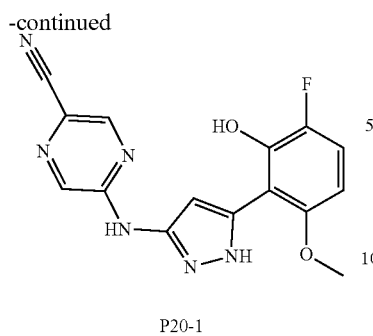

P20-1

Step 1: 2-Bromo-4-fluoro-1-methoxy-3-((4-methoxybenzyl)oxy)benzene (2)

To a mixture of 2-bromo-6-fluoro-3-methoxyphenol (420 mg, 1.9 mmol) and potassium carbonate (525 mg, 3.8 mmol) in N,N-dimethylformamide (10 mL) was added 4-methoxybenzyl chloride (335 μL, 2.47 mmol) dropwise over 2 min at 0° C. The reaction mixture was stirred at room temperature for 6 h. The mixture was poured into water (20 mL) and extracted with ethyl acetate (3×30 mL). The combined organic layers were washed with brine, dried over sodium sulfate, filtered, and evaporated. The residue was purified by gradient silica gel column chromatography to furnish the title compound (230 mg, 36% yield) as a white solid. LCMS: Rt=1.312 min, ESMS m/z=363.0 [M+Na]$^+$.

Step 2: tert-Butyl 3-((tert-butoxycarbonyl)(5-cyano-pyrazin-2-yl)amino)-5-(3-fluoro-6-methoxy-2-((4-methoxybenzyl)oxy)phenyl)-1H-pyrazole-1-carboxylate (3)

To a solution of 2-bromo-4-fluoro-1-methoxy-3-((4-methoxybenzyl)oxy)benzene (220 mg, 0.64 mmol), tert-butyl 3-((tert-butoxycarbonyl)(5-cyanopyrazin-2-yl)amino)-5-(4,4,5,5-tetramethyl-1,3,2-dioxaborolan-2-yl)-1H-pyrazole-1-carboxylate (532 mg, 1.29 mmol), 2-dicyclohexylphosphino-2',4',6'-triisopropylbiphenyl (XPhos, 46 mg, 0.097 mmol) and tripotassium phosphate (274 mg, 1.29 mmol) in a mixture of 1,4-dioxane and water (5:1, 12 mL) was added tris(dibenzylideneacetone)dipalladium(0) (88 mg, 0.097 mmol) and the reaction mixture was stirred at 90° C. for 3 h under nitrogen. The mixture was poured into water (20 mL) and extracted with ethyl acetate (3×20 mL). The combined organic layers were washed with brine (20 mL), dried over sodium sulfate, filtered, and evaporated. The residue was purified by gradient silica gel column chromatography to afford the title compound (220 mg, 56% yield) as a yellow solid. LCMS: Rt=1.527 min, ESMS m/z=669.1 [M+Na]$^+$.

Step 3: 5-((5-(3-Fluoro-2-hydroxy-6-methoxyphenyl)-1H-pyrazol-3-yl)amino)pyrazine-2-carbonitrile (P20-1)

A mixture of tert-butyl 3-((tert-butoxycarbonyl)(5-cyano-pyrazin-2-yl)amino)-5-(3-fluoro-6-methoxy-2-((4-methoxybenzyl)oxy)phenyl)-1H-pyrazole-1-carboxylate (220 mg, 0.40 mmol) and hydrogen chloride (4 M in 1,4-dioxane, 2.5 mL, 10 mmol) was stirred at room temperature for 1 h. The reaction mixture was evaporated and the crude product was purified by gradient silica gel column chromatography to give the title compound (60 mg, 43% yield) as a yellow solid. LCMS: Rt=1.201 min, ESMS m/z=327.0 [M+H]$^+$.

Example 1-1: 5-((5-(2-(((1r,4r)-4-Aminocyclohexyl)oxy)-6-methoxyphenyl)-1H-pyrazol-3-yl)amino)pyrazine-2-carbonitrile

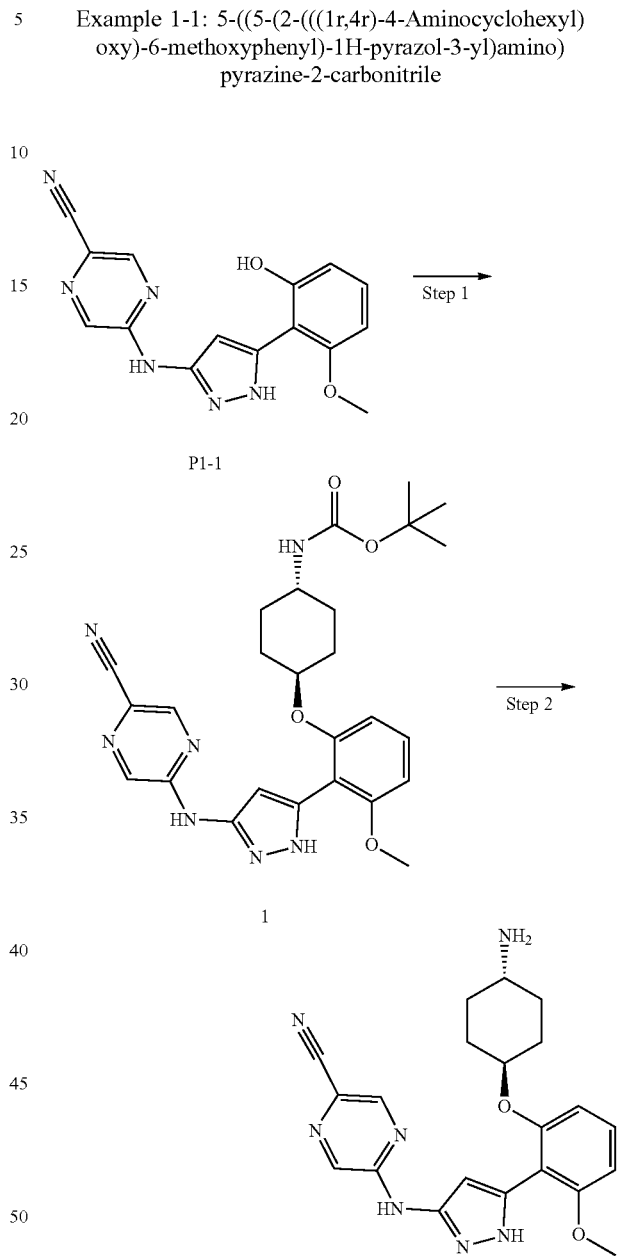

Example 1

Step 1: tert-Butyl ((1r,4r)-4-(2-(3-((5-cyanopyrazin-2-yl)amino)-1H-pyrazol-5-yl)-3-methoxyphenoxy)cyclohexyl)carbamate (1)

To a solution of 5-((5-(2-hydroxy-6-methoxyphenyl)-1H-pyrazol-3-yl)amino)pyrazine-2-carbonitrile (200 mg, 0.649 mmol), cis-4-(tert-butoxycarbonylamino)cyclohexanol (279 mg, 1.30 mmol) and triphenylphosphine (511 mg, 1.95 mmol) in tetrahydrofuran (5 mL) under nitrogen at 0° C. was added a solution of diisopropylazadicarboxylate (394 mg, 1.95 mmol) in tetrahydrofuran (1 mL) dropwise. The reaction mixture was stirred at room temperature for 18 h. The reaction was quenched with water (20 mL) and the mixture was extracted with ethyl acetate (3×20 mL). The combined organic layers were dried over sodium sulfate, filtered, and evaporated. The crude product was purified by gradient silica gel column chromatography to afford the title compound as a yellow solid (120 mg, 36% yield). LCMS: Rt=1.233 min, ESMS m/z=506.2 [M+H]+.

Step 2: 5-((5-(2-(((1r,4r)-4-Aminocyclohexyl)oxy)-6-methoxyphenyl)-1H-pyrazol-3-yl)amino)pyrazine-2-carbonitrile formic acid salt To a solution of tert-butyl ((1r,4r)-4-(2-(3-((5-cyanopyrazin-2-yl)amino)-1H-pyrazol-5-yl)-3-methoxyphenoxy)cyclohexyl) carbamate (120 mL, 0.23 mmol) in dichloromethane (2 mL) was added hydrogen chloride (4M in 1,4-dioxane, 2 mL, 8 mmol) and the reaction mixture was stirred at room temperature for 1 hour. The mixture was evaporated and the residue was purified by preparative HPLC to afford the title compound (30 mg, 31% yield) as a white solid. LCMS: Rt=3.952 min, ESMS m/z=406.2 [M+H]+. 1H NMR (400 MHz, CD3OD) δ ppm 8.53 (s, 1H), 8.50 (d, J=1.2 Hz, 1H), 8.47 (s, 1H), 7.34 (t, J=8.4 Hz, 1H), 6.96 (s, 1H), 6.82 (d, J=8 Hz, 1H), 6.79 (d, J=8.4 Hz, 1H), 4.40-4.34 (m, 1H), 3.90 (s, 3H), 3.21-3.15 (m, 1H), 2.26-2.22 (m, 2H), 2.14-2.06 (m, 2H), 1.67-1.49 (m, 4H).

The following compounds were prepared by the same general method:

| Ex. | MW | LC-MS (m/z) |
|---|---|---|
| 1-2 | 391.18 | 392.2 |
| 1-3 | 391.18 | 391.8 |
| 1-4 | 377.16 | 377.8 |
| 1-5 | 377.16 | 378.1 |
| 1-6 | 391.18 | 392.2 |
| 1-7 | 391.18 | 391.8 |
| 1-8 | 391.18 | 392.2 |
| 1-9 | 347.15 | 348.2 |
| 1-10 | 347.15 | 348.2 |
| 1-11 | 405.19 | 406.1 |
| 1-12 | 391.44 | 392.1 |
| 1-13 | 365.37 | 366.0 |
| 1-14 | 395.40 | 395.6 |
| 1-15 | 405.46 | 406.2 |
| 1-16 | 391.44 | 392.1 |
| 1-17 | 419.49 | 420.0 |
| 1-18 | 433.52 | 434.3 |
| 1-19 | 393.43 | 394.2 |
| 1-20 | 423.45 | 424.0 |
| 1-21 | 439.90 | 440.1 |
| 1-22 | 379.40 | 379.9 |
| 1-23 | 405.46 | 405.7 |
| 1-24 | 419.49 | 420.2 |
| 1-25 | 459.43 | 460.0 |
| 1-26 | 409.43 | 410.0 |
| 1-27 | 409.43 | 410.2 |
| 1-28 | 409.43 | 410.2 |
| 1-29 | 425.88 | 425.6 |
| 1-30 | 405.46 | 406.0 |
| 1-31 | 445.53 | 446.1 |
| 1-32 | 417.47 | 418.2 |
| 1-33 | 431.50 | 432.1 |
| 1-34 | 445.53 | 446.2 |
| 1-35 | 417.47 | 418.1 |
| 1-36 | 431.50 | 432.0 |
| 1-37 | 361.41 | 361.9 |
| 1-38 | 361.41 | 362.2 |
| 1-39 | 405.46 | 406.2 |
| 1-40 | 375.44 | 376.1 |
| 1-41 | 409.43 | 410.2 |
| 1-42 | 375.44 | 376.3 |

-continued

| Ex. | MW | LC-MS (m/z) |
|---|---|---|
| 1-43 | 393.43 | 394.1 |
| 1-44 | 379.40 | 380.0 |
| 1-45 | 419.49 | 420.0 |
| 1-46 | 405.46 | 406.2 |
| 1-47 | 405.46 | 406.0 |
| 1-48 | 419.49 | 420.2 |
| 1-49 | 419.49 | 420.0 |
| 1-50 | 375.44 | 376.3 |
| 1-51 | 375.44 | 375.8 |
| 1-52 | 361.41 | 362.2 |
| 1-53 | 361.41 | 362.2 |
| 1-54 | 387.45 | 388.1 |
| 1-55 | 348.37 | 349.2 |
| 1-56 | 390.45 | 391.0 |
| 1-57 | 376.42 | 377.0 |
| 1-58 | 362.40 | 363.2 |
| 1-59 | 362.40 | 363.1 |
| 1-60 | 376.42 | 377.1 |
| 1-61 | 376.42 | 377.0 |
| 1-62 | 362.40 | 363.0 |
| 1-63 | 362.40 | 363.2 |
| 1-64 | 405.2 | 406.2 |
| 1-65 | 405.2 | 406.2 |
| 1-66 | 405.2 | 405.7 |

Example 2: 5-((5-(2-((((1S,3R)-3-Aminocyclopentyl)oxy)phenyl)-1H-pyrazol-3-yl)amino)pyrazine-2-carbonitrile

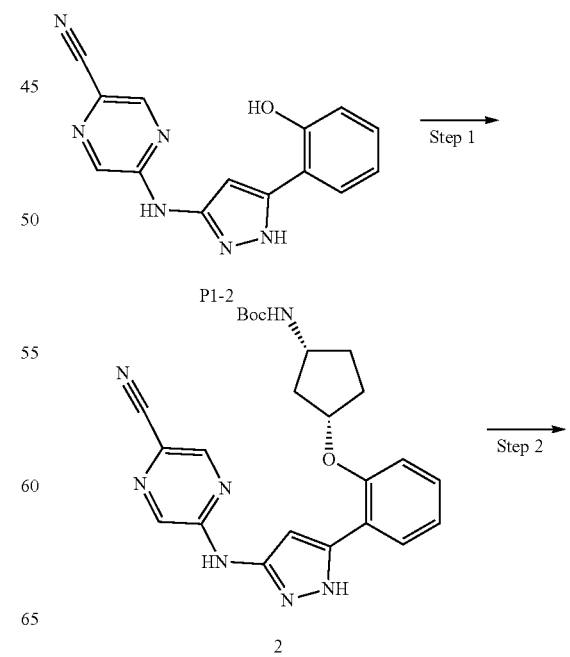

143

-continued

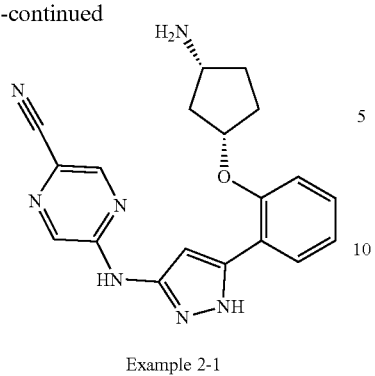

Example 2-1

Step 1: tert-Butyl ((1R,3S)-3-(2-(3-((5-cyanopy-razin-2-yl)amino)-1H-pyrazol-5-yl)phenoxy)cyclopentyl)carbamate (2)

A mixture of crude (1R,3R)-3-((tert-butoxycarbonyl)amino)cyclopentyl methanesulfonate (300 mg, 1.07 mmol), 5-((5-(2-hydroxyphenyl)-1H-pyrazol-3-yl)amino)pyrazine-2-carbonitrile (269 mg, 0.96 mmol) and cesium carbonate (697 mg, 2.14 mmol) in anhydrous tetrahydrofuran (10 mL) was stirred at 70° C. for 18 h under nitrogen. The reaction was quenched with water (20 mL) and the mixture was extracted with ethyl acetate (3×30 mL). The combined organic layers were dried over anhydrous sodium sulfate, filtered and evaporated. The residue was purified by gradient silica gel column chromatography to afford the title compound (150 mg, 34% yield) as a colorless oil. LCMS (method 1): Rt=1.449 min, ESMS m/z=461.7 [M+H]⁺.

Step 2: 5-((5-(2-(((1S,3R)-3-Aminocyclopentyl)oxy)phenyl)-1H-pyrazol-3-yl)amino)pyrazine-2-carbonitrile formic acid salt To a mixture of tert-butyl ((1R,3S)-3-(2-(3-((5-cyanopyrazin-2-yl)amino)-1H-pyrazol-5-yl)phenoxy)cyclopentyl)carbamate (150 mg, 0.32 mmol) in ethyl acetate (5 mL) was added hydrogen chloride (4M in 1,4-dioxane, 5 mL, 20 mmol) at 0° C. The reaction mixture was warmed to room temperature and stirred for 1 h. The reaction mixture was evaporated and the residue was purified by preparative HPLC to afford the title compound (24 mg, 20% yield) as a white solid. LCMS (method 1): Rt=0.917 min, ESMS m/z=362.2 [M+H]⁺. ¹H NMR (400 MHz, DMSO-d₆) δ ppm 8.66 (d, J=1.2 Hz, 1H), 8.49 (br s, 1H), 8.33 (s, 1H), 7.68 (dd, J=7.6, 1.6 Hz, 1H), 7.35-7.29 (m, 1H), 7.13 (d, J=8.4 Hz, 1H), 7.05-6.09 (m, 2H), 5.06-4.94 (m, 1H), 3.63-3.52 (m, 1H), 2.31-2.25 (m, 1H), 2.02-1.93 (m, 3H), 1.84-1.76 (m, 1H), 1.73-1.64 (m, 1H).

The following compounds were prepared by the same general method:

| Ex. | MW | LC-MS (m/z) |
|-----|--------|-------------|
| 2-2 | 391.44 | 392.0 |
| 2-3 | 395.40 | 396.0 |
| 2-4 | 423.45 | 424.0 |
| 2-5 | 379.40 | 380.2 |

144

Example 3-1: 5-((5-(2,3-Difluoro-6-(((1R,3R)-3-(methylamino)cyclopentyl)oxy)phenyl)-1H-pyrazol-3-yl)amino)pyrazine-2-carbonitrile

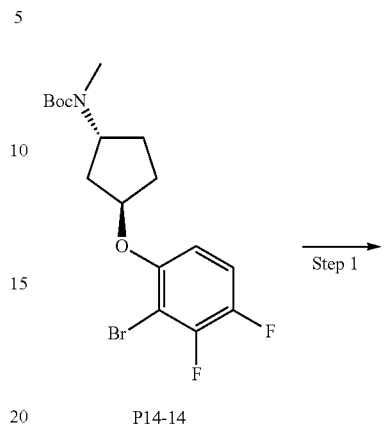

P14-14

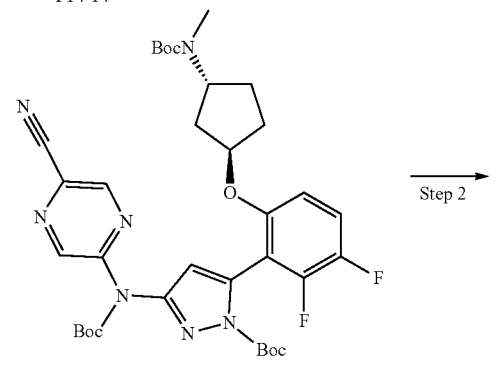

2

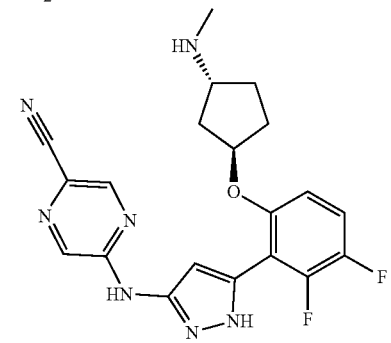

Example 3-1

Step 1: tert-Butyl 3-((tert-butoxycarbonyl)(5-cyano-pyrazin-2-yl)amino)-5-(6-(((1R,3R)-3-((tert-butoxycarbonyl)(methyl)amino)cyclopentyl)oxy)-2,3-difluorophenyl)-1H-pyrazole-1-carboxylate (2)

To a solution of tert-butyl ((1R,3R)-3-(2-bromo-3,4-difluorophenoxy) cyclopentyl)(methyl)carbamate (150 mg, 0.37 mmol), tert-butyl 3-((tert-butoxycarbonyl)(5-cyanopyrazin-2-yl)amino)-5-(4,4,5,5-tetramethyl-1,3,2-dioxaborolan-2-yl)-1H-pyrazole-1-carboxylate (P12-1, 227 mg, 0.44 mmol), sodium carbonate (117 mg, 1.11 mmol) in a mixture of 1,4-dioxane and water (5:1, 6 mL) was added tetrakis (triphenylphosphine)palladium(0) (85 mg, 0.07 mmol) and the reaction mixture was stirred at 90° C. for 2.5 h under nitrogen. The reaction mixture was poured into water (20 mL) and extracted with ethyl acetate (3×20 mL). The combined organic layers were washed with brine (30 mL), dried over sodium sulfate, filtered and evaporate. The residue was purified by gradient silica gel column chromatography to afford the title compound (80 mg, 30% yield) as a white solid. LCMS (method 1): Rt 1.379 m) ESMS m/z=512.1 [M+H-2Boc]7.

Step 2: 5-((5-(2,3-Difluoro-6-(((1R,3R)-3-(methylamino)cyclopentyl)oxy)phenyl)-1H-pyrazol-3-yl)amino)pyrazine-2-carbonitrile formic acid salt To a solution of tert-butyl 3-((tert-butoxycarbonyl)(5-cyanopyrazin-2-yl)amino)-5-(6-(((1R,3S)-3-((tert-butoxycarbonyl)amino)cyclopentyl)oxy)-2,3-difluorophenyl)-1H-pyrazole-1-carboxylate (80 mg, 0.11 mmol) in dichloromethane (3 mL) was added trifluoroacetic acid (0.5 mL, 6.53 mmol) and the reaction mixture was stirred at room temperature for 2 h. The reaction mixture was evaporated. To the residue was added saturated aqueous sodium carbonate (3 mL) to achieve pH 8. To the mixture was added formic acid (5 mL) until a clear solution formed. The mixture was purified by preparative HPLC to afford the title compound (6.9 mg, 15% yield) as a white solid. LCMS (method 1): Rt=1.087 min, ESMS m/z=412.0 [M+H]$^+$. $^1$H NMR (400 MHz, DMSO-d$_6$) δ ppm 12.70 (s, 1H), 10.93 (s, 1H), 8.68 (s, 1H), 8.50 (s, 1H), 8.35 (s, 1H), 7.52-7.40 (m, 1H), 7.06-6.85 (m, 2H), 5.02-4.95 (m, 1H), 3.41-3.32 (m, 1H), 2.38 (s, 3H), 2.20-2.07 (m, 2H), 2.05-1.98 (m, 1H), 1.95-1.86 (m, 1H), 1.82-1.72 (m, 1H), 1.67-1.56 (m, 1H).

The following compounds were prepared by the same general method:

| Ex. | MW | LC-MS (m/z) |
| --- | --- | --- |
| 3-2 | 377.41 | 378.0 |
| 3-3 | 377.41 | 378.1 |
| 3-4 | 377.41 | 378.0 |
| 3-5 | 377.41 | 378.2 |
| 3-6 | 419.49 | 420.1 |
| 3-7 | 419.49 | 420.1 |
| 3-8 | 419.49 | 420.1 |
| 3-9 | 419.49 | 420.0 |
| 3-10 | 417.47 | 418.2 |
| 3-11 | 417.47 | 418.2 |
| 3-12 | 375.44 | 376.2 |
| 3-13 | 379.40 | 380.1 |
| 3-14 | 395.85 | 396.2 |
| 3-15 | 394.45 | 395.2 |
| 3-16 | 393.43 | 394.1 |
| 3-17 | 393.43 | 394.0 |
| 3-18 | 397.39 | 398.0 |
| 3-19 | 413.84 | 414.1 |
| 3-20 | 407.45 | 408.0 |
| 3-21 | 407.45 | 408.2 |
| 3-22 | 427.87 | 428.1 |
| 3-23 | 445.14 | 446.2 |
| 3-24 | 413.84 | 414.2 |
| 3-25 | 427.87 | 428.0 |
| 3-26 | 393.43 | 394.2 |
| 3-27 | 393.43 | 394.1 |
| 3-28 | 397.39 | 398.2 |
| 3-29 | 413.84 | 414.1 |
| 3-30 | 413.84 | 414.1 |
| 3-31 | 365.37 | 366.0 |
| 3-32 | 365.37 | 366.0 |
| 3-33 | 365.37 | 366.0 |
| 3-34 | 365.37 | 366.0 |
| 3-35 | 407.45 | 408.0 |
| 3-36 | 407.45 | 408.1 |
| 3-37 | 407.45 | 408.2 |
| 3-38 | 407.45 | 408.2 |
| 3-39 | 379.40 | 380.2 |
| 3-40 | 379.40 | 380.0 |
| 3-41 | 405.44 | 406.0 |
| 3-42 | 362.40 | 363.2 |
| 3-43 | 376.42 | 377.2 |
| 3-44 | 376.42 | 377.1 |
| 3-45 | 390.45 | 391.0 |
| 3-46 | 404.48 | 405.1 |
| 3-47 | 404.48 | 405.1 |
| 3-48 | 390.45 | 391.2 |
| 3-49 | 430.40 | 431.1 |
| 3-50 | 394.41 | 395.0 |
| 3-51 | 412.43 | 413.0 |
| 3-52 | 410.87 | 411.1 |
| 3-53 | 410.87 | 411.2 |
| 3-54 | 412.40 | 413.1 |
| 3-55 | 377.16 | 378.0 |

Example 4-1: 5-((5-(6-(((1R,3S)-3-Aminocyclopentyl)oxy)-2-methoxy-3-methylphenyl)-1H-pyrazol-3-yl)amino)pyrazine-2-carbonitrile

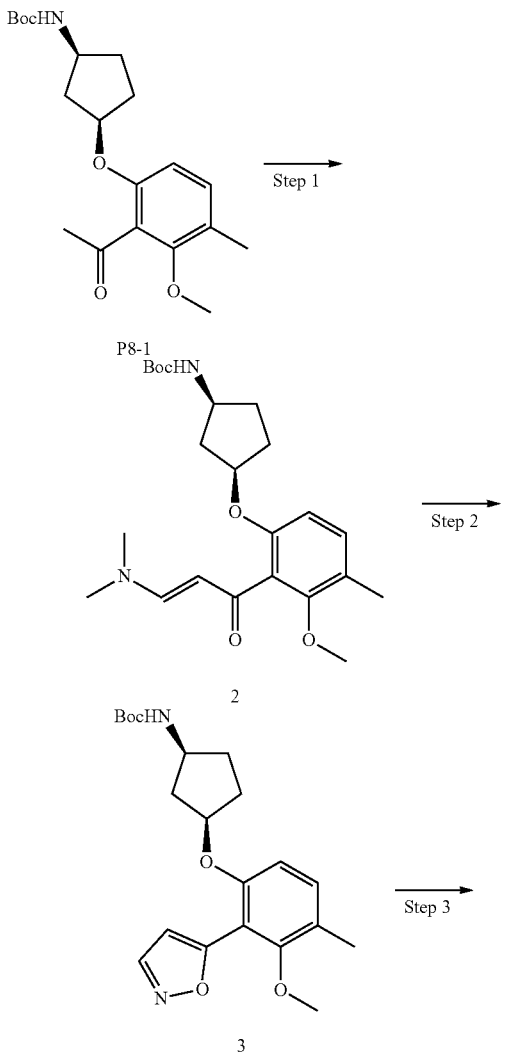

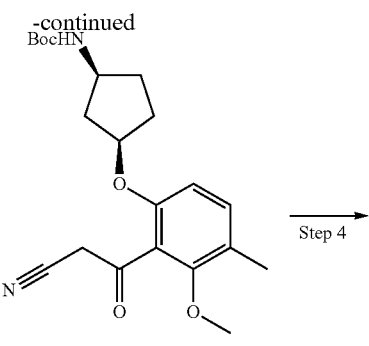

4

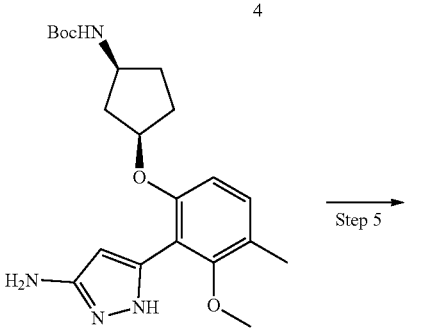

5

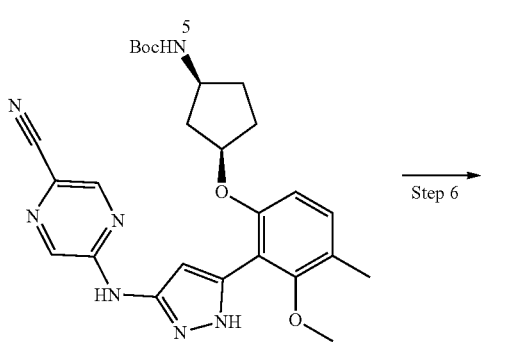

6

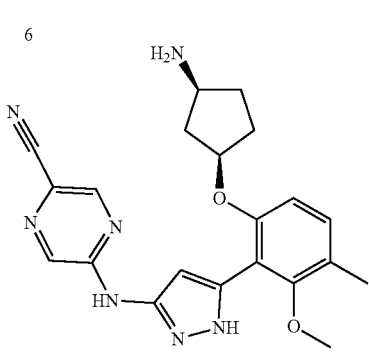

Example 4-1

Step 1: tert-Butyl ((1S,3R)-3-(2-(3-(dimethylamino) acryloyl)-3-methoxy-4-methylphenoxy)cyclopentyl) carbamate (2)

A mixture of tert-butyl ((1S,3R)-3-(2-acetyl-3-methoxy-4-methylphenoxy)cyclopentyl)carbamate (650 mg, 1.79 mmol) and N,N-dimethylformamide dimethyl acetal (920 µL, 7.15 mmol) in anhydrous N,N-dimethylformamide (5 mL) was heated to 120° C. for 18 h. The mixture was evaporated to afford the crude title compound (900 mg) as a yellow oil, which was used in the next step without purification. LCMS (method 1): Rt=1.273 min, ESMS m/z=419.1 [M+H]$^+$.

Step 2: tert-Butyl ((1S,3R)-3-(2-(isoxazol-5-yl)-3-methoxy-4-methylphenoxy)cyclopentyl)carbamate (3)

A mixture of tert-butyl ((1S,3R)-3-(2-3-(dimethylamino) acryloyl)-3-methoxy-4-methylphenoxy)cyclopentyl)carbamate (900 mg, 2.15 mmol) and hydroxylamine hydrochloride (224 mg, 3.22 mmol) in anhydrous ethanol (10 mL) was stirred at 50° C. for 2 h under nitrogen. The reaction mixture was evaporated and the residue was taken up in water (30 mL). The mixture was extracted with ethyl acetate (3×20 mL) and the combined organic layers were dried over sodium sulfate, filtered and evaporated. The crude product was purified by gradient silica gel column chromatography to afford the title compound (600 mg, 82% yield over 2 steps) as a white solid. LCMS (method 1): Rt=1.404 min, ESMS m/z=411.0 [M+Na]$^+$.

Step 3: tert-Butyl ((1S,3R)-3-(2-(2-cyanoacetyl)-3-methoxy-4-methylphenoxy)cyclopentyl)carbamate (4)

A mixture of tert-butyl ((1S,3R)-3-(2-(isoxazol-5-yl)-3-methoxy-4-methylphenoxy)cyclopentyl)carbamate (350 mg, 0.91 mmol) and potassium hydroxide (77 mg, 1.36 mmol) in anhydrous ethanol (10 mL) was stirred at 50° C. for 18 h under nitrogen. The reaction mixture was evaporated. The residue was taken up in water (20 mL) and the mixture was neutralized (pH 7) by addition of saturated citric acid solution. The mixture was extracted with ethyl acetate (3×20 mL). The combined organic layers were dried over anhydrous sodium sulfate, filtered, and evaporated to give the title compound (300 mg, 86% yield) as a white solid, which was used without further purification. LCMS (method 1): Rt=1.356 min, ESMS m/z=411.0 [M+Na]$^+$.

Step 4: tert-Butyl ((1S,3R)-3-(2-(3-amino-1H-pyrazol-5-yl)-3-methoxy-4-methylphenoxy)cyclopentyl) carbamate (5)

A mixture of tert-butyl ((1S,3R)-3-(2-(2-cyanoacetyl)-3-methoxy-4-methylphenoxy)cyclopentyl)carbamate (300 mg, 0.77 mmol), hydrazine hydrate (75 µL, 1.54 mmol) and acetic acid (132 µL, 2.31 mmol) in anhydrous ethanol (10 mL) was slowly heated to 90° C. under nitrogen. The reaction mixture was stirred at 90° C. for 18 h. The reaction mixture was cooled to room temperature and evaporated. The crude product was purified by gradient silica gel column chromatography to afford the title compound (300 mg, 97% yield) as a white solid. LCMS (method 1): Rt=1.166 min, ESMS m/z=403.3 [M+H]$^+$.

Step 5: tert-Butyl ((1S,3R)-3-(2-(3-((5-cyanopyrazin-2-yl)amino)-1H-pyrazol-5-yl)-3-methoxy-4-methylphenoxy)cyclopentyl)carbamate (6)

A mixture of tert-butyl ((1S,3R)-3-(2-(3-amino-1H-pyrazol-5-yl)-3-methoxy-4-methylphenoxy)cyclopentyl)carbamate (300 mg, 0.74 mmol), 5-chloropyrazine-2-carbonitrile (114 mg, 0.82 mmol) and 4-ethylmorpholine (285 µL, 2.23 mmol) in anhydrous dimethyl sulfoxide (5 mL) was stirred at 80° C. for 3 h under nitrogen. The reaction mixture was cooled to room temperature and diluted with water (20 mL). The mixture was extracted with ethyl acetate (3×20 mL). The combined organic layers were dried over sodium sulfate, filtered, and evaporated. The crude product was purified by gradient silica gel column chromatography to afford the title compound (300 mg, 80% yield) as a yellow solid. LCMS (method 1): Rt=1.355 min, ESMS m/z=506.2 [M+H]$^+$.

Step 6: 5-((5-(6-(((1R,3S)-3-Aminocyclopentyl)oxy)-2-methoxy-3-methylphenyl)-1H-pyrazol-3-yl)amino)pyrazine-2-carbonitrile formic acid salt To a mixture of tert-butyl ((1S,3R)-3-(2-(3-((5-cyanopyrazin-2-yl)amino)-1H-pyrazol-5-yl)-3-methoxy-4-methylphenoxy)cyclopentyl)carbamate (100 mg, 0.19 mmol) in ethyl acetate (5 mL) at 0° C. was added hydrogen chloride (4M in 1,4-dioxane, 5 mL, 20 mmol). The reaction mixture was stirred at room temperature for 2 h. The reaction mixture was evaporated and the residue was purified by preparative HPLC to afford the title compound (60 mg, 75% yield) as a yellow solid. LCMS (method 1): Rt=1.060 min, ESMS m/z=406.1 [M+H]$^+$. $^1$H NMR (400 MHz, DMSO-d$_6$) δ ppm 8.65 (d, J=1.2 Hz, 1H), 8.52 (br s, 1H), 8.38 (s, 1H), 7.18 (d, J=8.8 Hz, 1H), 6.86 (s, 1H), 6.78 (d, J=8.8 Hz, 1H), 4.84-4.78 (m, 1H), 3.53-3.45 (m, 1H), 3.42 (s, 3H), 2.39-2.32 (m, 1H), 2.21 (s, 3H), 1.96-1.87 (m, 3H), 1.75-1.70 (m, 2H).

The following compounds were prepared by the same general method:

| Ex. | MW | LC-MS (m/z) |
|---|---|---|
| 4-2 | 425.88 | 426.1 |
| 4-3 | 405.48 | 406.3 |
| 4-4 | 425.88 | 426.2 |
| 4-5 | 402.46 | 403.0 |

Example 5-1: 5-((5-(2-(((1R,3R)-3-Aminocyclopentyl)oxy)-6-fluoro-4-methylphenyl)-1H-pyrazol-3-yl)amino)pyrazine-2-carbonitrile

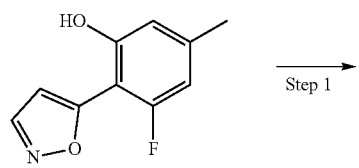

P10-1

2

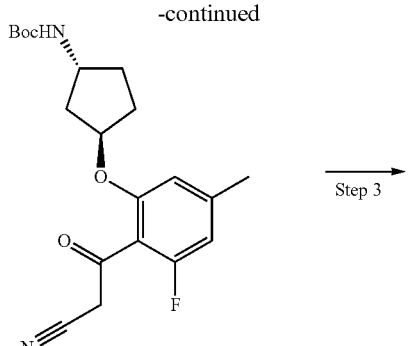

3

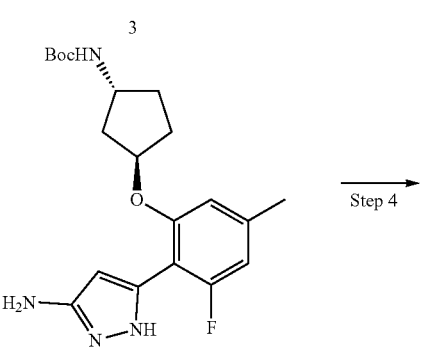

4

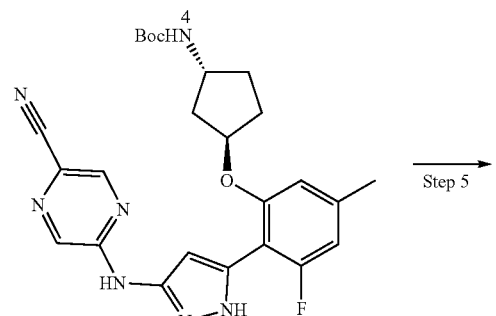

5

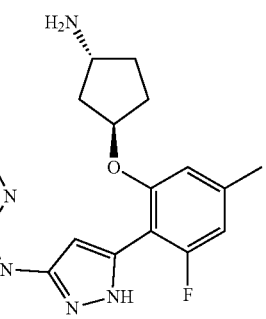

Example 5-1

Step 1: tert-Butyl ((1R,3R)-3-(3-fluoro-2-(isoxazol-5-yl)-5-methylphenoxy)cyclopentyl)carbamate (2)

To a solution of 3-fluoro-2-(isoxazol-5-yl)-5-methylphenol (400 mg, 2.07 mmol), tert-butyl ((1R,3S)-3-hydroxycyclopentyl)carbamate (833 mg, 4.14 mmol) and triphenylphosphine (1.63 g, 6.21 mmol) in anhydrous tetrahydrofuran (10 mL) was added diisopropylazodicarboxylate (1.22 mL, 6.21 mmol) at 0° C. under nitrogen. The reaction mixture was stirred at room temperature for 2 h. The reaction mixture was poured into water (30 mL) and extracted with ethyl acetate (3×20 mL). The combined organic layers were washed with brine (30 mL), dried over sodium sulfate, filtered, and evaporated. The residue was purified by gradient silica gel column chromatography to give the title compound (700 mg, 90% yield) as a white solid. LCMS (method 1): Rt=1.411 min, ESMS m/z=399.0 [M+Na]$^+$.

Step 2: tert-Butyl ((1R,3R)-3-(2-(2-cyanoacetyl)-3-fluoro-5-methylphenoxy)cyclopentyl)carbamate (3)

A mixture of tert-butyl ((1R,3R)-3-(3-fluoro-2-(isoxazol-5-yl)-5-methylphenoxy)cyclopentyl)carbamate (700 mg, 1.86 mmol) and potassium hydroxide (150 mg, 3.72 mmol) in anhydrous ethanol (15 mL) was stirred at 50° C. for 2 h under nitrogen. The reaction mixture was evaporated and the residue was taken up in water (20 mL). The mixture was neutralized (pH 7) by addition of saturated citric acid solution. The mixture was extracted with ethyl acetate (3×20 mL). The combined organic layers were dried over sodium sulfate, filtered, and evaporated to give the title compound (600 mg, 86% yield) as a white solid. LCMS (method 1): Rt=1.305 min, ESMS m/z=398.9 [M+Na]$^+$.

Step 3: tert-Butyl ((1R,3R)-3-(2-(3-amino-1H-pyrazol-5-yl)-3-fluoro-5-methylphenoxy)cyclopentyl)carbamate (4)

A mixture of tert-butyl ((1R,3R)-3-(2-(2-cyanoacetyl)-3-fluoro-5-methylphenoxy)cyclopentyl)carbamate (900 mg, 2.39 mmol), hydrazine hydrate (697 μL, 14.34 mmol) and acetic acid (547 μL, 9.56 mmol) in anhydrous ethanol (10 mL) was slowly heated to 50° C. and the reaction mixture was stirred for 3 h under nitrogen. The reaction mixture was cooled to room temperature and evaporated. The residue was purified by gradient silica gel column chromatography to afford the title compound (700 mg, 75% yield) as a white solid. LCMS (method 1): Rt=1.189 min, ESMS m/z=391.2 [M+H]$^+$.

Step 4: tert-Butyl ((1R,3R)-3-(2-(3-((5-cyanopyrazin-2-yl)amino)-1H-pyrazol-5-yl)-3-fluoro-5-methylphenoxy)cyclopentyl)carbamate (5)

A mixture of tert-butyl N-[(1R,3R)-3-[2-(5-amino-2H-pyrazol-3-yl)-3-fluoro-5-methylphenoxy]cyclopentyl]-N-methylcarbamate (200 mg, 0.51 mmol), 5-chloropyrazine-2-carbonitrile (107 mg, 0.77 mmol) and 4-ethylmorpholine (208 μL, 1.63 mmol) in anhydrous dimethyl sulfoxide (7 mL) was stirred at 80° C. for 3 h under nitrogen. The reaction mixture was cooled to room temperature and diluted with water (20 mL). The mixture was extracted with ethyl acetate (3×20 mL). The combined organic layers were dried over sodium sulfate, filtered, and evaporated. The residue was purified by gradient silica gel column chromatography to afford the title compound (150 mg, 53% yield) as a yellow solid. LCMS (method 1): Rt=1.362 min, ESMS m/z=494.3 [M+H]$^+$.

Step 5: 5-((5-(2-(((1R,3R)-3-Aminocyclopentyl)oxy)-6-fluoro-4-methylphenyl)-1H-pyrazol-3-yl)amino)pyrazine-2-carbonitrile formic acid salt To a solution of tert-butyl ((1R,3R)-3-(2-(3-((5-cyanopyrazin-2-yl)amino)-1H-pyrazol-5-yl)-3-fluoro-5-methylphenoxy)cyclopentyl)carbamate (100 mg, 0.21 mmol) in dichloromethane (3 mL) was added trifluoroacetic acid (3 mL) and the reaction mixture was stirred at room temperature for 30 min. The solvent reaction mixture was evaporated. To the residue was added saturated aqueous sodium carbonate (3 mL) to achieve pH 8. To the mixture was added formic acid (5 mL) until a clear solution formed. The solution was purified by preparative HPLC to afford the title compound (44 mg, 54% yield) as a yellow solid. LCMS (method 1): Rt=1.095 min, ESMS m/z=394.2 [M+H]$^+$. 1H NMR (400 MHz, DMSO-d$_6$) δ ppm 12.48 (s, 1H), 8.68 (d, J=1.6 Hz, 1H), 8.51 (s, 1H), 8.41 (s, 1H), 6.87-6.75 (m, 3H), 5.06-5.01 (m, 1H), 3.68-3.60 (m, 1H), 2.35 (s, 3H), 2.22-2.12 (m, 2H), 2.12-2.03 (m, 1H), 1.99-1.88 (m, 1H), 1.83-1.74 (m, 1H), 1.66-1.55 (m, 1H).

The following compounds were prepared by the same general method:

| Ex. | MW | LC-MS (m/z) |
| --- | --- | --- |
| 5-2 | 393.43 | 394.1 |
| 5-3 | 407.45 | 408.2 |
| 5-4 | 407.45 | 408.2 |

Example A: Kinase HTRF Biochemical Assay

Chk1 enzyme activity was measured using an HTRF KinEASE assay (Cisbio, catalog no. 62ST1PEC). Full-length human Chk1 protein (GenBank accession number NP_001265.1) was obtained from Carna Biosciences, Inc. (Kobe, Japan, catalog no. 02-117). The enzyme reaction was carried out in assay buffer containing (final concentrations): Chk1 enzyme (0.012 ng/μL), MgCl$_2$ (5 mM) and DTT (1 mM). To determine compound dose response, DMSO stock solutions were serially diluted in a 10-point concentration series in duplicate. Compound solution (50 nL) was added to 384-well assay plates (Greiner, catalog no. 784075). To each well containing compound solution was added assay buffer solution (5 μL). Plates were centrifuged at 1000 rpm for 1 minute, then incubated at room temperature for 10 minutes. The reaction was started by addition of substrate buffer (5 μL/well) containing (final concentrations): STK substrate 1-biotin (120 nM) and ATP (1 mM). Assay plates were centrifuged at 1000 rpm for 1 minute, then incubated at room temperature for 60 minutes. The reaction was stopped by addition of detection buffer (Cisbio, 10 μL) containing (final concentrations): STK antibody-cryptate (0.25 nM) and streptavidin-XL665 (7.5 nM). Plates were centrifuged at 1000 rpm for 1 minute, then incubated at 25° C. for 2 hours. HTRF signal was read on an EnVision multimode plate reader (CisBio) in HTRF mode. Data were fit to dose-response curves using XLfit (IDBS, Surrey, UK) or Prism (GraphPad Software, La Jolla, Calif., US) to calculate IC$_{50}$ values for each compound tested.

Example B: AlphaLisa Cellular Assay

Compound activity in cells was measured using an AlphaLISA® SureFire® Ultra™ p-CHK1 (Ser345) assay (Perkin Elmer, catalog no. ALSU-PCHK1-A10K). HT29 cells were cultured in McCoy 5A medium with 10% FBS and 1% penicillin-streptomycin and seeded to 96-well plates (Corning, catalog no. 3599). Compounds were serially diluted in DMSO over a 10-point dose range with 3-fold dilution and to each well containing cells was added compound solution. Plates were centrifuged at 1000 rpm for 30 seconds. Plates were incubated at 37° C. for 16 h. Supernatant was removed by flicking the plate against a paper towel. Wells were washed once with PBS solution. To each well was added freshly prepared lysis buffer and plates were agitated on a plate shaker at 400 rpm for 30 min. The 96-well cell plates were centrifuged at 1500 rpm for 1 minute. From each well was transferred 10 μL of the lysates to a 384-well Optiplate™ (Perkin Elmer, catalog no. 6007290). To each well was added Acceptor Mix (5 μL) and the plates were sealed and wrapped in foil. Plates were agitated on a plate shaker for 2 minutes, then incubated at room temperature for 1 h. To each well was added Donor Mix (5 μL) and the plates were sealed and wrapped in foil. Plates were agitated on a plate shaker for 2 minutes, then incubated at room temperature for 1 h. AlphaLisa signal was read on an EnVision multimode plate reader (Perkin Elmer). Data were fit to dose-response curves using XLfit (IDBS, Surrey, UK) or Prism (GraphPad Software, La Jolla, Calif., US) to calculate $IC_{50}$ values for each compound tested.

The data from example A and B is found in table 4.

TABLE 4

| Ex. | Chk1 Enzyme Activity | AlphaLisa Cellular Activity |
| --- | --- | --- |
| 1-1 | A | B |
| 1-2 | E | ND |
| 1-3 | E | ND |
| 1-4 | C | E |
| 1-5 | A | A |
| 1-6 | E | ND |
| 1-7 | A | A |
| 1-8 | A | A |
| 1-9 | B | C |
| 1-10 | C | E |
| 1-11 | B | C |
| 1-12 | A | C |
| 1-13 | B | C |
| 1-14 | A | A |
| 1-15 | C | ND |
| 1-16 | B | A |
| 1-17 | B | D |
| 1-18 | C | ND |
| 1-19 | B | C |
| 1-20 | B | C |
| 1-21 | A | B |
| 1-22 | B | C |
| 1-23 | B | C |
| 1-24 | E | ND |
| 1-25 | D | ND |
| 1-26 | B | B |
| 1-27 | B | C |
| 1-28 | A | A |
| 1-29 | A | C |
| 1-30 | E | ND |
| 1-31 | C | ND |
| 1-32 | B | D |
| 1-33 | C | ND |
| 1-34 | C | ND |
| 1-35 | C | ND |
| 1-36 | C | ND |
| 1-37 | C | E |
| 1-38 | B | C |
| 1-39 | B | D |
| 1-40 | C | E |
| 1-41 | A | C |
| 1-42 | B | B |
| 1-43 | B | A |
| 1-44 | A | A |
| 1-45 | A | B |
| 1-46 | A | A |
| 1-47 | A | A |
| 1-48 | A | B |
| 1-49 | A | A |
| 1-50 | C | E |
| 1-51 | B | E |
| 1-52 | B | C |
| 1-53 | A | B |
| 1-54 | B | ND |
| 1-55 | B | D |
| 1-56 | A | C |
| 1-57 | A | B |
| 1-58 | A | A |
| 1-59 | C | E |
| 1-60 | A | A |
| 1-61 | B | C |
| 1-62 | B | C |
| 1-63 | B | C |
| 1-64 | E | ND |
| 1-65 | E | ND |
| 1-66 | E | ND |
| 2-1 | D | E |
| 2-2 | B | D |
| 2-3 | B | C |
| 2-4 | A | A |
| 2-5 | B | C |
| 3-1 | B | C |
| 3-2 | A | A |
| 3-3 | C | ND |
| 3-4 | B | ND |
| 3-5 | A | A |
| 3-6 | C | ND |
| 3-7 | A | A |
| 3-8 | A | A |
| 3-9 | B | ND |
| 3-10 | A | A |
| 3-11 | A | A |
| 3-12 | E | E |
| 3-13 | C | E |
| 3-14 | D | E |
| 3-15 | A | A |
| 3-16 | B | C |
| 3-17 | B | ND |
| 3-18 | B | C |
| 3-19 | B | E |
| 3-20 | A | A |
| 3-21 | A | B |
| 3-22 | B | C |
| 3-23 | E | ND |
| 3-24 | B | D |
| 3-25 | B | C |
| 3-26 | A | A |
| 3-27 | A | B |
| 3-28 | A | C |
| 3-29 | A | C |
| 3-30 | A | C |
| 3-31 | C | ND |
| 3-32 | B | ND |
| 3-33 | B | B |
| 3-34 | E | ND |
| 3-35 | A | A |
| 3-36 | A | ND |
| 3-37 | B | ND |
| 3-38 | A | B |
| 3-39 | C | ND |
| 3-40 | A | A |
| 3-41 | C | ND |
| 3-42 | B | C |
| 3-43 | C | ND |
| 3-44 | B | D |
| 3-45 | A | A |
| 3-46 | A | B |
| 3-47 | A | B |
| 3-48 | A | A |
| 3-49 | B | C |
| 3-50 | B | B |
| 3-51 | E | ND |
| 3-52 | C | ND |
| 3-53 | E | ND |
| 3-54 | A | ND |
| 3-55 | A | ND |

TABLE 4-continued

| Ex. | Chk1 Enzyme Activity | AlphaLisa Cellular Activity |
|---|---|---|
| 4-1 | C | D |
| 4-2 | B | D |
| 4-3 | C | E |
| 4-4 | C | ND |
| 4-5 | A | A |
| 5-1 | A | A |
| 5-2 | B | C |
| 5-3 | A | A |
| 5-4 | C | E |

Chk1 Enzyme Activity
A: $IC_{50} \leq 10$ nM;
B: $10$ nM $< IC_{50} \leq 100$ nM
C: $100$ nM $< IC_{50} \leq 500$ nM
D: $500$ nM $< IC_{50} \leq 1$ μM
E: $IC_{50} > 1$ μM
ND: not determined
AlphaLisa Cellular Activity
A: $IC_{50} \leq 50$ nM;
B: $50$ nM $< IC_{50} \leq 100$ nM
C: $100$ nM $< IC_{50} \leq 500$ nM
D: $500$ nM $< IC_{50} \leq 1$ μM
E: $IC_{50} > 1$ μM
ND: not determined

Example C: Pharmaceutical Compositions

Example C1: Parenteral Composition

To prepare a parenteral pharmaceutical composition suitable for administration by injection, 100 mg of a water-soluble salt of a compound described herein is dissolved in DMSO and then mixed with 10 mL of 0.9% sterile saline. The mixture is incorporated into a dosage unit form suitable for administration by injection.

Example C2: Oral Composition

To prepare a pharmaceutical composition for oral delivery, 100 mg of a compound described herein is mixed with 750 mg of starch. The mixture is incorporated into an oral dosage unit for, such as a hard gelatin capsule, which is suitable for oral administration.

Example C3: Sublingual (Hard Lozenge) Composition

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

The examples and embodiments described herein are for illustrative purposes only and in some embodiments, various modifications or changes are to be included within the purview of disclosure and scope of the appended claims.

What is claimed is:

1. A compound of Formula (Ia), or a pharmaceutically acceptable salt, solvate, tautomer, or stereoisomer thereof:

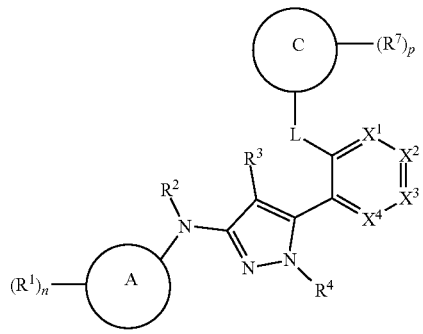

Formula (Ia)

wherein:

Ring A is heteroaryl;

each $R^1$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$; —NR$^b$C(=O)OR$^b$, —NHS(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl; or heteroaryl;

n is 0-4;

$R^2$ is hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;

$R^3$ is hydrogen, deuterium, halogen, —CN, —NO$_2$, —OH, —OR$^a$; —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;

$R^4$ is hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, cycloalkyl, or heterocycloalkyl;

$X^1$ is N or CR$^{5a}$;

$X^2$ is N or CR$^{5b}$;

$X^3$ is N or CR$^{5c}$;

$X^4$ is N or CR$^{5d}$;

$R^{5a}$, $R^{5b}$, $R^{5c}$, and $R^{5d}$ are independently hydrogen, deuterium, halogen, —CN, —NO$_2$, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^b$C(=O)NR$^c$R$^d$, —NR$^b$C(=O)R$^a$, —NR$^b$C(=O)OR$^b$, —NHS(=O)$_2$R$^a$, —C(=O)OR$^b$, —C(=O)NR$^c$R$^d$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

L is —O—;

Ring C is cycloalkyl;

each $R^7$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NHS(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two R$^7$ on the same atom are taken together to form an oxo;

p is 1 or 2;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, or C$_1$-C$_6$aminoalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, or C$_1$-C$_6$aminoalkyl; and each R$^c$ and R$^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, or C$_1$-C$_6$aminoalkyl;

or R$^c$ and R$^d$ are taken together with the atom to which they are attached to form a heterocycloalkyl optionally substituted with one or more oxo, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$haloalkyl, C$_1$-C$_6$deuteroalkyl, C$_1$-C$_6$hydroxyalkyl, or C$_1$-C$_6$aminoalkyl.

2. The compound of claim 1, or a pharmaceutically acceptable salt, solvate, tautomer, or stereoisomer thereof, wherein:

X$^1$ is CR$^{5a}$.

3. The compound of claim 2, or a pharmaceutically acceptable salt, solvate, tautomer, or stereoisomer thereof, wherein:

R$^{5a}$ is hydrogen, halogen, —OR$^a$, C$_1$-C$_6$alkyl, or C$_1$-C$_6$haloalkyl.

4. The compound of claim 1, or a pharmaceutically acceptable salt, solvate, tautomer, or stereoisomer thereof, wherein:

X$^2$ is CR$^{5b}$.

5. The compound of claim 4, or a pharmaceutically acceptable salt, solvate, tautomer, or stereoisomer thereof, wherein:

R$^{5b}$ is hydrogen, halogen, —OR$^a$, C$_1$-C$_6$alkyl, or C$_1$-C$_6$haloalkyl.

6. The compound of claim 1, or a pharmaceutically acceptable salt, solvate, tautomer, or stereoisomer thereof, wherein:

X$^3$ is CR$^{5c}$.

7. The compound of claim 6, or a pharmaceutically acceptable salt, solvate, tautomer, or stereoisomer thereof, wherein:

R$^{5c}$ is hydrogen, halogen, —OR$^a$, C$_1$-C$_6$alkyl, or C$_1$-C$_6$haloalkyl.

8. The compound of claim 1, or a pharmaceutically acceptable salt, solvate, tautomer, or stereoisomer thereof, wherein:

X$^4$ is CR$^{5d}$.

9. The compound of claim 8, or a pharmaceutically acceptable salt, solvate, tautomer, or stereoisomer thereof, wherein:

R$^{5d}$ is hydrogen, halogen, —OR$^a$, C$_1$-C$_6$alkyl, or C$_1$-C$_6$haloalkyl.

10. The compound of claim 1, or a pharmaceutically acceptable salt, solvate, tautomer, or stereoisomer thereof, wherein:

Ring A is pyrazinyl.

11. The compound of claim 1, or a pharmaceutically acceptable salt, solvate, tautomer, or stereoisomer thereof, wherein:

n is 1, and R$^1$ is —CN.

12. The compound of claim 1, or a pharmaceutically acceptable salt, solvate, tautomer, or stereoisomer thereof, wherein:

R$^2$ is hydrogen.

13. The compound of claim 1, or a pharmaceutically acceptable salt, solvate, tautomer, or stereoisomer thereof, wherein:

R$^3$ is hydrogen.

14. The compound of claim 1, or a pharmaceutically acceptable salt, solvate, tautomer, or stereoisomer thereof, wherein:

R$^4$ is hydrogen.

15. The compound of claim 1, or a pharmaceutically acceptable salt, solvate, tautomer, or stereoisomer thereof, wherein:

Ring C is monocyclic cycloalkyl.

16. The compound of claim 1, or a pharmaceutically acceptable salt, solvate, tautomer, or stereoisomer thereof, wherein:

Ring C is cyclobutyl, cyclopentyl, cyclohexyl, or cycloheptyl.

17. The compound of claim 1, or a pharmaceutically acceptable salt, solvate, tautomer, or stereoisomer thereof, wherein:

p is 1 and R$^7$ is —NR$^c$R$^d$.

18. The compound of claim 1, or a pharmaceutically acceptable salt, solvate, tautomer, or stereoisomer thereof selected from the group consisting of:
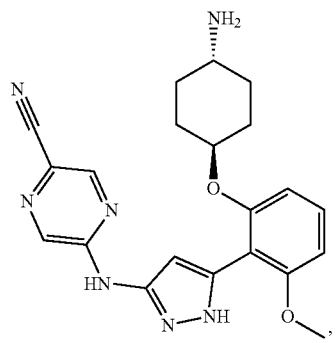
,
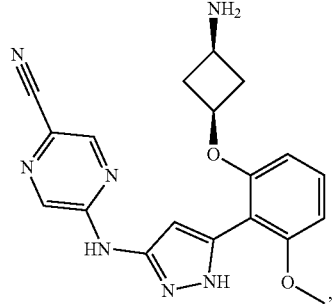
,
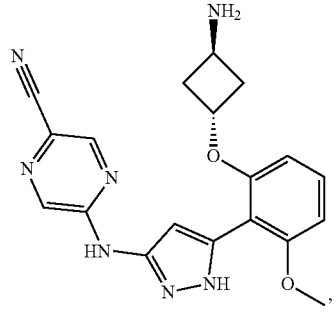
,
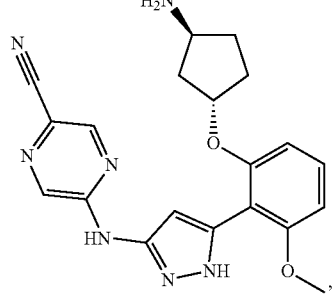
,
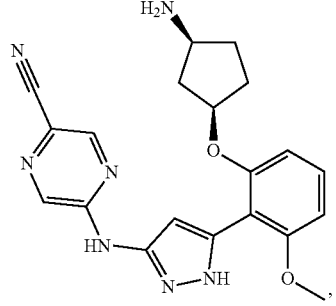
,
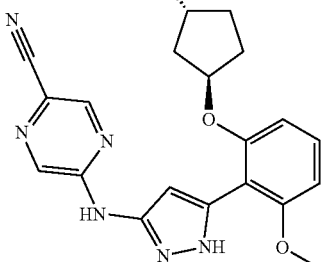
,
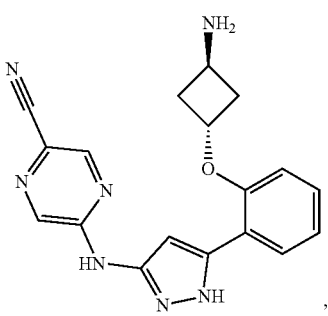
,
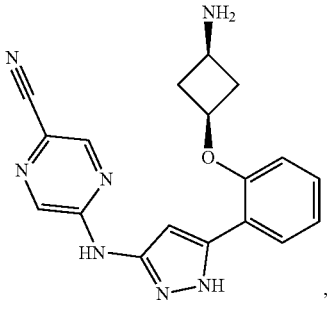
,
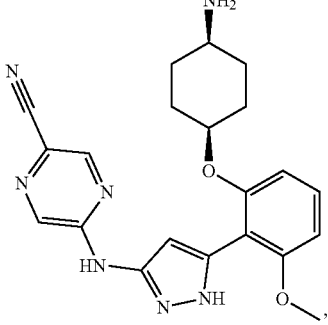
,
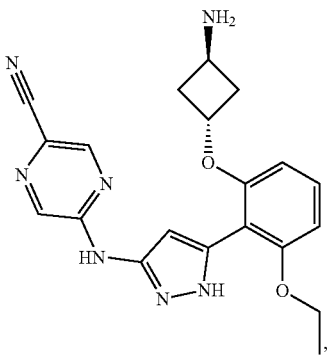
,

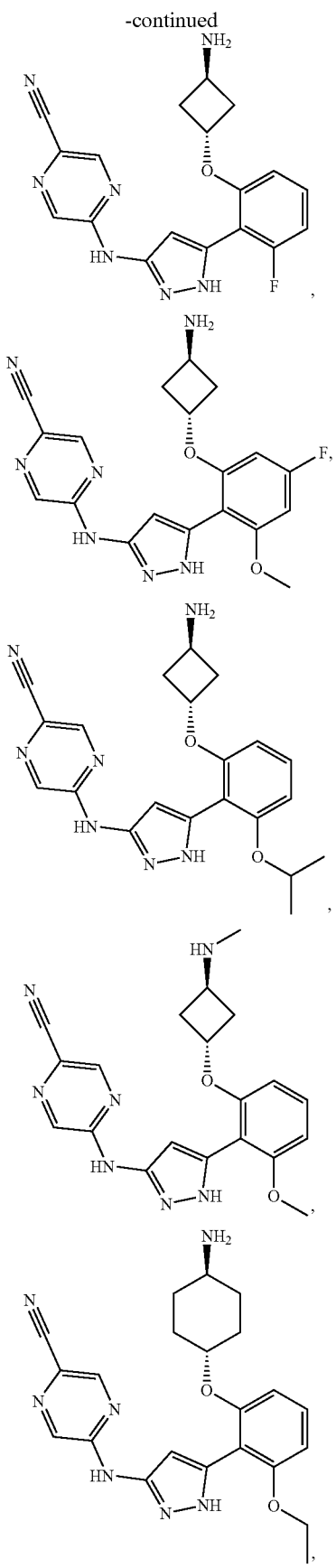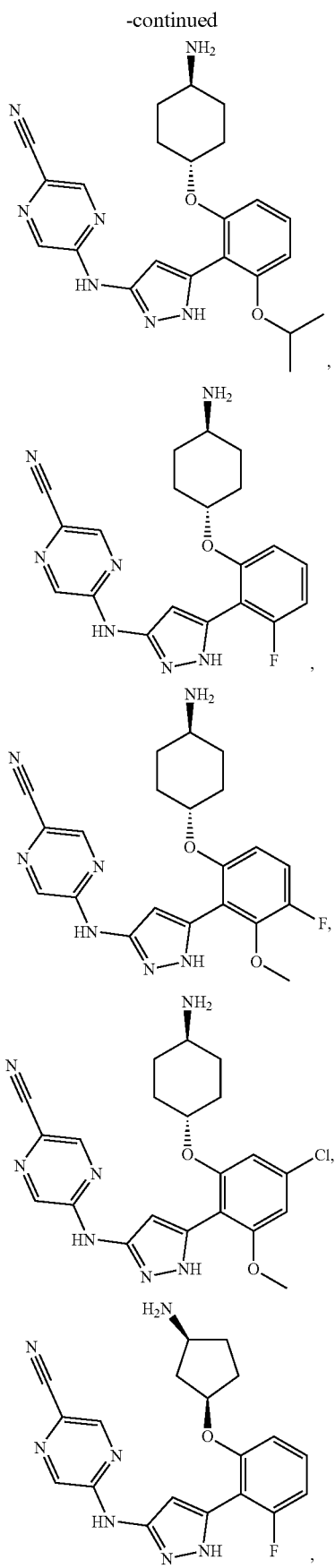

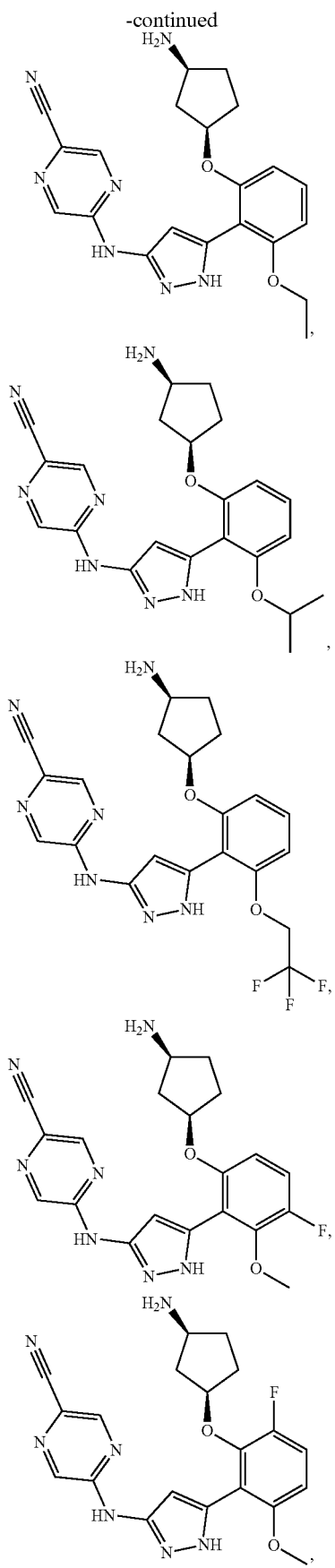
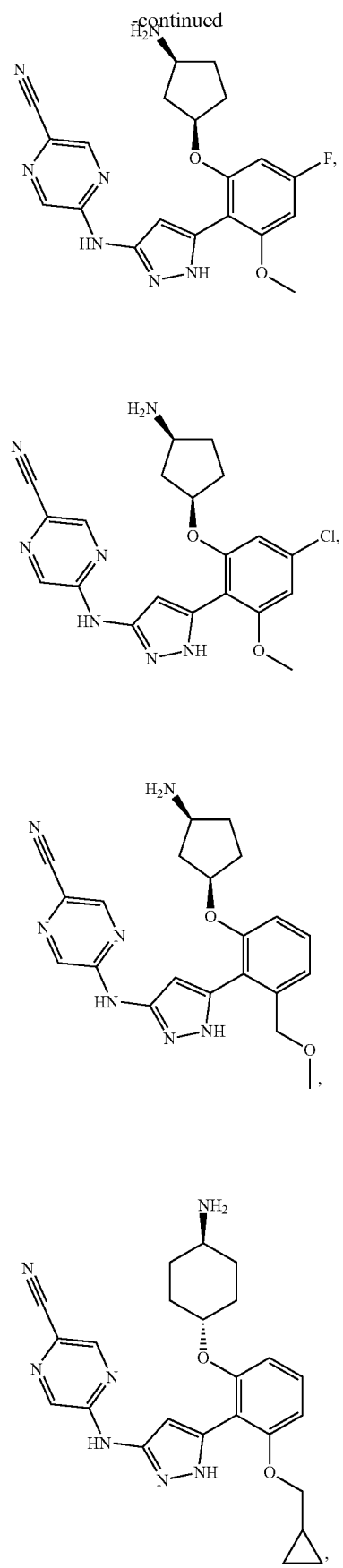

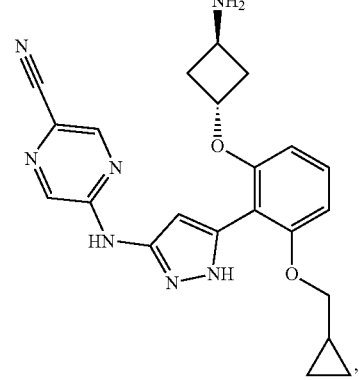
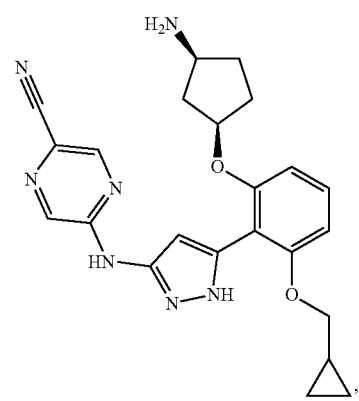
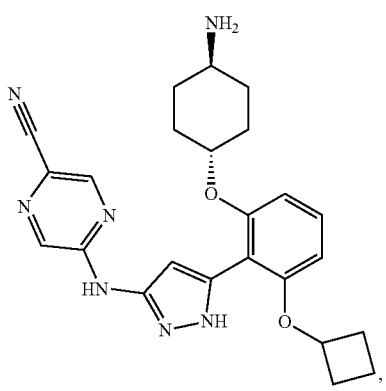
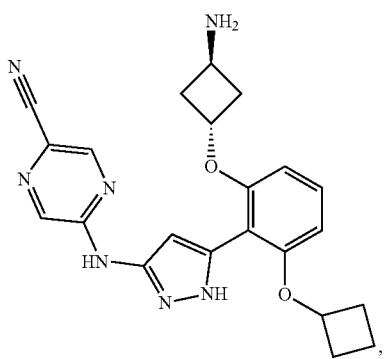
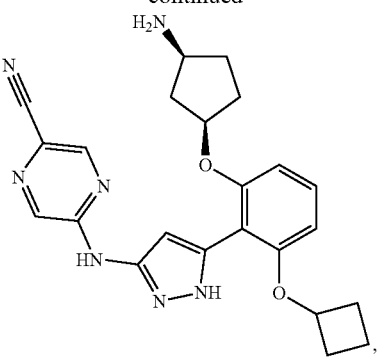
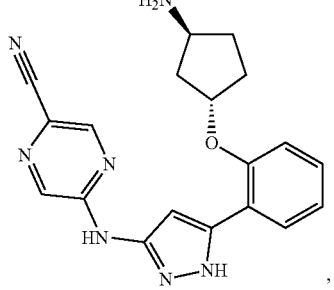
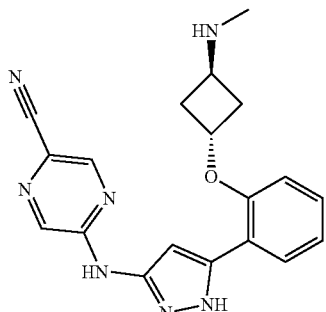
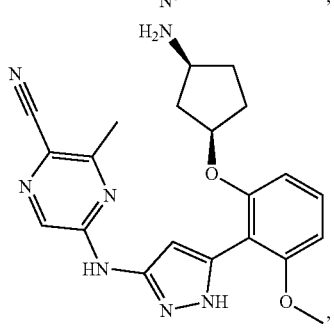
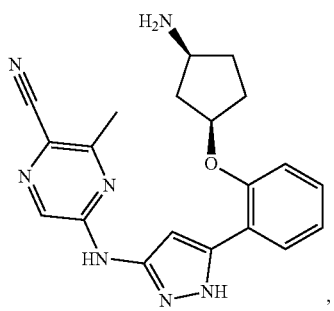

167
-continued
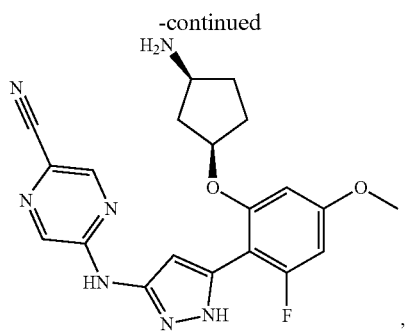
,
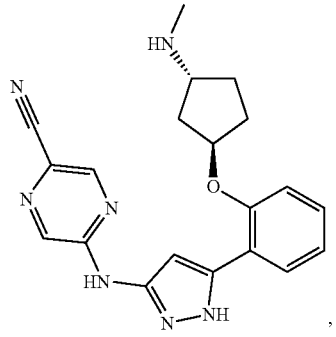
,
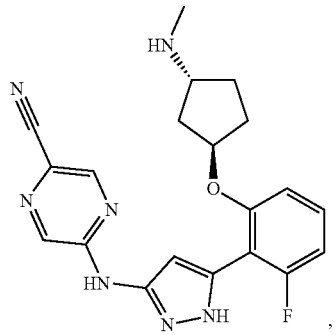
,
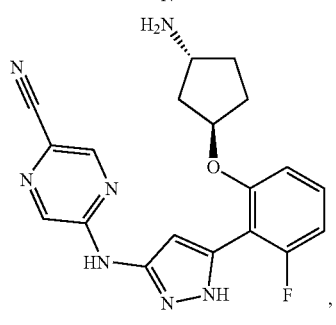
,
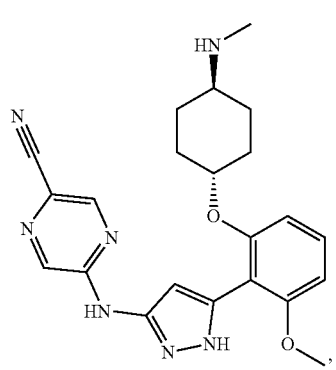
,
168
-continued
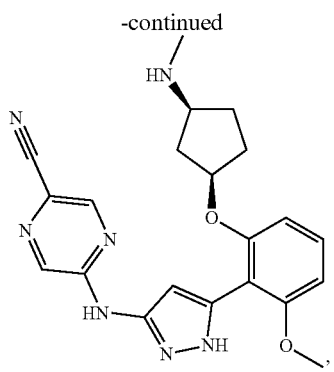
,
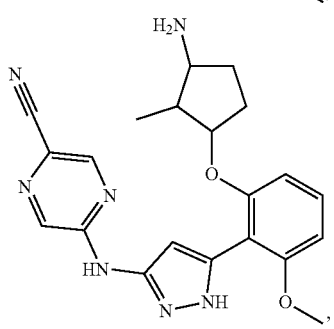
,
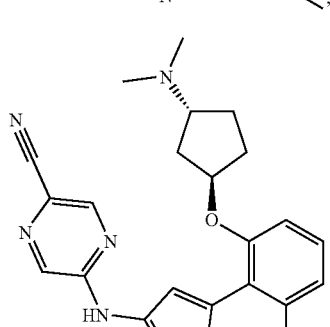
,
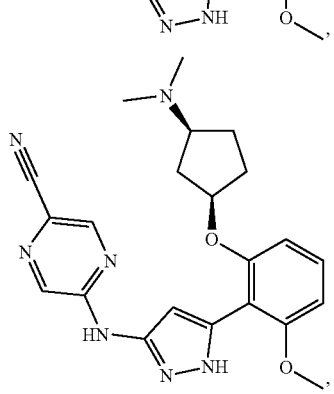
,
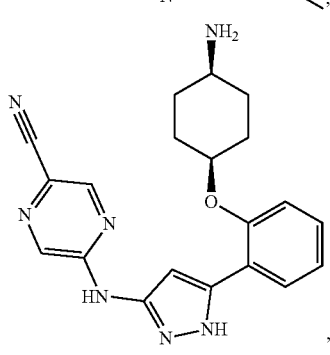
, -continued
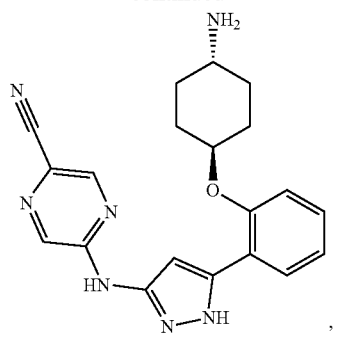
,
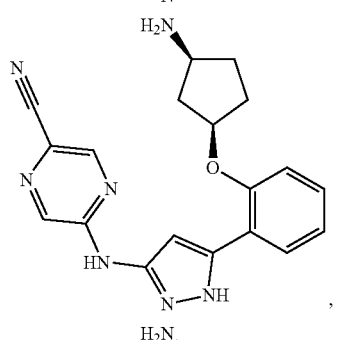
,
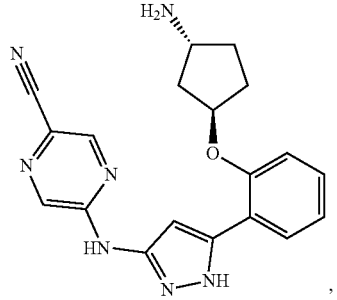
,
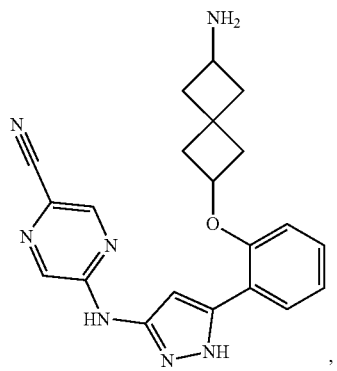
,
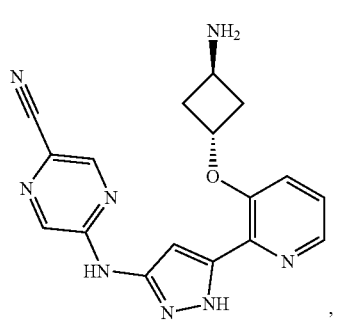
,
-continued
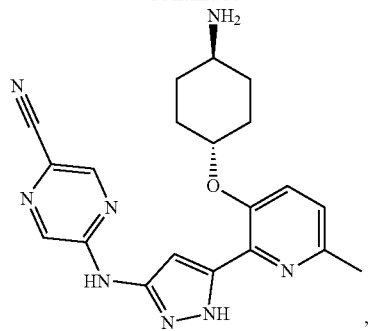
,
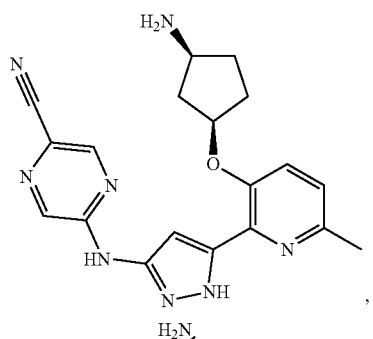
,
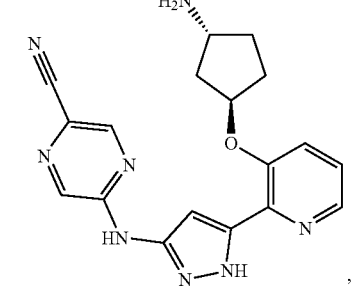
,
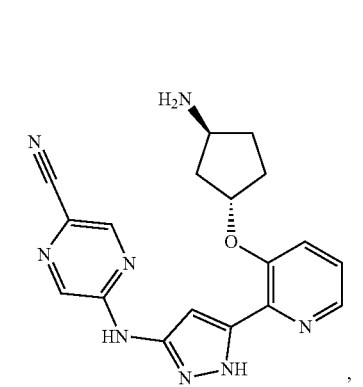
,
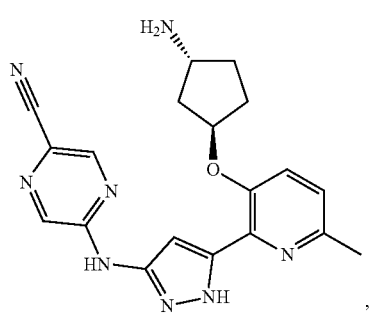
, -continued
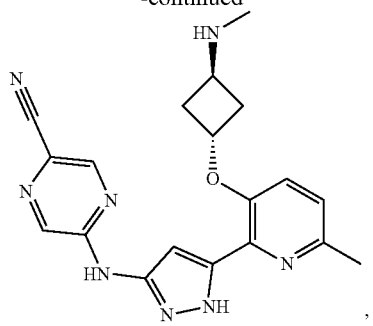,
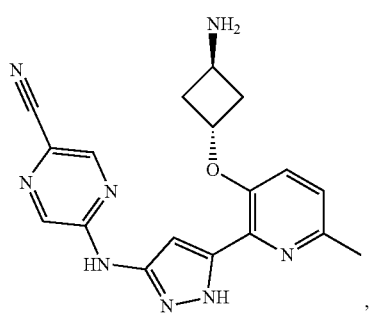,
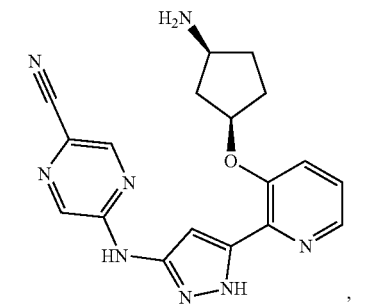,
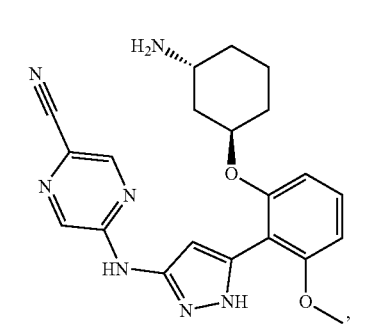,
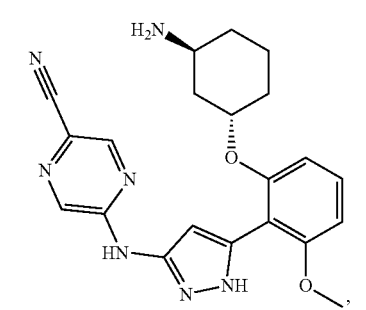,
-continued
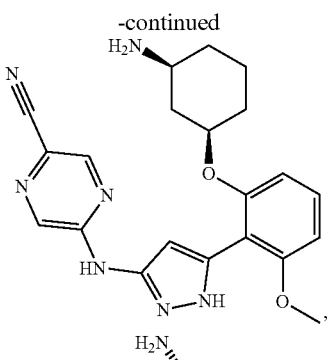,
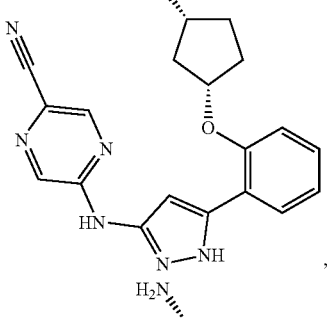,
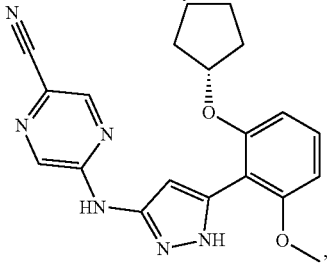,
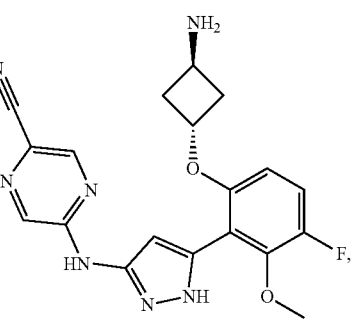,
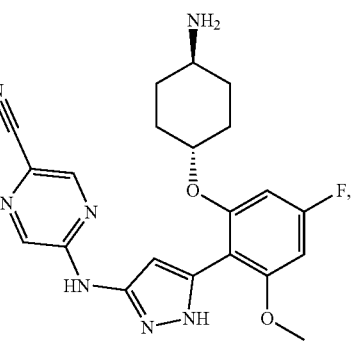,

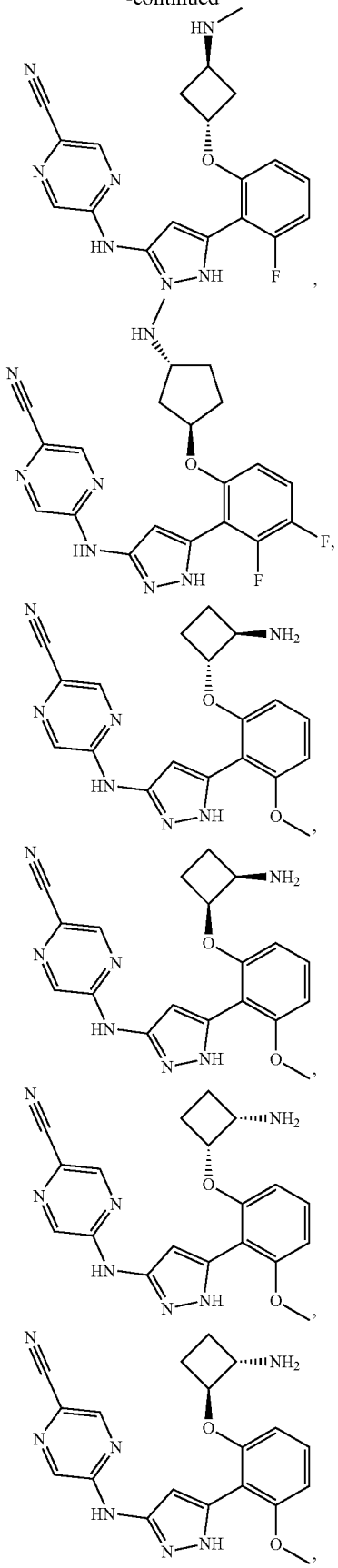
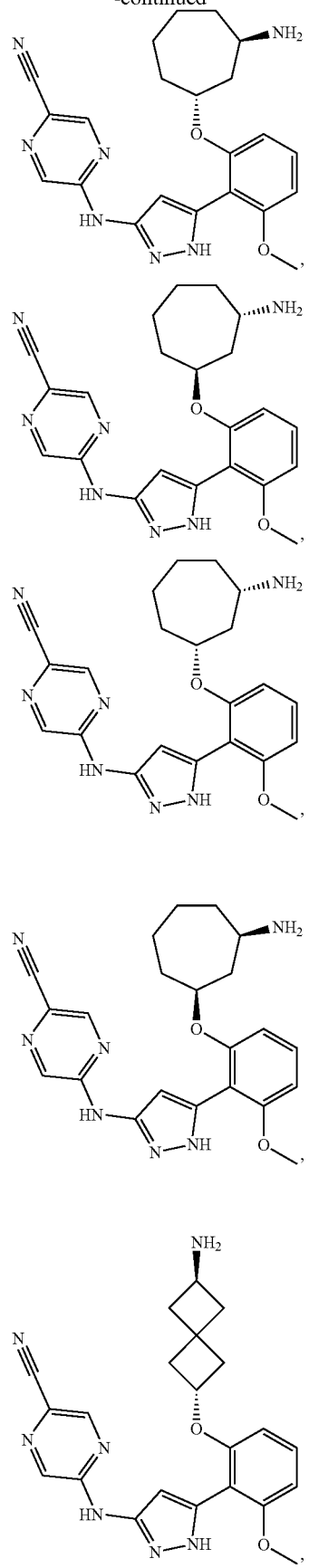

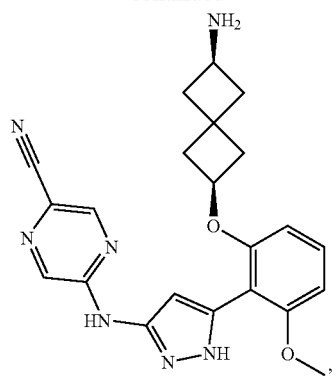
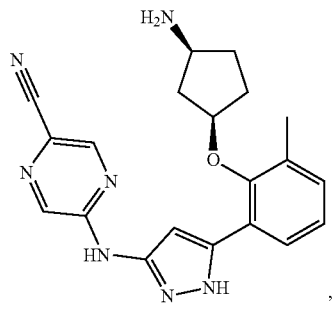
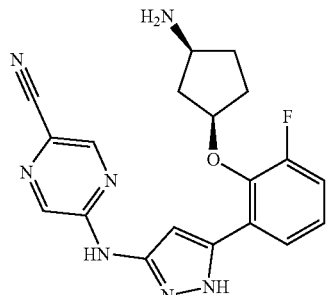
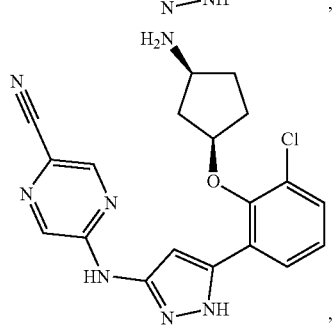
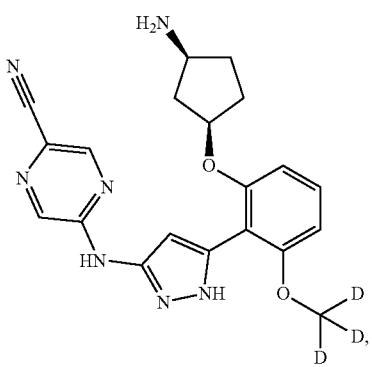
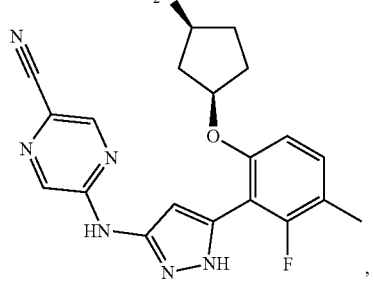
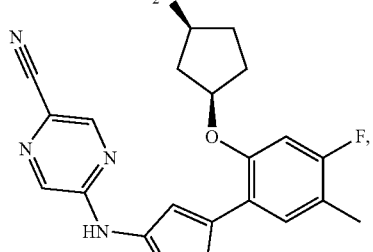
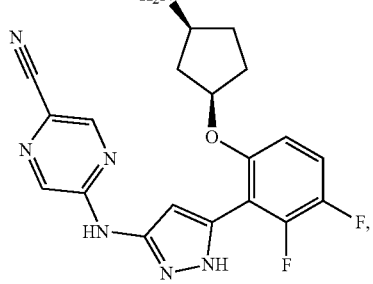
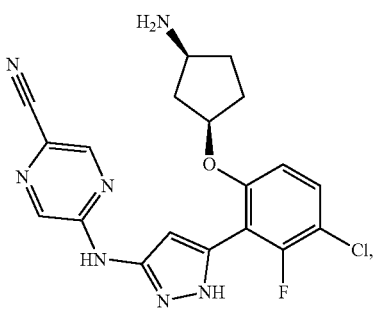
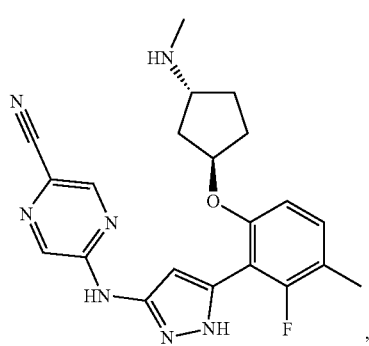

177
-continued
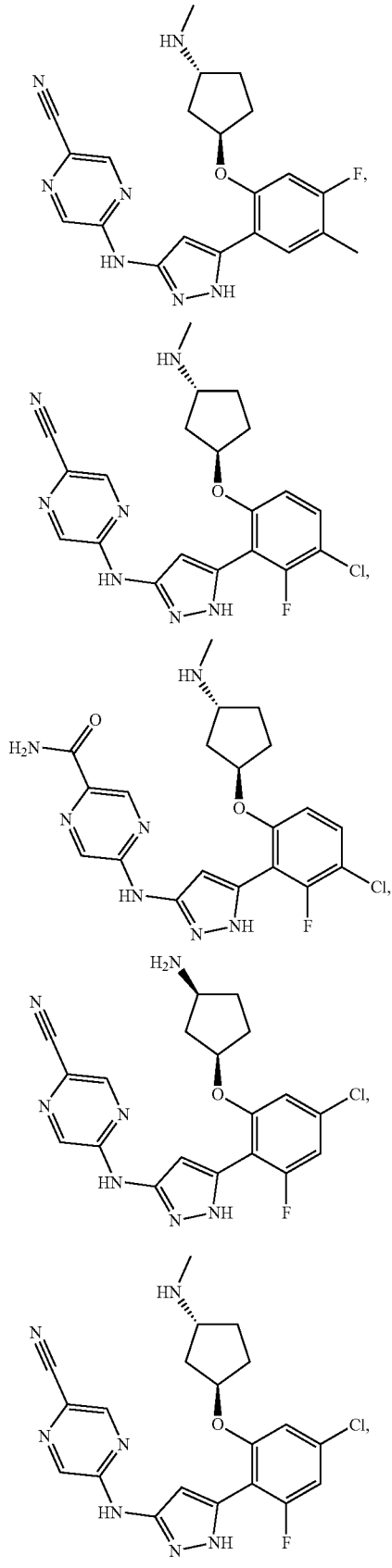
178
-continued
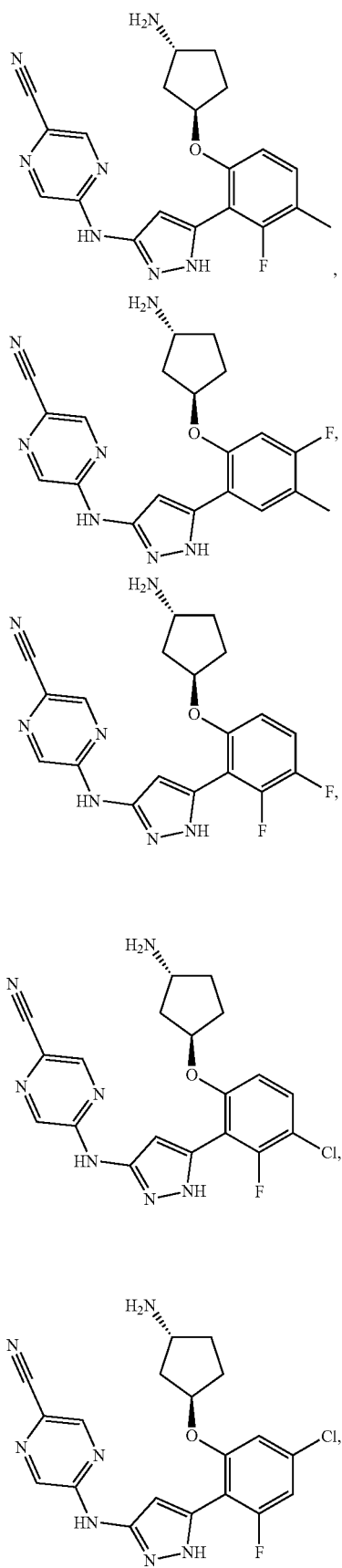

179
-continued
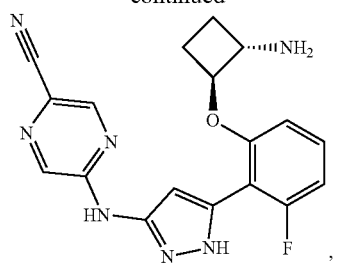,
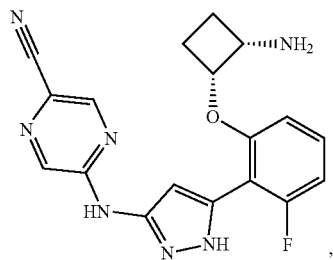,
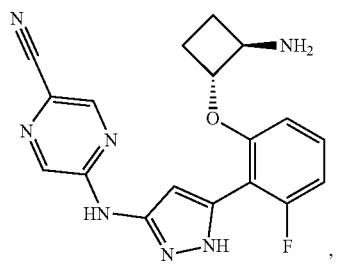,
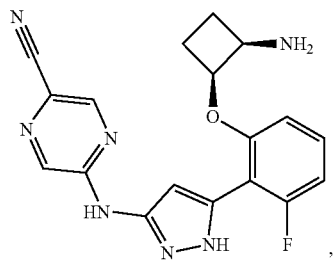,
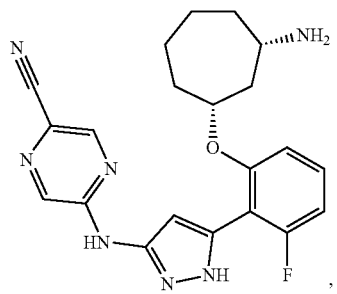,
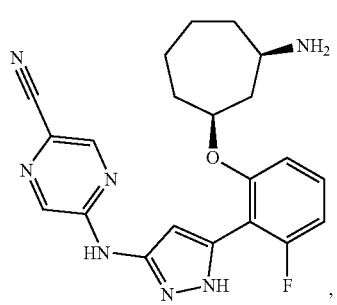,
180
-continued
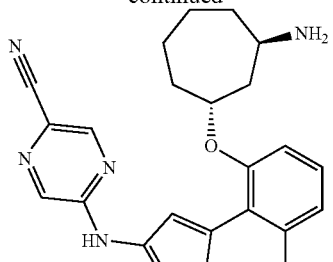,
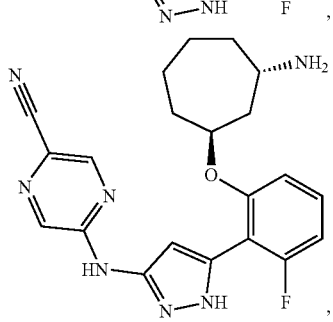,
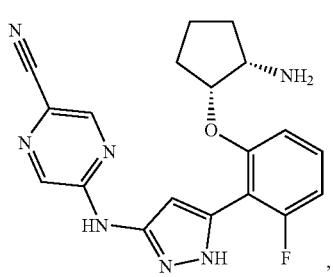,
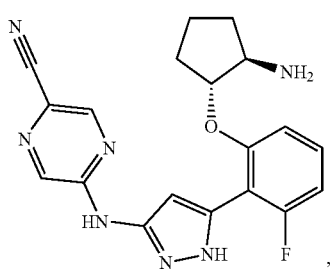,
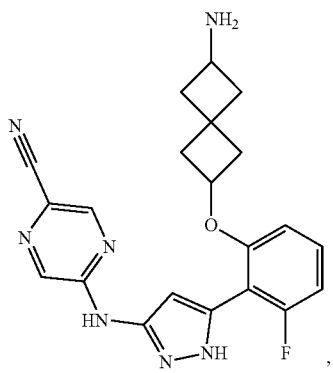, -continued
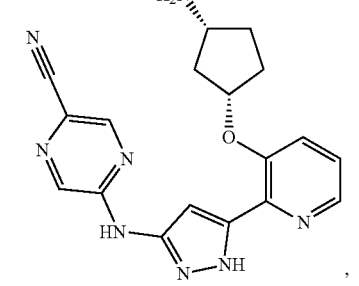
,
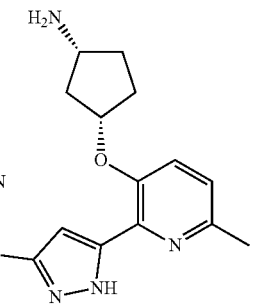
,
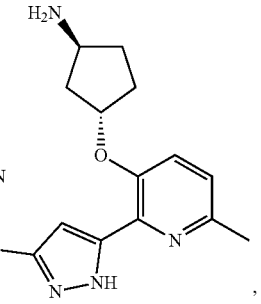
,
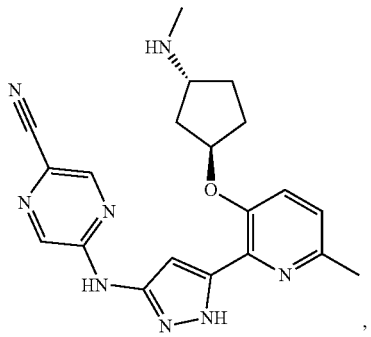
,
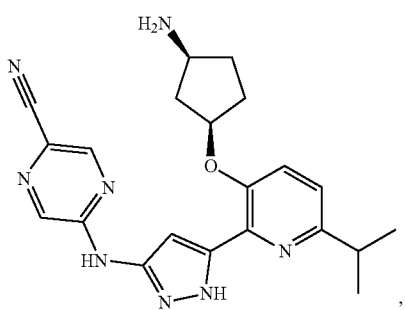
,
-continued
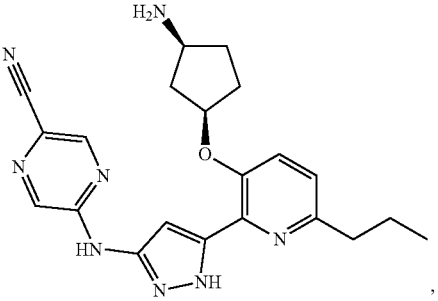
,
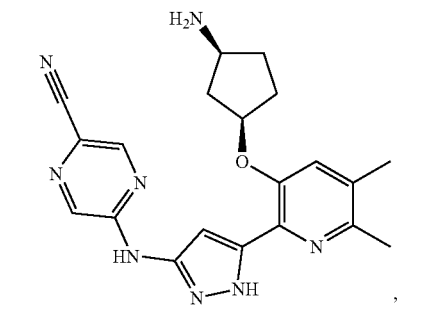
,
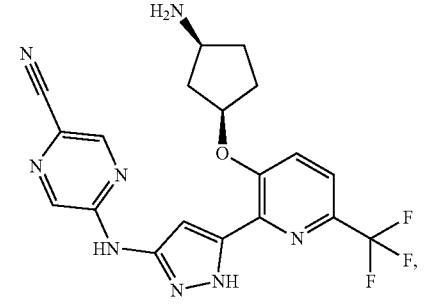
,
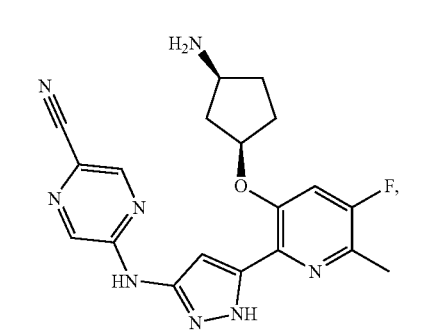
,
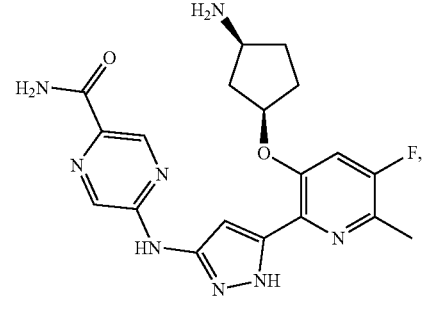
, -continued
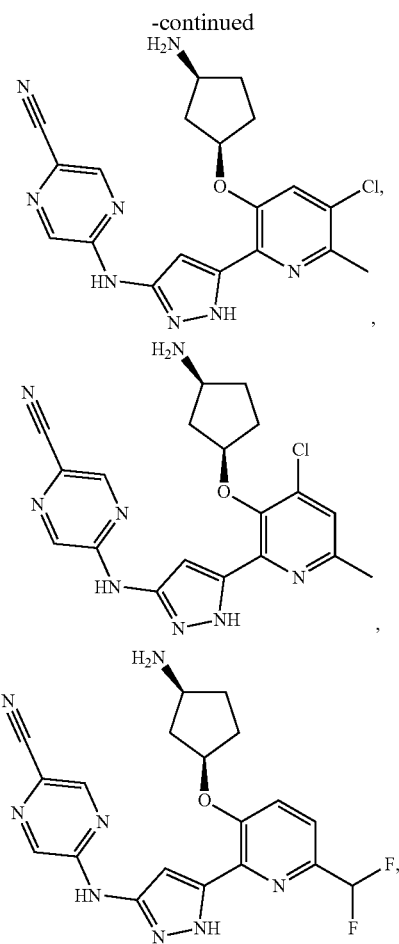
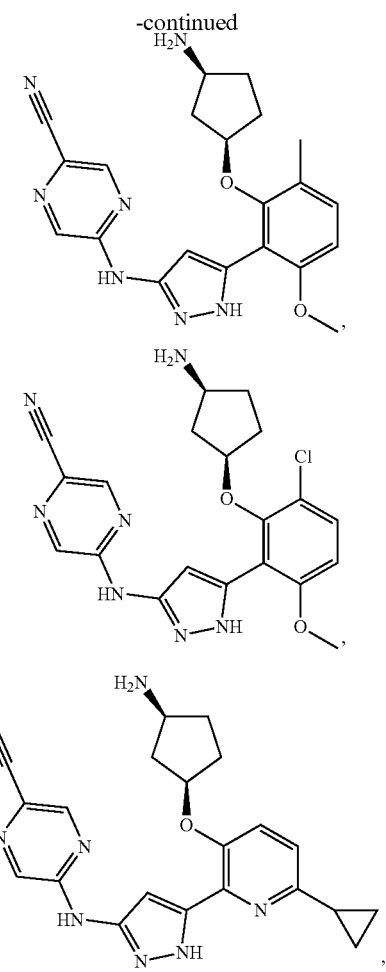

-continued
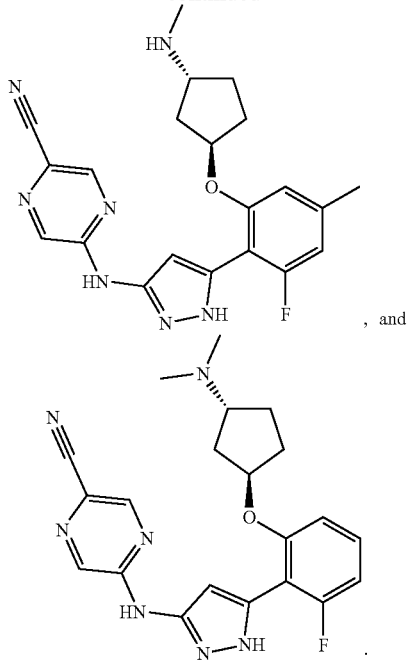
, and
19. A pharmaceutical composition comprising a compound of claim 1, or a pharmaceutically acceptable salt, solvate, tautomer, or stereoisomer thereof, and a pharmaceutically acceptable excipient.
* * * * *

UNITED STATES PATENT AND TRADEMARK OFFICE
CERTIFICATE OF CORRECTION

PATENT NO. : 11,707,462 B2
APPLICATION NO. : 17/897667
DATED : July 25, 2023
INVENTOR(S) : Anthony B. Pinkerton et al.

It is certified that error appears in the above-identified patent and that said Letters Patent is hereby corrected as shown below:

In the Claims

Column 156, Line 51:
In Claim 1 replace: "–$NO_2$, –$OR^a$" with -- –$NO_2$, –OH, –$OR^a$ --

Column 156, Line 53-56:
In Claim 1 replace: "–$S(=O)_2NR^cR^d$, –$NR^bC(=O)NR^cR^d$, –$NR^bC(=O)R^a$, –$NR^bC(C=O)OR^b$, –$NHS(=O)_2R^a$, –$C(=O)OR^b$, –$C(=O)NR^cR^d$, –$C(=O)NR^cR^d$, $C_1$-$C_6$alkyl" with -- –$S(=O)_2NR^cR^d$, –$NR^cR^d$, –$NR^bC(=O)NR^cR^d$, –$NR^bC(=O)R^a$, –$NR^bC(=O)OR^b$, –$NHS(=O)_2R^a$, –$C(=O)R^a$, –$C(=O)OR^b$, –$C(=O)NR^cR^d$, $C_1$-$C_6$alkyl --

Column 157, Line 12:
In Claim 1 replace: "$C_2$-$C_6$alkenyl, cycloalkyl" with -- $C_2$-$C_6$alkenyl, $C_2$-$C_6$alkynyl, cycloalkyl --

Column 157, Line 36:
In Claim 1 replace: "–$N(CH_3)_2$, –$C(=O)OH$" with -- –$N(CH_3)_2$, –$C(=O)CH_3$, –$C(=O)OH$ --

Column 157, Line 61:
In Claim 1 replace: "–$C(=O)OCH_3$, $C_1$-$C_6$haloalkyl" with -- –$C(=O)OCH_3$, $C_1$-$C_6$alkyl, $C_1$-$C_6$haloalkyl --

Signed and Sealed this
Fifth Day of September, 2023

*Katherine Kelly Vidal*
Katherine Kelly Vidal
*Director of the United States Patent and Trademark Office*